(12) United States Patent
Naik et al.

(10) Patent No.: US 11,524,934 B2
(45) Date of Patent: Dec. 13, 2022

(54) PHENYLAMINE COMPOUNDS

(71) Applicant: PI INDUSTRIES LTD., Gurgaon (IN)

(72) Inventors: Maruti Naik, Karnataka (IN); Vishal A. Mahajan, Maharashtra (IN); Gulab E. Walunj, Maharashtra (IN); Dipak D. Nivdunge, Maharashtra (IN); Sulur G. Manjunatha, Bangalore (IN); Ruchi Garg, Uttar Pradesh (IN); Santosh Shridhar Autkar, Maharashtra (IN); Nitin Ramesh Tembhare, Maharashtra (IN); Hagalavadi M. Venkatesha, Karnataka (IN); Konstantin Poscharny, Dusseldorf (DE); Alexander G. M. Klausener, Pulheim (DE)

(73) Assignee: PI INDUSTRIES LTD, Gurgaon (IN)

( * ) Notice: Subject to any disclaimer, the term of this patent is extended or adjusted under 35 U.S.C. 154(b) by 341 days.

(21) Appl. No.: 16/605,847

(22) PCT Filed: Apr. 18, 2018

(86) PCT No.: PCT/IB2018/052676
§ 371 (c)(1),
(2) Date: Oct. 17, 2019

(87) PCT Pub. No.: WO2018/193385
PCT Pub. Date: Oct. 25, 2018

(65) Prior Publication Data
US 2021/0122710 A1  Apr. 29, 2021

(30) Foreign Application Priority Data
Apr. 20, 2017 (IN) .............................. 201711014116

(51) Int. Cl.
| | | |
|---|---|---|
| C07C 257/12 | (2006.01) |
| C07D 207/00 | (2006.01) |
| A01N 37/00 | (2006.01) |
| A01N 39/00 | (2006.01) |
| A01N 43/00 | (2006.01) |
| A01N 37/52 | (2006.01) |
| A01N 43/36 | (2006.01) |
| A01N 43/38 | (2006.01) |
| A01N 43/40 | (2006.01) |
| A01N 43/50 | (2006.01) |
| A01N 43/52 | (2006.01) |
| A01N 43/56 | (2006.01) |
| A01N 43/653 | (2006.01) |
| A01N 43/78 | (2006.01) |
| A01N 43/84 | (2006.01) |
| A01N 43/90 | (2006.01) |
| C07C 323/45 | (2006.01) |
| C07D 207/36 | (2006.01) |
| C07D 209/12 | (2006.01) |
| C07D 213/81 | (2006.01) |
| C07D 231/44 | (2006.01) |
| C07D 231/56 | (2006.01) |
| C07D 235/04 | (2006.01) |
| C07D 239/26 | (2006.01) |
| C07D 249/08 | (2006.01) |
| C07D 277/68 | (2006.01) |
| C07D 295/16 | (2006.01) |
| C07D 471/04 | (2006.01) |

(52) U.S. Cl.
CPC ............ *C07C 257/12* (2013.01); *A01N 37/52* (2013.01); *A01N 39/00* (2013.01); *A01N 43/36* (2013.01); *A01N 43/38* (2013.01); *A01N 43/40* (2013.01); *A01N 43/50* (2013.01); *A01N 43/52* (2013.01); *A01N 43/56* (2013.01); *A01N 43/653* (2013.01); *A01N 43/78* (2013.01); *A01N 43/84* (2013.01); *A01N 43/90* (2013.01); *C07C 323/45* (2013.01); *C07D 207/36* (2013.01); *C07D 209/12* (2013.01); *C07D 213/81* (2013.01); *C07D 231/44* (2013.01); *C07D 231/56* (2013.01); *C07D 235/04* (2013.01); *C07D 239/26* (2013.01); *C07D 249/08* (2013.01); *C07D 277/68* (2013.01); *C07D 295/16* (2013.01); *C07D 471/04* (2013.01)

(58) Field of Classification Search
CPC .... C07C 257/12; C07D 207/36; A01N 37/52; A01N 39/00; A01N 43/00
See application file for complete search history.

(56) References Cited

U.S. PATENT DOCUMENTS

| | | |
|---|---|---|
| 3,296,272 A | 1/1967 | Johnston |
| 3,325,503 A | 6/1967 | Bimber |
| 2011/0130282 A1 | 6/2011 | Kunz et al. |

FOREIGN PATENT DOCUMENTS

| | | |
|---|---|---|
| CN | 1309897 A | 8/2001 |
| CN | 1456054 A | 11/2003 |

(Continued)

*Primary Examiner* — Sikarl A Witherspoon
(74) *Attorney, Agent, or Firm* — Fay Sharpe LLP

(57) ABSTRACT

The present invention relates to 4-substituted phenylamidine derivatives of the general formula (I), wherein R5-R6, ArA4, D, G, B, Q and an integer m have the meanings as defined in the description. The invention further relates to methods for their preparation and use of said compounds for controlling undesired phytopathogenic microorganisms, and agents for said purpose, comprising said phenylamine derivatives. This invention further relates to a method for controlling undesired phytopathogenic microorganisms by application of said 4-substituted phenylamidine derivatives of general formula (I) to such undesired microorganisms and/or to their habitat, according to the invention.

17 Claims, No Drawings

(56) References Cited

FOREIGN PATENT DOCUMENTS

| | | |
|---|---|---|
| CN | 1907024 A | 2/2007 |
| CN | 101337940 A | 1/2009 |
| CN | 102057925 A | 5/2011 |
| CN | 102060818 A | 5/2011 |
| CN | 103387541 A | 11/2013 |
| CN | 107200712 A | 9/2017 |
| DE | 196 50 197 A1 | 6/1998 |
| DE | 100 21 412 A1 | 6/2001 |
| DE | 10 2005 009 458 A1 | 9/2006 |
| EP | 0 141 317 A2 | 5/1985 |
| EP | 0 152 031 A2 | 8/1985 |
| EP | 0 226 917 A1 | 7/1987 |
| EP | 0 243 970 A1 | 11/1987 |
| EP | 0 256 503 A2 | 2/1988 |
| EP | 0 428 941 A1 | 5/1991 |
| EP | 0 532 022 A1 | 3/1993 |
| EP | 1 028 125 A1 | 8/2000 |
| EP | 1 035 122 A1 | 9/2000 |
| EP | 1 122 244 A1 | 8/2001 |
| EP | 1 201 648 A1 | 5/2002 |
| EP | 1 969 929 A1 | 9/2008 |
| EP | 2 865 265 A1 | 4/2015 |
| JP | 2002-316902 A | 10/2002 |
| WO | 94/01546 A1 | 1/1994 |
| WO | 98/46608 A1 | 10/1998 |
| WO | 99/14187 A1 | 3/1999 |
| WO | 99/24413 A2 | 5/1999 |
| WO | 99/27783 A1 | 6/1999 |
| WO | 00/29404 A1 | 5/2000 |
| WO | 00/46148 A1 | 8/2000 |
| WO | 00/46184 A1 | 8/2000 |
| WO | 00/65913 A1 | 11/2000 |
| WO | 01/54501 A2 | 8/2001 |
| WO | 01/56358 A1 | 8/2001 |
| WO | 02/22583 A2 | 3/2002 |
| WO | 02/40431 A2 | 5/2002 |
| WO | 03/010149 A1 | 2/2003 |
| WO | 03/011853 A1 | 2/2003 |
| WO | 03/014103 A1 | 2/2003 |
| WO | 03/016286 A1 | 2/2003 |
| WO | 03/016303 A1 | 2/2003 |
| WO | 03/053145 A1 | 7/2003 |
| WO | 03/061388 A1 | 7/2003 |
| WO | 03/066609 A1 | 8/2003 |
| WO | 03/074491 A1 | 9/2003 |
| WO | 03/076415 A1 | 9/2003 |
| WO | 03/093224 A1 | 11/2003 |
| WO | 03/106457 A1 | 12/2003 |
| WO | 2004/049804 A2 | 6/2004 |
| WO | 2004/083193 A1 | 9/2004 |
| WO | 2004/099160 A1 | 11/2004 |
| WO | 2005/063721 A1 | 7/2005 |
| WO | 2005/085216 A1 | 9/2005 |
| WO | 2005/087772 A1 | 9/2005 |
| WO | 2005/087773 A1 | 9/2005 |
| WO | 2005/120234 A2 | 12/2005 |
| WO | 2005/123689 A1 | 12/2005 |
| WO | 2005/123690 A1 | 12/2005 |
| WO | 2006/003494 A2 | 1/2006 |
| WO | 2006/015866 A1 | 2/2006 |
| WO | 2006/043635 A1 | 4/2006 |
| WO | 2006/087325 A1 | 8/2006 |
| WO | 2006/087343 A1 | 8/2006 |
| WO | 2007/006670 A1 | 1/2007 |
| WO | 2007/031507 A1 | 3/2007 |
| WO | 2007/031508 A1 | 3/2007 |
| WO | 2007/031512 A2 | 3/2007 |
| WO | 2007/031513 A1 | 3/2007 |
| WO | 2007/031523 A1 | 3/2007 |
| WO | 2007/031524 A1 | 3/2007 |
| WO | 2007/031526 A1 | 3/2007 |
| WO | 2007/061966 A2 | 5/2007 |
| WO | 2007/082098 A2 | 7/2007 |
| WO | 2007/090624 A2 | 8/2007 |
| WO | 2007/093227 A1 | 8/2007 |
| WO | 2007/129454 A1 | 11/2007 |
| WO | 2008/013622 A2 | 1/2008 |
| WO | 2008/064780 A1 | 6/2008 |
| WO | 2008/110278 A2 | 9/2008 |
| WO | 2008/110279 A1 | 9/2008 |
| WO | 2008/110280 A2 | 9/2008 |
| WO | 2008/110281 A2 | 9/2008 |
| WO | 2008/110312 A1 | 9/2008 |
| WO | 2008/110313 A1 | 9/2008 |
| WO | 2008/110314 A1 | 9/2008 |
| WO | 2008/110315 A1 | 9/2008 |
| WO | 2008/128639 A1 | 10/2008 |
| WO | 2008/134969 A1 | 11/2008 |
| WO | 2009/049851 A1 | 4/2009 |
| WO | 2009/053250 A1 | 4/2009 |
| WO | 2009/080250 A2 | 7/2009 |
| WO | 2009/083105 A1 | 7/2009 |
| WO | 2009/088103 A1 | 7/2009 |
| WO | 2009/090181 A2 | 7/2009 |
| WO | 2009/094442 A2 | 7/2009 |
| WO | 2009/099929 A1 | 8/2009 |
| WO | 2009/156074 A2 | 12/2009 |
| WO | 2009/156098 A2 | 12/2009 |
| WO | 2010/051926 A2 | 5/2010 |
| WO | 2010/069882 A1 | 6/2010 |
| WO | 2011/082941 A1 | 7/2010 |
| WO | 2010/086118 A1 | 8/2010 |
| WO | 2010/115758 A2 | 10/2010 |
| WO | 2010/139271 A1 | 12/2010 |
| WO | 2011/028657 A1 | 3/2011 |
| WO | 2011/077514 A1 | 6/2011 |
| WO | 2011/081174 A1 | 7/2011 |
| WO | 2011/120912 A1 | 10/2011 |
| WO | 2011/135833 A1 | 11/2011 |
| WO | 2012/000896 A2 | 1/2012 |
| WO | 2012/019998 A1 | 2/2012 |
| WO | 2012/025450 A1 | 3/2012 |
| WO | 2012/029672 A1 | 3/2012 |
| WO | 2012/060401 A1 | 5/2012 |
| WO | 2012/084812 A1 | 6/2012 |
| WO | 2012/090969 A1 | 7/2012 |
| WO | 2012/165511 A1 | 12/2012 |
| WO | 2012/168188 A1 | 12/2012 |
| WO | 2013/007767 A1 | 1/2013 |
| WO | 2013/010862 A1 | 1/2013 |
| WO | 2013/018735 A1 | 2/2013 |
| WO | 2013/024009 A1 | 2/2013 |
| WO | 2013/024010 A1 | 2/2013 |
| WO | 2013/047441 A1 | 4/2013 |
| WO | 2013/047749 A1 | 4/2013 |
| WO | 2013/092224 A1 | 6/2013 |
| WO | 2013/116251 A2 | 8/2013 |
| WO | 2013/127704 A1 | 9/2013 |
| WO | 2013/136275 A1 | 9/2013 |
| WO | 2013/144213 A1 | 10/2013 |
| WO | 2013/162072 A1 | 10/2013 |
| WO | 2014/037314 A2 | 3/2014 |
| WO | 2014/037315 A2 | 3/2014 |
| WO | 2014/060177 A1 | 4/2014 |
| WO | 2014/119617 A1 | 8/2014 |
| WO | 2014/157596 A1 | 10/2014 |
| WO | 2015/025962 A1 | 2/2015 |
| WO | 2015/121231 A1 | 8/2015 |
| WO | 2015/121802 A1 | 8/2015 |
| WO | 2016/202688 A1 | 12/2016 |
| WO | 2016/202742 A1 | 12/2016 |
| WO | 2017/005710 A1 | 1/2017 |
| WO | 2017/063973 A1 | 4/2017 |
| WO | 2017/067837 A1 | 4/2017 |
| WO | 2017/067839 A1 | 4/2017 |
| WO | 2017/102635 A1 | 6/2017 |

PHENYLAMINE COMPOUNDS

This application is a National Stage Entry of International Application No. PCT/IB2018/052676, filed Apr. 18, 2018, and entitled "NOVEL PHENYLAMINE COMPOUNDS"; which claims priority to Indian Application No. 201711014116, filed Apr. 20, 2017, and entitled "NOVEL PHENYLAMINE COMPOUNDS", the contents of which are incorporated by reference herein.

FIELD OF THE INVENTION

The present invention relates to compounds intended to protect crops by fighting undesired phytopathogenic microorganisms. More precisely, the subject of the present invention relates to novel phenylamine compounds used to protect crops by fighting undesired phytopathogenic microorganisms.

BACKGROUND OF THE INVENTION

The control of damages to crops caused by phytopathogenic microorganisms is extremely important in achieving high crop efficiency. For instance, plant disease damage to ornamental, vegetable, field, cereal, and fruit crops can cause significant reduction in productivity and thereby result in increased costs to the consumer. Many products are commercially available to control such damages. The need continues for new compounds which are more effective, less costly, less toxic, and environmentally safer and/or have different modes of action. Certain phenylamine derivatives are disclosed in literature as microbiocidally active ingredients in pesticides. For example, WO2000046184, WO2003093224 WO2005120234
WO2007031507 WO2007031526 WO2007031524
WO2007031523 WO2007031513 WO2007031508
WO2007031512 WO2007061966 WO2007093227
WO2008064780 WO2008110314 WO2008110313
WO2008110315 WO2008110278 WO2008110279
WO2008110280 WO2008110281 WO2008110312
WO2008128639 WO2009053250 WO2009083105
WO2009088103 WO2009156098 WO2009156074
WO2010086118 WO2010115758 WO2011082941
WO2011120912 WO2012019998 WO2012025450
WO2012060401 WO2012090969 WO2013018735
WO2013136275 WO2014037315 WO2014037314
WO2014119617 WO2014157596 WO2015025962
WO2015121231 WO2015121802 WO2016202742
WO2016202688 WO2017005710 WO2017063973
WO2017067839 WO2017067837 WO2017102635 and
CN107200712 discloses the phenylamidine derivatives and their use, either alone or as part of composition, as fungicides.

The effectiveness of the phenylamidine derivatives described in the prior art is good, but leaves something to be desired in various cases. Therefore, it is always of high interest in agriculture to use novel pesticidal compounds in order to avoid and/or control the development of microorganisms such as fungal or bacterial pathogens or pests being resistant to known active ingredients. It is therefore of high interest to use novel compounds being more active than those already known, with the aim of decreasing the amounts of active compound to be used, whilst at the same time maintaining an effectiveness at least equivalent to the already known compounds.

We have now found a new family of compounds which possess the above mentioned effects or advantages. A new family of compounds namely, novel phenylamidine derivatives wherein the phenyl ring is substituted according to the invention thus allowing an unexpected and significantly higher activity against undesired microorganisms such as fungal or bacterial pathogens or pests.

SUMMARY OF THE INVENTION

This present invention relates to 4-substituted phenylamine derivatives of the general formula (I)

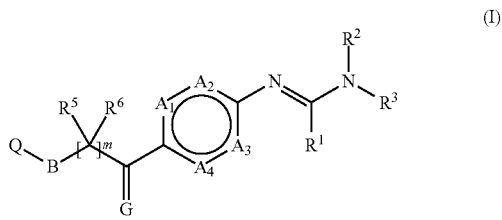

wherein the substituents of (I) are as defined in the description and claims.

The present invention also relates to agriculturally acceptable salts, structural isomers, stereo-isomers, diastereomers, enantiomers, tautomers, metal complexes, polymorphs, compositions or N-oxides of the compound of formula (I).

The present invention also relates to a composition comprising at least one compound of the present invention and optionally at least one other active compound selected from fungicides, insecticides, nematicides, acaricides, biopesticides, herbicides, plant growth regulators, antibiotics, fertilizers and or mixtures thereof. The present invention further relates to the use of the compound, the combination or the composition of the present invention and method of using the same, particularly in the field of agriculture mainly for protecting plants.

The compounds of the present invention are novel and have enhanced activity against microbials, particularly phytopathogenic fungi. The compounds of the present invention have application in the field of agriculture or may be used as intermediates for synthesizing compounds having wider applications.

DETAILED DESCRIPTION OF THE INVENTION

The present invention relates to compounds of general formula (I)

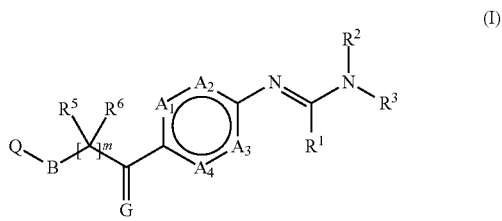

wherein
$R^1$ is selected from the group consisting of hydrogen, CN, SR", OR", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl, cyclic $C_4$-$C_8$-alkynyl; wherein one or more carbon atoms in cyclic ring system may be replaced by heteroatoms selected from the group consisting of N, O, S and optionally including 1 to 3 ring members selected from the group consisting of C(=O), C(=S), S(O), and SiR'$_2$;

$R^2$ and $R^3$ are independently selected from the group consisting of hydrogen, CN, S(O)$_n$R", OR", (C=O)—R", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl, cyclic $C_4$-$C_8$-alkynyl, $C_5$-$C_{18}$-aryl, $C_2$-$C_{19}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; or $R^1$ and $R^2$, $R^2$ or $R^3$ or $R^1$ and $R^3$ together with the atoms to which they are attached or together with further atoms selected from the group consisting of C, N, O, S and optionally including 1 to 3 ring members selected from the group consisting of C(=O), C(=S), S(O), and SiR'$_2$ may form a three to seven membered ring, which for its part may be substituted by one or more X, R', OR', SR', NR'$_2$, SiR'$_3$, COOR', CN or CONR'$_2$;

wherein, each of $R^1$, $R^2$; and $R^3$ may optionally be substituted by one or more groups selected from the group consisting of X, R', OR', SR', NR'$_2$, SiR'$_3$, COOR', CN or CONR'$_2$;

$A_1$, $A_2$, $A_3$ and $A_4$ represent $CR^4$ or nitrogen; with the proviso that no more than two of $A_1$, $A_2$, $A_3$ and $A_4$ are to be nitrogen simultaneously.

$R^4$ is independently selected from the group consisting of hydrogen, X, CN, NR"$_2$. SCN, SF$^5$, S(O)$_n$R", SiR'$_3$, OR", (C=O)—R", CR'=NR", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl, cyclic $C_4$-$C_8$-alkynyl, $C_5$-$C_{18}$-aryl, $C_7$-$C_{19}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O), and SiR'$_2$; or two $R^4$ together with the atom to which they are attached or together with further atoms selected from the group consisting of C, N, O, S and optionally including 1 to 3 ring members selected from the group consisting of C(=O), C(=S), S(O), and SiR'$_2$ may form a four to seven membered ring, which for its part may be substituted by one or more X, R', OR', SR', NR'$_2$, SiR'$_3$, COOR', CN or CONR'$_2$;

G and B represent O, S, NR" ' or CR'R$^6$;

m represents an integer of 1 or 2;

$R^5$ and $R^6$ are independently selected from the group consisting of hydrogen, X, CN, NR"$_2$, SCN, S(O)$_n$R", SiR'$_3$, OR', (C=O)—R", CR'=NR", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl, cyclic $C_4$-$C_8$-alkynyl, $C_5$-$C_{18}$-aryl, $C_7$-$C_{19}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O), and SiR'$_2$; or $R^5$ and $R^6$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered ring, which for its part may be substituted by one or more X, R', OR', SR', NR'$_2$, SiR'$_3$, COOR', CN or CONR'$_2$; or $R^5$ and $R^6$ together represent group selected from =S, =O;

Q is selected from the group consisting of fused or non-fused $C_3$-$C_{15}$-carbocyclyl or $C_3$-$C_{15}$-heterocyclyl; which may be optionally substituted by one or more groups of $R^7$; wherein $R^7$ is selected from the group consisting of hydrogen, X, CN, SCN, SF$^5$, OR", NO$_2$, NR"$_2$, SiR'$_3$, (C=O)—R", S(O)$_n$R", $C_1$-$C_8$-alkyl-S(O)$_n$R", $C_1$-$C_8$-alkyl-(C=O)—R", CR'=NR", S(O)$C_4$-$C_8$-aryl, S(O)$_n$$C_7$-$C_{19}$ aralkyl, $C_1$-$C_2$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, $C_1$-$C_2$-alkoxy, $C_1$-$C_{12}$-alkylthio, $C_1$-$C_{12}$-haloalkoxy, $C_1$-$C_2$-haloalkylthio, cyclic $C_3$-$C_8$-alkyl, cyclic $C_1$-$C_8$-haloalkyl, cyclic $C_4$-$C_8$-alkenyl, cyclic $C_4$-$C_8$-alkynyl, bicyclic $C_2$-$C_{12}$-alkyl, $C_7$-$C_2$-alkenyl, $C_6$-$C_{15}$-aryl, $C_7$-$C_{19}$-aralkyl, $C_3$-$C_6$-heterocyclyl, $C_3$-$C_8$-heterocyclylalkyl, $C_3$-$C_6$-heterocyclyloxy, $C_3$-$C_6$-heterocyclylthio; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; or two $R^7$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered ring, which for its part may be substituted by one or more X, R', OR', SR', NR'$_2$, SiR'$_3$, COOR', CN or CONR'$_2$;

wherein, each one of $R^4$, $R^5$, $R^6$, and $R^7$ may optionally be substituted by one or more groups selected from the group consisting of X, R', R", SR', SiR'$_3$, COOR', CN or CONR'$_2$;

wherein

X represents halogen;

R' represents hydrogen, $C_1$-$C_{12}$-alkyl or cyclic $C_3$-$C_{10}$-alkyl which may be optionally substituted by one or more X;

R" represents hydrogen, NR'2, CONR'$_2$, OR', $C_1$-$C_{12}$-alkyl, $C_1$-$C_{12}$-haloalkyl, cyclic $C_3$-$C_8$-alkyl which may be optionally substituted by one or more groups selected from the group consisting of X, R', OR', SR', NR'$_2$, SiR'$_3$, COOR', CN or CONR'$_2$, $C_5$-$C_{18}$-aryl which may be optionally substituted by one or more X, R', OR', SR', NR'$_2$, SiR'$_3$, COOR', CN or CONR'$_2$; wherein one or more carbon atoms in cyclic ring system may be replaced by heteroatoms selected from the group consisting of N, O, S and optionally including 1 to 3 ring members selected from the group consisting of C(=O), C(=S), S(O), and SiR'$_2$;

R'" is selected from the groups consisting of hydrogen, R", CN, OR', (C=O)—R', COOR', CONR'$_2$, $C_1$-$C_{12}$-alkyl, $C_2$-$C_{12}$-alkenyl, $C_2$-$C_{12}$-alkynyl, cyclic $C_3$-$C_8$-alkyl, cyclic $C_4$-$C_8$-alkenyl, cyclic $C_4$-$C_8$-alkynyl, $C_5$-$C_{18}$-aryl, $C_7$-$C_{19}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; each of the above groups may be substituted by one or more groups selected from the group consisting of X, R', OR', SR', NR'$_2$, SiR'$_3$, COOR', CN or CONR'$_2$;

n represents an integer ranging from 0 to 2;

According to an embodiment, $R^1$ is selected from hydrogen, $C_1$-$C_6$-alkyl, $C_1$-$C_6$-alkoxy, $C_1$-$C_6$-alkylthio, $C_1$-$C_6$-haloalkyl or $C_3$-$C_8$-cycloalkyl.

According to a more preferred embodiment, $R^1$ is selected from hydrogen, $C_1$-$C_6$-alkyl or $C_3$-$C_{15}$-cycloalkyl.

According to an embodiment, $R^2$ and $R^3$ are independently selected from CN, $C_1$-$C_6$-alkyl, $C_2$-$C_6$-alkenyl, $C_2$-$C_6$-alkynyl, $C_1$-$C_6$-alkoxy, $C_1$-$C_6$-alkylthio, $C_1$-$C_6$-haloalkyl, $C_3$-$C_8$-cycloalkyl or non aromatic $C_3$-$C_8$-heterocyclyl.

According to one another embodiment $R^1$ and $R^2$ or $R^3$ or $R^1$ and $R^3$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered non aromatic ring, which for its part may be substituted by one or more X, R', OR', SR', (C=O)—R", or CN.

According to one another embodiment the substitutions $R^1$ and $R^2$, $R^2$ and $R^3$ or $R^1$ and $R^3$ together with the atoms to which they are attached form a optionally substituted cyclic ring system selected from azetidine, pyrrolidine, imidazolidine, oxazolidine, piperidine, morpholine, thiomorpholine, piperazine, 1-methylpiperazine, 1-methylpyrrolidine, 1-methylpiperidine, 3-methyl-1,3-thiazinane.

According to an embodiment, $R^4$ is independently selected from hydrogen, X, CN, S(O)$_n$R", NR'R", (C=O)—R", CR'=NR", $C_1$-$C_6$-alkyl, $C_2$-$C_6$-alkenyl, $C_1$-$C_6$-haloalkyl, $C_1$-$C_6$-alkoxy, $C_1$-$C_6$-haloalkylthio, $C_3$-$C_8$-cycloalkyl or $C_3$-$C_8$-cycloalkylthio.

According to an embodiment, $R^5$ and $R^6$ are independently selected from hydrogen, X, CN, S(O)$_n$R", NR'R", (C=O)—R", CR'=NR", $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-cycloalkoxy, $C_3$-$C_8$-cycloalkylthio.

According to an embodiment $R^5$ and $R^6$ together with the atom to which they are attached or together with further atoms selected from the group consisting of C, N, O, S may form a three to six membered ring, which for its part may be substituted by one or more X, R', OR', SR', NR'$_2$, SiR'$_3$, COOR', CN, or CONR'$_2$.

According to an embodiment, $R^7$ is selected from hydrogen, X, CN, SCN, SF$_5$, R", OR", NO$_2$, NR"$_2$, SiR'$_3$, (C=O)—R", S(O)$_n$R", $C_1$-$C_6$-alkyl-S(O)$_n$R", $C_1$-$C_6$-alkyl-(C=O)—R", CR'=NR", $C_2$-$C_6$-alkenyl, $C_2$-$C_6$-alkynyl, $C_1$-$C_6$-haloalkyl, $C_2$-$C_6$-haloalkenyl, $C_1$-$C_6$-alkoxy, $C_1$-$C_6$-alkylthio, $C_1$-$C_6$-haloalkoxy, $C_1$-$C_6$-haloalkylthio, $C_3$-$C_8$-cycloalkyl, $C_4$-$C_8$-cycloalkenyl, $C_3$-$C_8$-cycloalkyloxy or $C_3$-$C_8$-cycloalkylthio.

In one another embodiment two $R^7$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a four to ten membered ring, which for its part may be substituted by one or more X, R', OR', SR', NR'$_2$, SiR'$_3$, COOR', CN or CONR'$_2$.

In one another embodiment Q is selected from cyclopropyl, cyclobutyl, phenyl, napthalenyl, furyl, thienyl, pyrrolyl, isoxazolyl, isothiazolyl, pyrazolyl, oxazolyl, imidazolyl, oxadiazolyl, triazolyl, pyridinyl, pyridazinyl, pyrimidinyl, pyrazinyl, triazinyl, indolyl, benzimidazolyl, indazolyl, benzofuranyl, benzothiophenyl, benzothiazolyl, benzoxazolyl, quinolinyl, isoquinolinyl, quinazolinyl, cinnonyl, indolizinyl, pyrazolo[1,5-a]pyridinyl, imidazo[1,2-a]pyridinyl, pyrrolo[1,2-a]pyrimidinyl, pyrazolo[1,5-a]pyrimidinyl, imidazo[1,2-a]pyrimidinyl, pyrrolo[1,2-a]pyrazinyl, pyrazolo[1,5-a]pyrazinyl, imidazo[1,2-a]pyrazinyl; substituted with one or more $R^7$.

According to preferred embodiment Q is selected from cyclopropyl, phenyl, napthalenyl, thienyl, isothiazolyl, thiazolyl, thiadiazolyl, pyrazolyl, pyridinyl, pyridazinyl, pyrimidinyl, pyrazinyl; substituted with one or more $R^7$.

Another embodiment provides, the use of compound of formula (I) and compositions thereof, for controlling or preventing against phytopathogenic fungi of agricultural crops and or horticultural crops.

A preferred embodiment provides, the use of compounds of formula (I) and compositions thereof, for controlling plant diseases: *Puccinia* spp. (rusts) on various plants, selected from, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, selected from wheat, barley or rye and *Phakopsoraceae* spp. on various plants, in particular *Phakopsora pachyrhizi* and *P. meibomiae* (soybean rust) on soybeans.

A preferred embodiment provides for, the use of compound of formula (I) and compositions thereof, more precisely for controlling and/or preventing against phytopathogenic fungi such as *Phakopsora pachyrhizi*, *Phakopsora meibomiae*, of agricultural crops and or horticultural crops.

A further preferred embodiment provides for the use of compound of formula (I) and compositions thereof, that are particularly suitable for controlling and/or preventing against diseases of the agricultural crops such as cereals, corn, soybean and other leguminous plants; fruits and fruit trees; nuts and nut trees; citrus and citrus trees; any horticultural plants; oleaginous plants; coffee, tea, and other vegetables, and ornamentals.

Definitions

The following definitions provided for the terminologies used in the present disclosure are for illustrative purpose only and in no manner limit the scope of the present invention disclosed in the present disclosure.

The transitional phrase "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited, except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition "A" or "B" is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "pesticide" in each case also always comprises the term "crop protection agent".

The term "undesired microorganisms" or "phytopathogenic microorganisms" such as fungal or bacterial pathogens includes namely Plasmodiophoromycetes, Oomycetes, Chytridiomycetes, Zygomycetes, Ascomycetes, Basidiomycetes and Deuteromycetes and Pseudomonadaceae, Rhizobiaceae, Enterobacteriaceae, Corynebacteriaceae and Streptomycetaceae respectively.

The term "agronomic" refers to the production of field crops such as for food, fuels, biofuels, any biomaterials and fiber and includes namely the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries), biofuel production crops such as corn, sugar/starch crops, sugar-beet and sweet sorghum, cellulosic crops such as switchgrass, miscanthus, corn stover, poplar, biodiesel crops rapeseed (canola), soybeans, palm oil, mustard, camelina, safflower, sunflower and jatropha and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Alkyl, alkenyl, alkynyl, carbocyclyl, heterocyclyl, aryl and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction under normal conditions (temperature, pressure, air etc.). Unless otherwise indicated, a "substituted" group has a substituent at one or more substitutable positions of the group, and when more than one position in any given structure is substituted, the substituent is either the same or different at each position.

Any of the compounds according to the invention can exist in one or more optical, geometric or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereomers and/or the optical isomers can be separated according to the methods which are known per se by a person ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by a person ordinary skilled in the art.

Any of the compounds according to the invention, can also exist in one or more amorphic or isomorphic or polymorphic forms, depending on their preparation, purification storage and various other influencing factors. The invention thus relates all the possible amorphic, isomorphic and polymorphic forms, in all proportions. The amorphic, isomorphic and polymorphic forms can be prepared and/or separated and/or purified according to general methods, which are known per se by a person ordinary skilled in the art.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_{24}$ alkyl, preferably $C_1$ to $C_{15}$ alkyl, more preferably $C_1$ to $C_{10}$ alkyl, most preferably $C_1$ to $C_6$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "alkenyl", used either alone or in compound words includes straight-chain or branched $C_1$ to $C_{24}$ alkenes, preferably $C_1$ to $C_1$ alkenes, more preferably $C_1$ to $C_{10}$ alkenes, most preferably $C_1$ to $C_6$ alkenes. Representative examples of alkenes include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl- 2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl and the different isomers. "Alkenyl" also includes polyenes such as 1,2-propadienyl and 2,4-hexadienyl. This definition also applies to alkenyl as a part of a composite substituent, for example haloalkenyl and the like, unless defined specifically elsewhere.

Representative examples of alkynes include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl and the different isomers. This definition also applies to alkynyl as a part of a composite substituent, for example haloalkynyl etc., unless specifically defined elsewhere. "Alkynyl" can also include moieties comprised of multiple triple bonds such as 2,5-hexadiynyl.

The term "cycloalkyl" or "cyclic alkyl" means alkyl closed to form a ring. Representative examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere. Cycloalkenyl or cyclicalkenyl means alkenyl closed to form a ring including monocyclic, partially unsaturated hydrocarbyl groups. Representative examples include but are not limited to cyclopropenyl, cyclobutenyl, cyclopentenyl and cyclohexenyl. This definition also applies to cycloalkenyl as a part of a composite substituent, for example cycloalkenylalkyl etc., unless specifically defined elsewhere.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The terms "haloalkenyl", "haloalkynyl" are defined analogously except that, instead of alkyl groups, alkenyl and alkynyl groups are present as a part of the substituent. The term "haloalkoxy" means straight-chain or branched alkoxy groups where some or all of the hydrogen atoms in these groups may be replaced by halogen atoms as specified above. Non-limiting examples of haloalkoxy include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere.

The term "haloalkoxy" means straight-chain or branch alkoxy groups where at least one up to all of the hydrogen atoms in these groups may be replaced by halogen atoms as specified above. Non-limiting examples of haloalkoxy include chloromethoxy, iodomethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere. The term "haloalkylthio" means straight-chain or branched alkylthio groups where some or all of the hydrogen atoms in these groups may be replaced by halogen atoms as specified above. Non-limiting examples of haloalkylthio include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio.

This definition also applies to haloalkylthio as a part of a composite substituent, for example haloalkylthioalkyl etc., unless specifically defined elsewhere. The term "alkoxy" used either alone or in compound words included $C_1$ to $C_{24}$ alkoxy, preferably $C_1$ to C alkoxy, more preferably $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term "aryl" as used herein is a group that contains any carbon-based aromatic group including, but not limited to, benzene, naphthalene, phenyl, biphenyl, anthracene, and the like. The aryl group can be substituted or unsubstituted. In addition, the aryl group can be a single ring structure or comprise multiple ring structures that are either fused ring structures or attached via one or more bridging groups such as a carbon-carbon bond.

The term "aralkyl" refers to aryl hydrocarbon radicals including an alkyl portion as defined above. Examples include benzyl, phenylethyl, and 6-napthylhexyl. As used herein, the term "aralkenyl" refers to aryl hydrocarbon radicals including an alkenyl portion, as defined above, and an aryl portion, as defined above. Examples include styryl, 3-(benzyl) prop-2-enyl, and 6-napthylhex-2-enyl.

The term "ring" or "ring system" as a component of formula I, Ia or Ib is parbocyclic or heterocyclic. The term "ring system" denotes one or more rings.

The term "bicyclic ring or ring system" denotes a ring system consisting of two or more common atom.

The terms "carbocycle" or "carbocyclic" or "carbocyclyl" include "aromatic carbocyclic ring system" and "nonaromatic carbocyclic ring system" or polycyclic or bicyclic (spiro, fused, bridged, nonfused) ring compounds in which the ring may be aromatic or non-aromatic (where aromatic indicates that the Hueckel rule is satisfied and non-aromatic indicates that the Hueckel rule is not satisfied).

Non limiting examples of non aromatic carbocyclic ring system are cyclopropyl, cyclobutyl, cyclopentyl, norbornyl and the like.

Non limiting examples of aromatic carbocyclic ring system are phenyl, napthalene and the like.

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs.

The terms "heterocycle" or "heterocyclic" or "heterocyclyl" include "aromatic heterocycle or heteroaryl ring system" and "nonaromatic heterocycle ring system" or polycyclic or bicyclic (spiro, fused, bridged, nonfused) ring compounds in which the ring may be aromatic or non-aromatic, wherein the heterocycle ring contains at least one heteroatom selected from N, O, $S(O)_{0-2}$, and or C ring member of the heterocycle may be replaced by C(=O), C(=S), C(=CR*R*) and C=NR*, * indicates integers (where aromatic heterocycle or heteroaryl ring indicates that the Hueckel rule is satisfied).

The term "non-aromatic heterocycle" means three- to fifteen-membered, preferably three- to twelve-membered, saturated or partially unsaturated heterocycles containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydroxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl and cycloserines. This definition also applies to heterocyclyl as a part of a composite substituent, for example heterocyclyloalkyl etc., unless specifically defined elsewhere.

The term "heteroaryl" as used herein is a group that contains fused or unfused three to fifteen membered, preferably three to twelve membered, more preferably 5 or 6 membered; monocyclic or polycyclic unsaturated ring system, containing heteroatoms selected from the group of oxygen, nitrogen, sulphur, phosphorous, boron etc.

Non-limiting examples of 5 membered heteroaryl groups include 2-furyl; 3-furyl; 2-thienyl; 3-thienyl; 2-pyrrolyl; 3-pyrrolyl; 3-isoxazolyl; 4-isoxazolyl; 5-isoxazolyl; 3-isothiazolyl; 4-isothiazolyl; 5-isothiazolyl; 3-pyrazolyl; 4-pyrazolyl; 5-pyrazolyl; 2-oxazolyl; 4-oxazolyl; 5-oxazolyl; 2-thiazolyl; 4-thiazolyl; 5-thiazolyl; 2-imidazolyl; 4-imidazolyl; 1,2,4-oxadiazol-3-yl; 1,2,4-oxadiazol-5-yl; 1,2,4-thiadiazol-3-yl; 1,2,4-thiadiazol-5-yl; 1,2,4-triazol-3-yl; 1,3,4-oxadiazol-2-yl; 1,3,4-thiadiazol-2-yl and 1,3,4-triazol-2-yl; 1-pyrrolyl; 1-pyrazolyl; 1,2,4-triazol-1-yl; 1-imidazolyl; 1,2,3-triazol-1-yl; 1,3,4-triazol-1-yl and the like.

Non-limiting examples of 6 membered heteroaryl groups include 2-pyridinyl; 3-pyridinyl; 4-pyridinyl; 3-pyridazinyl; 4-pyridazinyl; 2-pyrimidinyl; 4-pyrimidinyl; 5-pyrimidinyl; 2-pyrazinyl; 1,3,5-triazin-2-yl; 1,2,4-triazin-3-yl; 1,2,4,5-tetrazin-3-yl and the like.

Non-limiting examples of benzofused 5-membered heteroaryl include indol-1-yl; indol-2-yl; indol-3-yl; indol-4-yl; indol-5-yl; indol-6-yl; indol-7-yl; benzimidazol-1-yl; benzimidazol-2-yl; benzimidazol-4-yl; benzimidazol-5-yl; indazol-1-yl; indazol-3-yl; indazol-4-yl; indazol-5-yl; indazol-6-yl; indazol-7-yl; indazol-2-yl; 1-benzofuran-2-yl; 1-benzofuran-3-yl; 1-benzofuran-4-yl; 1-benzofuran-5-yl; 1-benzofuran-6-yl; 1-benzofuran-7-yl; 1-benzothiophen-2-yl; 1-benzothiophen-3-yl; 1-benzothiophen-4-yl; 1-benzothiophen-5-yl; 1-benzothiophen-6-yl; 1-benzothiophen-7-yl; 1,3-benzothiazol-2-yl; 1,3-benzothiazol-4-yl; 1,3-benzothiazol-5-yl; 1,3-benzothiazol-6-yl; 1,3-benzothiazol- 7-yl; 1,3-benzoxazol-2-yl; 1,3-benzoxazol-4-yl; 1,3-benzoxazol-5-yl; 1,3-benzoxazol-6-yl; 1,3-benzoxazol-7-yl and the liked.

Non-limiting examples of benzofused 6-membered heteroaryl include quinolin-2-yl; quinolin-3-yl; quinolin-4-yl; quinolin-5-yl; quinolin-6-yl; quinolin-7-yl; quinolin-8-yl; isoquinolin-1-yl; isoquinolin-3-yl; isoquinolin-4-yl; isoquinolin-5-yl; isoquinolin-6-yl; isoquinolin-7-yl; isoquinolin-8-yl and the like.

Non-limiting examples of fused 6-5-membered heteroaryl include Indolizinyl, pyrazolo[1,5-a]pyridinyl, imidazo[1,2-a]pyridinyl, pyrrolo[1,2-a]pyrimidinyl, pyrazolo[1,5-a]pyrimidinyl, imidazo[1,2-a]pyrimidinyl, pyrrolo[1,2-a]pyrazinyl, pyrazolo[1,5-a]pyrazinyl, imidazo[1,2-a]pyrazinyl and the like.

The total number of carbon atoms in a substituent group is indicated by the "$C_i$-$C_j$" prefix where i and j are numbers from 1 to 21. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH)$, $CH_3OCH_2CH_2$ or $CH_3CH_2CH_2$; and $C_4$ alkoxyalkyl designates the various isomers of an alkyl group substituted with an alkoxy group containing a total of four carbon atoms, examples including $CH_3CH_2CH_2CH_2$ and $CH_3CH_2OCH_2CH_2$. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates that the number of said substituents can exceed 1, said substituents (when they exceed 1) are independently selected from the group of defined substituents. Further, when the subscript m in $(R)_m$ indicates an integer ranging from for example 0 to 4, then the number of substituents may be selected from the integers from 0 and 4 inclusive.

When a group contains a substituent which can be hydrogen, then, when this substituent is taken as hydrogen, it is recognized that said group is being un-substituted.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skilled in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned in the description and the foregoing claims though might form a critical part of the present invention of the present disclosure, any deviation from such numerical values shall still fall within the scope of the present disclosure if that deviation follows the same scientific principle as that of the present invention disclosed in the present disclosure.

The term "pest" for the purpose of the present disclosure includes but is not limited to fungi, stramenopiles (oomycetes), bacteria, nematodes, mites, ticks, insects and rodents.

The term "plant" is understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights.

For the purpose of the present disclosure the term "plant" includes a living organism of the kind exemplified by trees, shrubs, herbs, grasses, ferns, and mosses, typically growing in a site, absorbing water and required substances through its roots, and synthesizing nutrients in its leaves by photosynthesis.

Examples of "plant" for the purpose of the present invention include but are not limited to agricultural crops such as wheat, rye, barley, triticale, oats or rice; beet, e.g. sugar beet or fodder beet; fruits and fruit trees, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit and citrus trees, such as oranges, lemons, grapefruits or mandarins; any horticultural plants, vegetables, such as spinach, lettuce, asparagus, cabbages, carrots, onions, tomatoes, potatoes, cucurbits or paprika; lauraceous plants, such as avocados, cinnamon or camphor; cucurbitaceae; oleaginous plants; energy and raw material plants, such as cereals, corn, soybean, other leguminous plants, rape, sugar cane or oil palm; tobacco; nuts; coffee; tea; cacao; bananas; peppers; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants.

Preferably, the plant for the purpose of the present invention include but is not limited to cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and vegetables, ornamentals, any floricultural plants and other plants for use of human and animals.

The term "plant parts" is understood to mean all parts and organs of plants above and below the ground. For the purpose of the present disclosure the term plant parts includes but is not limited to cuttings, leaves, twigs, tubers, flowers, seeds, branches, roots including taproots, lateral roots, root hairs, root apex, root cap, rhizomes, slips, shoots, fruits, fruit bodies, bark, stem, buds, auxiliary buds, meristems, nodes and internodes.

The term "locus thereof" includes soil, surroundings of plant or plant parts and equipment or tools used before, during or after sowing/planting a plant or a plant part.

Application of the compounds of the present disclosure or the compound of the present disclosure in a composition optionally comprising other compatible compounds to a plant or a plant material or locus thereof include application by a technique known to a person skilled in the art which include but is not limited to spraying, coating, dipping, fumigating, impregnating, injecting and dusting.

The term "applied" means adhered to a plant or plant part either physically or chemically including impregnation.

The present invention further relates to a composition for controlling unwanted microorganisms comprising at least one of the compounds of the formula (I) and one or more inert carrier. The inert carrier further comprises agriculturally suitable auxiliaries, solvents, diluents, surfactants and/or extenders and the like.

The present invention further relates to a composition for controlling unwanted microorganisms, comprising at least one of the compounds of the formula (I) and/or one or more active compatible compound selected from fungicides, bactericides, acaricides, insecticides, nematicides, herbicides, biopesticides, plant growth regulators, antibiotics, fertilizers and/or mixtures thereof.

The present invention also relates to a method for controlling unwanted microorganisms, wherein compounds of the formula (I) are applied to the microorganisms and/or in their habitat.

The present invention further provides a method for protecting seed against unwanted microorganisms by using seed treated with at least one compound of the formula (I).

The compounds of the formula (I) can possess potent microbicidal activity and can be used for the control of unwanted microorganisms, such as fungi, nematodes and bacteria, in crop protection and in the protection of such materials.

The compounds of the formula (I) can possess very good fungicidal properties and can be used in crop protection, for example for control of Plasmodiophoromycetes, Oomycetes, Chytridiomyceles, Zygomycetes, Ascomyceles, Basidiomycetes and Deuteromycetes.

The compounds of the formula (I) can be used as nematicides in crop protection, for example, for control of Rhabditida, Dorylaimida, and Tryplonchida.

The compounds of the formula (I) can be used as insecticides in crop protection, for example, for control of *Lepidoptera, Coleoptera, Hemiptera, Homoplera, Thysanoptera, Diptera, Orthoptera & Isoptera.*

The compounds of the formula (I) can be used as acaricides in crop protection, for example, for control of Eriophyoidea, Tetranychoidea, Eupodoidea and Tarsonemidae.

The compounds of the formula (I) can be used as bactericides in crop protection, for example, for control of Pseudomonadaceae, Rhizobiaceae, Enterobacteriaceae, Corynebacteriaceae and *Streptomycelaceae.*

The compounds of the formula (I) can be used as herbicides and can be effective against a broad spectrum of economically important mono- and dicotyledonous harmful plants. Monocotyledonous broad-leaved weed species may include *Avena, Lolium, Alopecurus, Phalaris, Echinochloa, Digitaria, Setaria* and *Cyperus* species from the annual group and perennial species *Agropyron, Cynodon, Imperata* and *Sorghum* and also perennial *Cyperus* species. Dicotyledonous broad-leaved weed species may include *Galium, Viola, Veronica, Lamium, Stellaria, Amaranthus, Sinapis, Ipomoea, Sida, Matricaria* and *Abutilon* on the annual side, and also *Convolvulus, Cirsium, Rumex* and *Artemisia* in the case of the perennial broad-leaved weeds. Harmful plants that occur in rice, such as, for example, *Echinochloa, Sagittaria, Alisma, Eleocharis, Scirpus* and *Cyperus*, can be controlled by the compounds of formula (I).

The compounds of the formula (I) can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

According to the invention, as defined above a carrier is a natural or synthetic, organic or inorganic substance with which the active ingredients are mixed or combined for better applicability, in particular for application to plants or plant parts or seed. The carrier, which may be solid or liquid, are generally inert and should be suitable for use in agriculture.

Useful solid carriers include for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or —POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally, suitables are oligo- or polymers, for example those derived from vinylic monomers, from acrylic acid, from EO and/or PO alone or in combination with, for example, (poly) alcohols or (poly) amines. It is also possible to use lignin and its sulphonic acid derivatives, unmodified and modified celluloses, aromatic and/or aliphatic sulphonic acids and also their adduct with formaldehyde.

The active ingredients can be applied as such or converted to the customary formulations or in the form of their formulations or the use forms prepared therefrom, such as ready-to-use solutions, emulsions, water or oil-based suspensions, powders, wettable powders, pastes, soluble powders, soluble tablets, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, nursery boxes, broadcasting, dusting, foaming, spreading-on and the like. It is also possible to deploy the active ingredients by the ultra-low volume method or to inject the active ingredient preparation or the active ingredient itself into the soil. It is also possible to treat the seed of the plants.

The active ingredients can be further converted to the nanoformulation with intent to further improve water solubility, thermal stability, bioavailability, sensory attributes, and physiological performance.

Furthermore, the choice of the type of formulation will depend on the specific use.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly) ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral, vegetable oils and methylated seed oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compounds of the formula (I) may additionally comprise further components, for example surfactants. Suitable surfactants are emulsifiers and/or foam formers, dispersants or wetting agents having ionic or non-ionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

The invention also relates to agrochemical compositions comprising an auxiliary and at least one compound of formula (I) according to the invention.

An agrochemical composition comprises a fungicidally effective amount of a compound of formula (I). The term "effective amount" denotes an amount of the composition or of the compounds of formula (I), which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound of formula (I) used.

The compounds of formula (I), their oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e. g. BR, TB, DT), granules (e. g. WG, SG, GR, FG, GG, MG), insecticidal articles (e.g. LN), as well as gel formulations for the treatment of plant propagation materials such as seeds (e. g. GF). These and further compositions types are defined in the "Catalogue of pesticide formulation types and international coding system", Technical Monograph No. 2, 61h Ed. May 2008, Croplife International.

The compositions are prepared in a known manner, such as described by Mollet and Grube mann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity them selves, and which improve the biological performance of the compound of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin. Suitable anti-foaming agents are silicones, long chain alcohols, and salts of fatty acids. Suitable colorants (e. g. in red, blue, or green) are pigments of low water solubility and watersoluble dyes. Examples are inorganic colorants (e. g. iron oxide, titan oxide, iron hexacyanoferrate) and organic colorants (e.g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-soluble concentrates (SL, LS)
10-60 wt % of a compound of formula (I) and 5-15 wt % wetting agent (e.g. alcohol alkoxylates) are dissolved in water and/or in a water-soluble solvent (e. g. alcohols) ad 100 wt %. The active substance dissolves upon dilution with water.

ii) Dispersible concentrates (DC) 5-25 wt % of a compound of formula (I) and 1-10 wt % dispersant (e.g. polyvinyl pyrrolidone) are dissolved in organic solvent (e. g. cyclohexanone) ad 100 wt %. Dilution with water gives a dispersion.

iii) Emulsifiable concentrates (EC) 15-70 wt % of a compound of formula (I) and 5-10 wt % emulsifiers (e. g. calcium dodecylbenzenesulfonate and castor oil ethoxylate) are dissolved in water-insoluble organic solvent (e. g. aromatic hydro carbon) ad 100 wt %. Dilution with water gives an emulsion.

iv) Emulsions (EW, EO, ES)
5-40 wt % of a compound of formula (I) and 1-10 wt % emulsifiers (e. g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)
In an agitated ball mill, 20-60 wt % of a compound of formula (I) are comminuted with addition of 2-10 wt % dispersants and wetting agents (e. g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-dispersible granules and water-soluble granules (WG, SG)

50-80 wt % of a compound of formula (I) are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of a compound of formula (I) are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound of formula (I) are comminuted with addition of 3-10 wt % dispersants (e.g. sodium lignosulfonate), 1-5 wt % thickener (e.g. carboxymethyl cellulose) and water ad 100 wt % to give a fine suspension of the active substance. Dilution with water gives a stable suspension of the active substance.

ix) Microemulsion (ME)

5-20 wt % of a compound of formula (I) are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound of formula (I), 0-40 wt % water insoluble organic solvent (e.g. aromatic hydrocarbon), 2-15 wt % acrylic monomers (e.g. methylmethacrylate, methacrylic acid and a di- or tri-acrylate) are dispersed into an aqueous solution of a protective colloid (e.g. polyvinyl alcohol). Radical polymerization results in the formation of poly(meth)acrylate microcapsules. Alternatively, an oil phase comprising 5-50 wt % of a compound of formula (I) according to the invention, 0-40 wt % water insoluble organic solvent (e. g. aromatic hydrocarbon), and an isocyanate monomer (e.g. diphenylmethene-4,4'-diisocyanatae) are dispersed into an aqueous solution of a protective colloid (e. g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable powders (DP, DS)

1-10 wt % of a compound of formula (I) is ground finely and mixed intimately with solid carrier (e.g. finely divided kaolin) ad 100 wt %.

xii) Granules (GR, FG)

0.5-30 wt % of a compound of formula (I) is ground finely and associated with solid carrier (e. g. silicate) ad 100 wt %. Granulation is achieved by extrusion, spray-drying or fluidized bed.

xiii) Ultra-low volume liquids (UL)

1-50 wt % of a compound of formula (I) are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance.

The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound of formula (I) and compositions thereof, respectively, onto plant propagation material, especially seeds, include dressing, coating, pelleting, dusting, and soaking as well as in-furrow application methods. Preferably, compound of formula (I) or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions ac cording to the invention in a weight ratio of 1:100 to 100:1, preferably 1:10 to 10:1.

A pesticide is generally a chemical or biological agent (such as pesticidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease.

The term pesticides includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology to increase plant growth, biomass, yield or any other quality parameter of the harvestable goods of a crop plant.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides are typically created by growing and concentrating naturally occurring organisms and/or their metabolites including bacteria and other microbes, fungi, viruses, nematodes, proteins, etc. They are often considered to be important components of integrated pest management (IPM) programs.

Biopesticides fall into two major classes, microbial and biochemical pesticides:

1. Microbial pesticides consist of bacteria, fungi or viruses (and often include the metabolites that bacteria and fungi produce). entomopathogenic nematodes are also classed as microbial pesticides, even though they are multicellular.

2. Biochemical pesticides are naturally occurring substances that control pests or provide other crop protection uses as defined below, but are relatively non-toxic to mammals The user applies the composition according to the invention usually from a pre dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

The present invention further relates to a composition for controlling unwanted microorganisms comprising at least one of the compounds of the formula (I) and one or more inert carrier. The inert carrier further comprises agriculturally suitable auxiliaries, solvents, diluents, surfactants and/or extenders and the like.

The present invention further relates to a composition for controlling unwanted microorganisms, comprising at least one of the compounds of the formula (I) and/or one or more active compatible compound selected from fungicides, bactericides, acaricides, insecticides, nematicides, herbicides, biopesticides, plant growth regulators, antibiotics, fertilizers and/or mixtures thereof.

Generally, a compound of the present invention is used in the form of a composition (e.g. formulation) containing a carrier. A compound of the invention and compositions thereof can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra-low volume (ulv) liquid, ultra-low volume (ulv) suspension, water dispersible granules or tablets, water dispersible powder for slurry treatment, water soluble granules or tablets, water soluble powder for seed treatment and wettable powder.

A formulation typically comprises a liquid or solid carrier and optionally one or more customary formulation auxiliaries, which may be solid or liquid auxiliaries, for example unepoxidized or epoxidized vegetable oils (for example epoxidized coconut oil, rapeseed oil or soya oil), antifoams, for example silicone oil, preservatives, clays, inorganic compounds, viscosity regulators, surfactant, binders and/or tackifiers. The composition may also further comprise a fertilizer, a micronutrient donor or other preparations which influence the growth of plants as well as comprising a combination containing the compound of the invention with one or more other biologically active agents, such as bactericides, fungicides, nematicides, plant activators, acaricides, and insecticides.

Accordingly, the present invention also makes available a composition comprising a compound of the invention and an agronomical carrier and optionally one or more customary formulation auxiliaries. The compositions are prepared in a manner known per se, in the absence of auxiliaries for example by grinding, screening and/or compressing a solid compound of the present invention and in the presence of at least one auxiliary for example by intimately mixing and/or grinding the compound of the present invention with the auxiliary (auxiliaries). In the case of solid compounds of the invention, the grinding/milling of the compounds is to ensure specific particle size. These processes for the preparation of the compositions and the use of the compounds of the invention for the preparation of these compositions are also a subject of the invention.

As a rule, the compositions comprise 0.1 to 99%, especially 0.1 to 95%, of compound according to the present invention and 1 to 99.9%, especially 5 to 99.9%, of at least one solid or liquid carrier, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Examples of foliar formulation types for pre-mix compositions are:

| | |
|---|---|
| GR: Granules | EW: emulsions, oil in water |
| WP: wettable powders | ME: micro-emulsion |
| WG: water dispersable granules (powders) | SC: aqueous suspension concentrate |
| SG: water soluble granules | CS: aqueous capsule suspension |
| SL: soluble concentrates | OD: oil-based suspension concentrate, and |
| EC: emulsifiable concentrate | SE: aqueous suspo-emulsion. |

Whereas, examples of seed treatment formulation types for pre-mix compositions are:

| | |
|---|---|
| WS: wettable powders for seed treatment slurry | FS: Suspension concentrates for seed treatment |
| LS: solution for seed treatment | WG: water dispersible granules, and |
| ES: emulsions for seed treatment | CS: aqueous capsule suspension. |

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries. Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation. Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be pre sized before coating. After coating, the seeds are typically dried and then transferred to a sizing machine for sizing. Such procedures are known in the art. The compounds of the present invention are particularly suited for use in soil and seed treatment applications.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

A compound of the formula (I) in a preferred embodiment, independent of any other embodiments, is in the form of a plant propagation material treating (or protecting) composition, wherein said plant propagation material protecting composition may comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

Examples of application methods for the compounds of the invention and compositions thereof, that is the methods of controlling pests in the agriculture, are spraying, atomizing, dusting, brushing on, dressing, scattering or pouring which are to be selected to suit the intended aims of the prevailing circumstances.

One method of application in agriculture is application to the foliage of the plants (foliar application), it being possible to select frequency and rate of application to match the danger of infestation with the pest or fungi in question. Alternatively, the active ingredient can reach the plants via the root system (systemic action), by applying the compound to the locus of the plants, for example by application of a liquid composition of the compound into the soil (by drenching), or by applying a solid form of the compound in the form of granules to the soil (soil application). In the case of paddy rice plants, such granules can be metered into the flooded paddy-field. The application of the compounds of the present invention to the soil is a preferred application method.

Typical rates of application per hectare is generally 1 to 2000 g of active ingredient per hectare, in particular 10 to 1000 g/ha, preferably 10 to 600 g/ha, such as 50 to 300 g/ha.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70% by weight.

The formulations described above can be used for controlling unwanted microorganisms, in which the compositions comprising compounds of the formula (I) are applied to the microorganisms and/or in their habitat.

Compounds of the formula (I) according to this invention, as well as salts, N-oxides, metal complexes, stereoisomers or polymorphs can be used as such or in formulations thereof and can be mixed with known mixing partners in order to broaden, for example, the activity spectrum or to prevent development of resistance. Useful mixing partners include, for example, known fungicides, insecticides, acaricides, nematicides, biopesticides and bactericides. A mixture with other known active ingredients, such as herbicides, or with fertilizers and growth regulators, safeners and/or semiochemicals, is also possible.

Examples for such chemical ingredients are given herein in a not limiting way. Some of them are specified herein by their common names that are known and described, for example in *The Pesticide Manual* 17th Ed., or can be searched in the internet (e.g. under www.alanwood.net/pesticides). Others are described by their systematic name following the IUPAC rules for nomenclature.

All named mixing partners of the classes (A) to (O) as described below can, if their functional groups enable this, optionally form salts with suitable bases or acids appear as stereoisomers, even if not specifically mentioned in each case, or as polymorphs. They are also understood as being included herein.

These examples are

A) Inhibitors of the ergosterol biosynthesis, for example (A01) aldimorph, (A02) azaconazole, (A03) bitertanol, (A04) bromuconazole, (A05) cyproconazole, (A06) diclobutrazole, (A07) difenoconazole, (A08) diniconazole, (A09) diniconazole-M, (A10) dodemorph, (A11) dodemorph acetate, (A12) epoxiconazole, (A13) etaconazole, (A14) fenarimol, (A15) fenbuconazole, (A16) fenhexamid, (A17) fenpropidin, (A18) fenpropimorph, (A19) fluquinconazole, (A20) flurprimidol, (A21) flusilazole, (A22) flutriafol, (A23) furconazole, (A24) furconazole-cis, (A25) hexaconazole, (A26) imazalil, (A27) imazalil sulfate, (A28) imibenconazole, (A29) ipconazole, (A30) metconazole, (A31) myclobutanil, (A32) naftifine, (A33) nuarimol, (A34) oxpoconazole, (A35) paclobutrazol, (A36) pefiirazoate, (A37) penconazole, (A38) piperalin, (A39) prochloraz, (A40) propiconazole, (A41) prothioconazole, (A42) pyributicarb, (A43) pyrifenox, (A44) quinconazole, (A45) simeconazole, (A46) spiroxamine, (A47) tebuconazole, (A48) terbinafine, (A49) tetraconazole, (A50) triadimefon, (A51) triadimenol, (A52) tridemorph, (A53) triflumizole, (A54) triforine, (A55) triticonazole, (A56) uniconazole, (A57) uniconazole-p, (A58) viniconazole, (A59) voriconazole, (A60) 1-(4-chlorophenyl)-2-(1H-1,2,4-triazol-1-yl)cycloheptanol, (A61) methyl 1-(2,2-dimethyl-2,3-dihydro-1H-inden-1-yl)-H-imidazole-5-carboxylate, (A62) N'-{5-(difluoromethyl)-2-methyl-4-[3-(trimethylsilyl) propoxy]phenyl}-N-ethyl-N-methylimidoformamide, (A63) N-ethyl-N-methyl-N'-{2-methyl-5-(trifluoromethyl)-4-[3-(trimethylsilyl)propoxy]phenyl}imidoformamide, (A64) O-[1-(4-methoxyphenoxy)-3,3-dimethylbutan-2-yl]-1H-imidazole-1-carbothioate, (A65) Pyrisoxazole, (A66) 2-{[3-(2-chlorophenyl)-2-(2,4-difluorophenyl)oxiran-2-yl]methyl}-2,4-dihydro-3H-1,2,4-triazole-3-thione, (A67) 1-{[3-(2-chlorophenyl)-2-(2,4-difluorophenyl)oxiran-2-yl]methyl}-1H-1,2,4-triazol-5-yl thiocyanate, (A68) 5-(allylsulfanyl)-1-{[3-(2-chlorophenyl)-2-(2,4-difluorophenyl) oxiran-2-yl]methyl}-1H-1,2,4-triazole, (A69) 2-[1-(2,4-dichlorophenyl)-5-hydroxy-2,6,6-trimethylheptan-4-yl]-2,4-dihydro-3H-1,2,4-triazole-3-thione, (A70) 2-{[rel(2R,3S)-3-(2-chlorophenyl)-2-(2,4-difluorophenyl) oxiran-2-yl]methyl}-2,4-dihydro-3H-1,2,4-triazole-3-thione, (A71) 2-{[rel(2R,3R)-3-(2-chlorophenyl)-2-(2,4-difluorophenyl)oxiran-2-yl]methyl}-2,4-dihydro-3H-1,2,4-triazole-3-thione, (A72) 1-{[rel(2R,3S)-3-(2-chlorophenyl)-2-(2,4-difluorophenyl)oxiran-2-yl]methyl}-1H-1,2,4-triazol-5-yl thiocyanate, (A73) 1-{[rel(2R,3R)-3-(2-chlorophenyl)-2-(2,4-difluorophenyl)oxiran-2-yl]methyl}-1H-1,2,4-triazol-5-yl thiocyanate, (A74) 5-(allylsulfanyl)-1-{[rel(2R,3S)-3-(2-chlorophenyl)-2-(2,4-difluorophenyl)oxiran-2-yl]methyl}-1H-1,2,4-triazole, (A75) 5-(allylsulfanyl)-1-{[rel(2R,3R)-3-(2-chlorophenyl)-2-(2,4-difluorophenyl) oxiran-2-yl]methyl}-1H-1,2,4-triazole, (A76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (A77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (A78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (A79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (A80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (A81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (A82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (A83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (A84) 2-[4-(4-chlorophenoxy)-2-(trifluoromethyl)phenyl]-1-(1H-1,2,4-triazol-1-yl)propan-2-ol, (A85) 2-[4-(4-chlorophenoxy)-2-(trifluoromethyl)phenyl]-1-(1H-1,2,4-triazol-1-yl)butan-2-ol, (A86) 2-[4-(4-chlorophenoxy)-2-(trifluoromethyl)phenyl]-1-(1H-1,2,4-triazol-1-yl)pentan-2-ol, (A87) 2-[2-chloro-4-(4-chlorophenoxy)phenyl]-1-(1H-1,2,4-triazol-1-yl)butan-2-ol, (A88) 2-[2-chloro-4-(2,4-dichlorophenoxy)phenyl]-1-(1H-1,2,4-triazol-1-yl)propan-2-ol, (A89) (2R)-2-(1-chlorocyclopropyl)-4-[(1R)-2,2-dichlorocyclopropyl]-1-(1H-1,2,4-triazol-1-yl)butan-2-ol, (A90) (2R)-2-(1-chlorocyclopropyl)-4-[(1S)-2,2-dichlorocyclopropyl]-1-(1H-1,2,4-triazol-1-yl)butan-2-ol, (A91) (2S)-2-(1-chlorocyclopropyl)-4-[(I S)-2,2-dichlorocyclopropyl]-1-(1H-1,2,4-triazol-1-yl)butan-2-ol, (A92) (2S)-2-(1-chlorocyclopropyl)-4-[(1R)-2,2-dichlorocyclopropyl]-1-(1H-1,2,4-triazol-1-yl)butan-2-ol, (A93) (1S,2R,5R)-5-(4-chlorobenzyl)-2-(chloromethyl)-2-methyl-1-(1H-1,2,4-triazol-1-ylmethyl)cyclopentanol, (A94) (1R,2S,5S)-5-(4-chlorobenzyl)-2-(chloromethyl)-2-methyl-1-(1H-1,2,4-triazol-1-ylmethyl)cyclopentanol, (A95) 5-(4-chlorobenzyl)-2-(chloromethyl)-2-methyl-1-(1H-1,2,4-triazol-1-ylmethyl)cyclopentanol, Other Sterol biosynthesis inhibitors: (A96) chlorphenomizole, (A97) Mefentriflucona-zole.

B) Inhibitors of the respiratory chain at complex I or II, for example (B01) bixafen, (B02) boscalid, (B03) carboxin, (B04) cypropamide, (B05) diflumetorim, (B06) fenfuram, (B07) fluopyram, (B08) flutolanil, (B09) fluxapyroxad, (B10) furametpyr, (B11) furmecyclox, (B12) isopyrazam (mixture of syn-epimeric racemate 1RS,4SR,9RS and anti-epimeric racemate 1RS,4SR,9SR), (B13) isopyrazam (anti-epimeric racemate 1RS,4SR,9SR), (B14) isopyrazam (anti-epimeric enantiomer 1R,4S,9S), (B15) isopyrazam (anti-epimeric enantiomer 1S,4R,9R), (B16) isopyrazam (syn-epimeric racemate 1RS,4SR,9RS), (B17) isopyrazam (syn-epimeric enantiomer 1R,4S,9R), (B18) isopyrazam (syn-epimeric enantiomer 1S,4R,9S), (B19) mepronil, (B20) oxycarboxin, (B21) penflufen, (B22) penthiopyrad, (B23) pydiflumetofen, (B24) sedaxane, (B25) thifluzamide, (B26) 1-methyl-N-[2-(1,1,2,2-tetrafluoroethoxy)phenyl]-3-(trifluoromethyl)-1H-pyrazole-4-carboxamide, (B27) 3-(difluoromethyl)-1-methyl-N-[2-(1,1,2,2-tetrafluoroethoxy)phenyl]-H-pyrazole-4-carboxamide, (B28) 3-(difluoromethyl)-N-[4-fluoro-2-(1,1,2,3,3,3-hexafluoropropoxy)phenyl]-1-methyl-1H-pyrazole-4-carboxamide, (B29) N-[1-(2,4-dichlorophenyl)-1-methoxypropan-2-yl]-3-(difluoromethyl)-1-methyl-1H-pyrazole-4-carboxamide, (B30) 5,8-difluoro-N-[2-(2-fluoro-4-{[4-(trifluoromethyl)pyridin-2-yl]oxy}phenyl)ethyl]quinazolin-4-amine, (B31) benzovindiflupyr, (B32) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (B33) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (B34) 3-(difluoromethyl)-1-methyl-N-(1,1,3-trimethyl-2,3-dihydro-1H-inden-4-yl)-1H-pyrazole-4-carboxamide, (B35) 1,3,5-trimethyl-N-(1,1,3-trimethyl-2,3-dihydro-1H-inden-4-yl)-1H-pyrazole-4-carboxamide, (B36) I-methyl-3-(trifluoromethyl)-N-(1,1,3-trimethyl-2,3-dihydro-1H-inden-4-yl)-1H-pyrazole-4-carboxamide, (B37) 1-methyl-3-(trifluoromethyl)-N-[(3R)-1,1,3-trimethyl-2,3-dihydro-1H-inden-4-yl]-1H-pyrazole-4-carboxamide, (B38) 1-methyl-3-(trifluoromethyl)-N-[(3S)-1,1,3-trimethyl-2,3-dihydro-1H-inden-4-yl]-1H-pyrazole-4-carboxamide, (B39) 3-(difluoromethyl)-1-methyl-N-[(3S)-1,1,3-trimethyl-2,3-dihydro-1H-inden-4-yl]-1H-pyrazole-4-carboxamide, (B40) 3-(difluoromethyl)-1-methyl-N-[(3R)-1,1,3-trimethyl-2,3-dihydro-1H-inden-4-yl]-1H-pyrazole-4-carboxamide, (B41) 1,3,5-trimethyl-N-[(3R)-1,1,3-trimethyl-2,3-dihydro-1H-inden-4-yl]-H-pyrazole-4-carboxamide, (B42) 1,3,5-trimethyl-N-[(3S)-1,1,3-trimethyl-2,3-dihydro-1H-inden-4-yl]-1H-pyrazole-4-carboxamide, (B43) benodanil, (B44) 2-chloro-N-(1,1,3-trimethyl-2,3-dihydro-1H-inden-4-yl)pyridine-3-carboxamide, (B45) Isofetamid, (B46) I-methyl-3-(trifluoromethyl)-N-[2'-(trifluoromethyl)biphenyl-2-yl]-1H-pyrazole-4-carboxamide, (B47) N-(4'-chlorobiphenyl-2-yl)-3-(difluoromethyl)-1-methyl-H-pyrazole-4-carboxamide, (B48) N-(2',4'-dichlorobiphenyl-2-yl)-3-(difluoromethyl)-1-methyl-H-pyrazole-4-carboxamide, (B49) 3-(difluoromethyl)-1-methyl-N-[4'-(trifluoromethyl)biphenyl-2-yl]-H-pyrazole-4-carboxamide, (B50) N-(2',5'-difluorobiphenyl-2-yl)-1-methyl-3-(trifluoromethyl)-H-pyrazole-4-carboxamide, (B51) 3-(difluoromethyl)-1-methyl-N-[4'-(prop-1-yn-1-yl)biphenyl-2-yl]-1H-pyrazole-4-carboxamide, (B52) 5-fluoro-1,3-dimethyl-N-[4'-(prop-1-yn-1-yl)biphenyl-2-yl]-1H-pyrazole-4-carboxamide, (B53) 2-chloro-N-[4'-(prop-1-yn-1-yl)biphenyl-2-yl]nicotinamide, (B54) 3-(difluoromethyl)-N-[4'-(3,3-dimethylbut-1-yn-1-yl)biphenyl-2-yl]-1-methyl-H-pyrazole-4-carboxamide, (B55) N-[4'-(3,3-dimethylbut-1-yn-1-yl)biphenyl-2-yl]-5-fluoro-1,3-dimethyl-1H-pyrazole-4-carboxamide, (B56) 3-(difluoromethyl)-N-(4'-ethynylbiphenyl-2-yl)-1-methyl-1H-pyrazole-4-carboxamide, (B57) N-(4'-ethynylbiphenyl-2-yl)-5-fluoro-1,3-dimethyl-1H-pyrazole-4-carboxamide, (B58) 2-chloro-N-(4'-ethynylbiphenyl-2-yl)nicotinamide, (B59) 2-chloro-N-[4'-(3,3-dimethylbut-1-yn-1-yl)biphenyl-2-yl]nicotinamide, (B60) 4-(difluoromethyl)-2-methyl-N-[4'-(trifluoromethyl)biphenyl-2-yl]-1,3-thiazole-5-carboxamide, (B61) 5-fluoro-N-[4'-(3-hydroxy-3-methylbut-1-yn-1-yl)biphenyl-2-yl]-1,3-dimethyl-1H-pyrazole-4-carboxamide, (B62) 2-chloro-N-[4'-(3-hydroxy-3-methylbut-1-yn-1-yl)biphenyl-2-yl]nicotinamide, (B63) 3-(difluoromethyl)-N-[4'-(3-methoxy-3-methylbut-1-yn-1-yl)biphenyl-2-yl]-1-methyl-1H-pyrazole-4-carboxamide, (B64) 5-fluoro-N-[4'-(3-methoxy-3-methylbut-1-yn-1-yl)biphenyl-2-yl]-1,3-dimethyl-H-pyrazole-4-carboxamide, (B65) 2-chloro-N-[4'-(3-methoxy-3-methylbut-1-yn-1-yl)biphenyl-2-yl]nicotinamide, (B66) 1,3-dimethyl-N-(1,1,3-trimethyl-2,3-dihydro-1H-inden-4-yl)-H-pyrazole-4-carboxamide, (B67) 1,3-dimethyl-N-[(3R)-1,1,3-trimethyl-2,3-dihydro-1H-inden-4-yl]-1H-pyrazole-4-carboxamide, (B68) 1,3-dimethyl-N-[(3S)-1,1,3-trimethyl-2,3-dihydro-1H-inden-4-yl]-1H-pyrazole-4-carboxamide, (B69) 3-(difluoromethyl)-N-methoxy-1-methyl-N-[1-(2,4,6-trichlorophenyl)propan-2-yl]-1H-pyrazole-4-carboxamide, (170) 3-(difluoromethyl)-N-(7-fluoro-1,1,3-trimethyl-2,3-dihydro-1H-inden-4-yl)-1-methyl-1H-pyrazole-4-carboxamide, (B71) 3-(difluoromethyl)-N-[(3,R)-7-fluoro-1,1,3-trimethyl-2,3-dihydro-1H-inden-4-yl]-1-methyl-1H-pyrazole-4-carboxamide, (B72) 3-(difluoromethyl)-N-[(3S)-7-fluoro-1,1,3-trimethyl-2,3-dihydro-1H-inden-4-yl]-1-methyl-H-pyrazole-4-carboxamide.

C) Inhibitors of the respiratory chain at complex III, for example (C01) ametoctradin, (C02) amisulbrom, (C03) azoxystrobin, (C04) cyazofamid, (C05) coumethoxystrobin, (C06) coumoxystrobin, (C07) dimoxystrobin, (C08) enoxastrobin, (C09) famoxadone, (C10) fenamidone, (C11) fenaminstrobin, (C12) flufenoxystrobin, (C13) fluoxastrobin, (C14) kresoxim-methyl, (C15) metominostrobin, (C16) mandestrobin, (C17) orysastrobin, (C18) picoxystrobin, (C19) pyraclostrobin, (C20) pyrametostrobin, (C21) pyraoxystrobin, (C22) pyribencarb, (C23) triclopyricarb, (C24) trifloxystrobin, (C25) (2E)-2-(2-{[6-(3-chloro-2-methylphenoxy)-5-fluoropyrimidin-4-yl]oxy}phenyl)-2-(methoxyimino)-N-methylacetamide, (C26) (2E)-2-(methoxyimino)-N-methyl-2-(2-{[({(1E)-1-[3-(trifluoromethyl)phenyl]ethylidene}amino)oxy]methyl}phenyl) acetamide, (C27) (2E)-2-(methoxyimino)-N-methyl-2-{2-[(E)-({1-[3-(trifluoromethyl)phenyl]ethoxy}imino)methyl]phenyl}acetamide, (C28)(2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (C29) Fenaminostrobin, (C30) 5-methoxy-2-methyl-4-(2-{[({(E)-1-[3-(trifluoromethyl)phenyl]ethylidene}amino)oxy]methyl}phenyl)-2,4-dihydro-3H-1,2,4-triazol-3-one, (C31) methyl (2E)-2-{2-[({cyclopropyl[(4-methoxyphenyl)imino]methyl}sulfanyl)methyl]phenyl}-3-methoxyacrylate, (C32) N-(3-ethyl-3,5,5-trimethylcyclohexyl)-3-formamido-2-hydroxybenzamide, (C33) 2-{2-[(2,5-dimethylphenoxy)methyl]phenyl}-2-methoxy-N-methylacetamide, (C34) 2-{2-[(2,5-dimethylphenoxy)methyl]phenyl}-2-methoxy-N-methylacetamide, (C35) (2E,3Z)-5-{[1-(4-chlorophenyl)-1H-pyrazol-3-yl]oxy}-2-(methoxyimino)-N,3-dimethylpent-3-enamide.

D) Inhibitors of the mitosis and cell division, for example (D01) benomyl, (D02) carbendazim, (D03) chlorfenazole, (D04) diethofencarb, (D05) ethaboxam, (D06) fluopicolide, (D07) fiiberidazole, (D08) pencycuron, (D09) thiabendazole, (D10) thiophanate-methyl, (D11) thiophanate, (D12) zoxamide, (D13) 5-chloro-7-(4-methylpiperidin-1-yl)-6-(2,4,6-trifluorophenyl)[1,2,4]triazolo[1,5-a]pyrimidine, (D14) 3-chloro-5-(6-chloropyridin-3-yl)-6-methyl-4-(2,4,6-trifluorophenyl) pyridazine, (D5) 3-chloro-4-(2,6-difluorophenyl)-6-methyl-5-phenyl-pyridazine, (D16) 3-chloro-6-methyl-5-phenyl-4-(2,4,6-trifluorophenyl)pyridazine, (D17) N-ethyl-2-[(3-thynyl-8-methyl-6-quinolyl)oxy]butanamide, (D18) N-ethyl-2-[(3-ethynyl-8-methyl-6-quinolyl)oxy]-2-methylsulfanyl-acetamide, (D19) 2-[(3-ethynyl-8-methyl-6-quinolyl)oxy]-N-(2-fluoroethyl)butanamide, (D20) 2-[(3-ethynyl-8-methyl-6-quinolyl)oxy]-N-(2-fluoroethyl)-2-methoxy-acetamide, (D21) 2-[(3-ethynyl-8-methyl-6-quinolyl)oxy]-N-propyl-butanamide, (D22) 2-[(3-ethynyl-8-methyl-6-quinolyl)oxy]-2-methoxy-N-propyl-acetamide, (D23) 2-[(3-ethynyl-8-methyl-6-quinolyl)oxy]-2-methylsulfanyl-N-propyl-acetamide, (D24) 2-[(3-ethynyl-8-methyl-6-quinolyl)oxy]-N-(2-fluoroethyl)-2-methylsulfanyl-acetamide, (D16) 4-(2-bromo-4-fluoro-phenyl)-N-(2-chloro-6-fluoro-phenyl)-2,5-dimethyl-pyrazol-3-amine, (D17) Aminopyrazole;

E) Compounds capable to have a multisite action, for example (E01) bordeaux mixture, (E02) captafol, (E03) captan, (E04) chlorothalonil, (E05) copper hydroxide, (E06) copper naphthenate, (E07) copper oxide, (E08) copper oxychloride, (E09) copper (2+) sulfate, (E10) dichlofluanid, (E11) dithianon, (E12) dodine, (E13) dodine free base, (E14) ferbam, (E15) fluorofolpet, (E16) folpet, (E17) guazatine, (E18) guazatine acetate, (E19) iminoctadine, (E20) iminoctadine albesilate, (E21) iminoctadine triacetate, (E22) mancopper, (E23) mancozeb, (E24) maneb, (E25) metiram, (E26) metiram zinc, (E27) oxine-copper, (E28) propamidine, (E29) propineb, (E30) sulfur and sulfur preparations including calcium polysulfide, (E31) thiram, (E32) tolylfluanid, (E33) zineb, (E34) ziram, (E35) anilazine, (E36) dipymetitrone.

F) Compounds capable to induce a host defence, for example (F01) acibenzolar-S-methyl, (F02) isotianil, (F03) probenazole, (F04) tiadinil, (F05) laminarin, (F06) 4-cyclopropyl-N-(2,4-dimethoxyphenyl)thiadiazole-5-carboxamide.

G) Inhibitors of the amino acid and/or protein biosynthesis, for example (G01) andoprim, (G02) blasticidin-S, (G03) cyprodinil, (G04) kasugamycin, (G05) kasugamycin hydrochloride hydrate, (G06) mepanipyrim, (G07) pyrimethanil, (G08) 3-(5-fluoro-3,3,4,4-tetramethyl-3,4-dihydroisoquinolin-1-yl)quinoline, (G09)oxytetracycline, (G10) streptomycin.

H) Inhibitors of the ATP production, for example (H01) fentin acetate, (H02) fentin chloride, (H03) fentinhydroxide, (1-104) silthiofam.

I) Inhibitors of the cell wall synthesis, for example (I01) benthiavalicarb, (I02) dimethomorph, (I03) flumorph, (I04) iprovalicarb, (I05) mandipropamid, (I06) polyoxins, (I07) polyoxorim, (I08) validamycin A, (I09) valifenalate, (I10) polyoxin B, (I1) (2E)-3-(4-tert-butylphenyl)-3-(2-chloropyridin-4-yl)-1-(morpholin-4-yl)prop-2-en-1-one, (I12) (2Z)-3-(4-tert-butylphenyl)-3-(2-chloropyridin-4-yl)-1-(morpholin-4-yl)prop-2-en-1-one.

J) Inhibitors of the lipid and membrane synthesis, for example (J01) biphenyl, (J02) chloroneb, (J03) dicloran, (J04) edifenphos, (J05) etridiazole, (J06) iodocarb, (J07) iprobenfos, (J08) isoprothiolane, (J09) propamocarb, (J10) propamocarb hydrochloride, (J11) prothiocarb, (J12) pyrazophos, (J13) quintozene, (J14) tecnazene, (J15) toclofosmethyl.

K) Inhibitors of the melanin biosynthesis, for example (KO 1) carpropamid, (K02) diclocymet, (K03) fenoxanil, (K04) phthalide, (K05) pyroquilon, (K06) tolprocarb, (K07) tricyclazole.

L) Inhibitors of the nucleic acid synthesis, for example (L01) benalaxyl, (L02) benalaxyl-M (kiralaxyl), (L03) bupirimate, (L04) clozylacon, (L05) dimethirimol, (L06) ethirimol, (L07) furalaxyl, (L08) hymexazol, (L09) metalaxyl, (L10) metalaxyl-M (mefenoxam), (L11) ofurace, (L12) oxadixyl, (L13) oxolinic acid, (L14)octhilinone.

M) Inhibitors of the signal transduction, for example (M01) chlozolinate, (M02) fenpiclonil, (M03) fludioxonil, (M04) iprodione, (M05) procymidone, (M06) quinoxyfen, (M07) vinclozolin, (M08) proquinazid.

N) Compounds capable to act as an uncoupler, for example (N01) binapacryl, (NO₂) dinocap, (N03) ferimzone, (N04) fluazinam, (N05) meptyldinocap.

Further compounds, for example (O01) benthiazole, (O02) bethoxazin, (O03) capsimycin, (O04) carvone, (O05) chinomethionat, (O06) pyriofenone (chlazafenone), (O07) cufraneb, (O08) cyflufenamid, (O09) cymoxanil, (O10) cyprosulfamide, (O11) dazomet, (O12) debacarb, (O13) dichlorophen, (O14) dichlobentiazox, (O15) diclomezine, (O16) difenzoquat, (O17) difenzoquat metilsulfate, (O18) diphenylamine, (O19) ecomate, (O20) fenpyrazamine, (O21) fenhexamine, (O22) flumetover, (O23) fluoroimide, (O24) flusulfamide, (O25) flutianil, (O26) fosetyl-aluminium, (O27) fosetyl-calcium, (O28) fosetyl-sodium, (O29) hexachlorobenzene, (O30) irumamycin, (O31) isothianil, (O32) methasulfocarb, (O33) methyl isothiocyanate, (O34) metrafenone, (O35) mildiomycin, (O36) natamycin, (O37) nickel dimethyldithiocarbamate, (O38) nitrothal-isopropyl, (O39) oxamocarb, (O40) oxyfenthiin, (O41) pentachlorophenol and salts, (O42) phenothrin, (O43) picarbutrazox (O44) phosphorous acid and its salts, (O45) propamocarb-fosetylate, (O46) propanosine-sodium, (O47) pyrimorph, (O48) pyraziflumid (O49) pyrrolnitrine, (O50) tebufloquin, (O51) tecloftalam, (O52) tolnifanide, (O53) triazoxide, (O54) trichlamide, (O55) zarilamid, (O56) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (O57) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (O58) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (O59) dichlobentiazox, (O60) 1-(4-methoxyphenoxy)-3,3-dimethylbutan-2-yl-1H-imidazole-1-carboxylate, (O61) 2,3,5,6-tetrachloro-4-(methylsulfonyl)pyridine, (O62) 2,3-dibutyl-6-chlorothieno[2,3-d]pyrimidin-4(3H)-one, (O63) 2,6-dimethyl-1H,5H-[1,4]dithiino[2,3-c:5,6-c']dipyrrole-1,3,5,7(2H,6H)-tetrone, (O64) 2-[5-methyl-3-(trifluoromethyl)-H-pyrazol-1-yl]-1-(4-{4-[(5R)-5-phenyl-4,5-dihydro-1,2-oxazol-3-yl]-1,3-thiazol-2-yl}piperidin-1-yl)ethanone, (O65) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (O66) 2-[5-methyl-3-(trifluoromethyl)-H-pyrazol-]-yl]-1-{4-[4-(5-phenyl-4,5-dihydro-1,2-oxazol-3-yl)-1,3-thiazol-2-yl]piperidin-1-yl}ethanone, (O67) 2-butoxy-6-iodo-3-propyl-4H-chromen-4-one, (O68) 2-chloro-5-[2-chloro-1-(2,6-difluoro-4-methoxyphenyl)-4-methyl-1H-imidazol-5-yl]pyridine, (O69) 2-phenylphenol and salts, (O70) 3-(4,4,5-trifluoro-3,3-dimethyl-3,4-dihydroisoquinolin-1-yl)quinoline, (O71) 3,4,5-trichloropyridine-2,6-dicarbonitrile, (O72) 3-chloro-5-(4-chlorophenyl)-4-(2,6-difluorophenyl)-6-methylpyridazine, (O73) 4-(4-chlorophenyl)-5-(2,6-difluorophenyl)-3,6-dimethylpyridazine, (O74) 3-chloro-4-(2,6-difluorophenyl)-6-methyl-5-phenylpyridazine, (O75) 5-amino-1,3,4-thiadiazole-2-thiol, (O76) 5-chloro-N'-phenyl-N'-(prop-2-yn-1-yl)thiophene-2-sulfonohydrazide, (O77) 5-fluoro-2-[(4-fluorobenzyl)oxy]pyrimidin-4-amine, (O78) 5-fluoro-2-[(4-methylbenzyl)oxy]pyrimidin-4-amine, (O79) 5-methyl-6-octyl[1,2,4]triazolo[1,5-a]pyrimidin-7-amine, (O80) ethyl (2Z)-3-amino-2-cyano-3-phenylacrylate, (O81) N'-(4-{[3-(4-chlorobenzyl)-1,2,4-thiadiazol-5-yl]oxy}-2,5-dimethylphenyl)-N-ethyl-N-methylimidoformamide, (O82) N-(4-chlorobenzyl)-3-[3-methoxy-4-(prop-2-yn-1-yloxy)phenyl]propanamide, (O83) N-[(4-chlorophenyl)(cyano)methyl]-3-[3-methoxy-4-(prop-2-yn-1-yloxy)phenyl]propanamide, (O84) N-[(5-bromo-3-chloropyridin-2-yl)methyl]-2,4-dichloronicotinamide, (O85) N-[1-(5-bromo-3-chloropyridin- 2-yl)ethyl]-2,4-dichloronicotinamide, (O86) N-[1-(5-bromo-3-chloropyridin-2-yl)ethyl]-2-fluoro-4-iodonicotinamide, (O87) N-{(E)-[(cyclopropylmethoxy)imino][6-(difluoromethoxy)-2,3-difluorophenyl]methyl}-2-phenylacetamide, (O88) N-{(Z)-[(cyclopropylmethoxy)imino][6-(difluoromethoxy)-2,3-difluorophenyl]methyl}-2-phenylacetamide, (O89) N'-{4-[(3-tert-butyl-4-cyano-1,2-thiazol-5-yl)oxy]-2-chloro-5-methylphenyl}-N-ethyl-N-methylimidoformamide, (O90) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (O91) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (O92) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (O93) pentyl {6-[{([(1-methyl-1H-tetrazol-5-yl)(phenyl)methylene]amino}oxy)methyl]pyridin-2-yl}carbamate, (O94) phenazine-1-carboxylic acid, (O95) quinolin-8-ol, (O96) quinolin-8-ol sulfate (2:1), (O97) tert-butyl {6-[({[(1-methyl-1H-tetrazol-5-yl)(phenyl) methylene]amino}oxy)methyl]pyridin-2-yl}carbamate, (O98) (5-bromo-2-methoxy-4-methylpyridin-3-yl)(2,3,4-trimethoxy-6-methylphenyl) methanone, (O99) N-[2-(4-{[3-(4-chlorophenyl)prop-2-yn-1-yl]oxy}-3-methoxyphenyl) ethyl]-N2-(methylsulfonyl)valinamide, (O100) 4-oxo-4-[(2-phenylethyl)amino]butanoic acid, (O101) but-3-yn-1-yl {6-[({[(Z)-(1-methyl-1H-tetrazol-5-yl)(phenyl)methylene] amino}oxy)methyl]pyridin-2-yl}carbamate, (O102) 4-amino-5-fluoropyrimidin-2-ol (tautomeric form: 4-amino-5-fluoropyrimidin-2(1H)-one), (O103) propyl 3,4,5-trihydroxybenzoate, (O104) [3-(4-chloro-2-fluorophenyl)-5-(2,4-difluorophenyl)-1,2-oxazol-4-yl](pyridin-3-yl)methanol, (O105) (S)-[3-(4-chloro-2-fluorophenyl)-5-(2,4-difluorophenyl)-1,2-oxazol-4-yl](pyridin-3-yl)methanol, (O106) (R)-[3-(4-chloro-2-fluorophenyl)-5-(2,4-difluorophenyl)-1,2-oxazol-4-yl](pyridin-3-yl)methanol, (O107) 2-fluoro-6-(trifluoromethyl)-N-(1,1,3-trimethyl-2,3-dihydro-1H-inden-4-yl)benzamide, (O108) 2-(6-benzylpyridin-2-yl) quinazoline, (O109) 2-[6-(3-fluoro-4-methoxyphenyl)-5-methylpyridin-2-yl]quinazoline, (O110) 3-(4,4-difluoro-3,3-dimethyl-3,4-dihydroisoquinolin-1-yl)quinoline, (O111) Abscisic acid, (O112) N'-[5-bromo-6-(2,3-dihydro-1H-inden-2-yloxy)-2-methylpyridin-3-yl]-N-ethyl-N-methylimidoformamide, (O113) N'-{5-bromo-6-[1-(3,5-. difluorophenyl)ethoxy]-2-methylpyridin-3-yl}-N-ethyl-N-methylimidoformamide, (O114) N'-{5-bromo-6-[(1R)-1-(3,5-difluorophenyl)ethoxy]-2-methylpyridin-3-yl}-N-ethyl-N-methylimidoformamide, (O115) N'-{5-bromo-6-[(1S)-1-(3,5-difluorophenyl)ethoxy]-2-methylpyridin-3-yl}-N-ethyl-N-methylimidoformamide, (O116) N'-{5-bromo-6-[(cis-4-isopropylcyclohexyl)oxy]-2-methylpyridin-3-yl}-N-ethyl-N-methylimidoformamide, (O117) N'-{5-bromo-6-[(trans-4-isopropylcyclohexyl)oxy]-2-methylpyridin-3-yl}-N-ethyl-N-methylimidoformamide, (O118) N-cyclopropyl-3-(difluoromethyl)-5-fluoro-N-(2-isopropylbenzyl)-1-methyl-1H-pyrazole-4-carboxamide, (O119) N-cyclopropyl-N-(2-cyclopropylbenzyl)-3-(difluoromethyl)-5-fluoro-1-methyl-1H-pyrazole-4-carboxamide, (O120) N-(2-tert-butylbenzyl)-N-cyclopropyl-3-(difluoromethyl)-5-fluoro-1-methyl-1H-pyrazole-4-carboxamide, (O121) N-(5-chloro-2-ethylbenzyl)-N-cyclopropyl-3-(difluoromethyl)-5-fluoro-1-methyl-1H-pyrazole-4-carboxamide, (O122) N-(5-chloro-2-isopropylbenzyl)-N-cyclopropyl-3-(difluoromethyl)-5-fluoro-1-methyl-1H-pyrazole-4-carboxamide, (O123) N-cyclopropyl-3-(difluoromethyl)-N-(2-ethyl-5-fluorobenzyl)-5-fluoro-1-methyl-1H-pyrazole-4-carboxamide, (O124) N-cyclopropyl-3-(difluoromethyl)-5-fluoro-N-(5-fluoro-2-isopropylbenzyl)-1-methyl-1H-pyrazole-4-carboxamide, (O125) N-cyclopropyl-N-(2-cyclopropyl-5-fluorobenzyl)-3-(difluoromethyl)-5-fluoro-1-methyl-1H-pyrazole-4-carboxamide, (O126) N-(2-cyclopentyl-5-fluorobenzyl)-N-cyclopropy-3-(difluoromethyl)-5-fluoro-1-methyl-1H-pyrazole-4-carboxamide, (O127) N-cyclopropyl-3-(difluoromethyl)-5-fluoro-N-(2-fluoro-6-isopropyl-benzyl)-1-methyl-1H-pyrazole-4-carboxamide, (O128) N-cyclopropyl-3-(difluoromethyl)-N-(2-ethyl-5-methylbenzyl)-5-fluoro-1-methyl-1H-pyrazole-4-carboxamide, (O129) N-cyclopropyl-3-(difluoromethyl)-5-fluoro-N-(2-isopropyl-5-methylbenzyl)-1-methyl-1H-pyrazole-4-carboxamide, (O130) N-cyclopropyl-N-(2-cyclopropyl-5-methylbenzyl)-3-(difluoromethyl)-5-fluoro-1-methyl-1H-pyrazole-4-carboxamide, (O131) N-(2-tert-butyl-5-methylbenzyl)-N-cyclopropyl-3-(difluoromethyl)-5-fluoro-1-methyl-1H-pyrazole-4-carboxamide, (O132) N-[5-chloro-2-(trifluoromethyl)benzyl]-N-cyclopropyl-3-(difluoromethyl)-5-fluoro-1-methyl-H-pyrazole-4-carboxamide, (O133) N-cyclopropyl-3-(difluoromethyl)-5-fluoro-1-methyl-N-[5-methyl-2-(trifluoromethyl)benzyl]-1H-pyrazole-4-carboxamide, (O134) N-[2-chloro-6-(trifluoromethyl)benzyl]-N-cyclopropyl-3-(difluoromethyl)-5-fluoro-1-methyl-1H-pyrazole-4-carboxamide, (O135) N-[3-chloro-2-fluoro-6-(trifluoromethyl)benzyl]-N-cyclopropyl-3-(difluoromethyl)-5-fluoro-1-methyl-1H-pyrazole-4-carboxamide, (O136) N-cyclopropyl-3-(difluoromethyl)-N-(2-ethyl-4,5-dimethylbenzyl)-5-fluoro-1-methyl-1H-pyrazole-4-carboxamide, (O137) N-cyclopropyl-3-(difluoromethyl)-5-fluoro-N-(2-isopropylbenzyl)-1-methyl-1H-pyrazole-4-carbothioamide, (O138) N'-(2,5-dimethyl-4-phenoxyphenyl)-N-ethyl-N-methylimidoformamide, (O139) N'-{4-[(4,5-dichloro-1,3-thiazol-2-yl)oxy]-2,5-dimethylphenyl}-N-ethyl-N-methylimidoformamide, (O140) N-(4-chloro-2,6-difluorophenyl)-4-(2-chloro-4-fluorophenyl)-1,3-dimethyl-1H-pyrazol-5-amine, (O141) 9-fluoro-2,2-dimethyl-5-(quinolin-3-yl)-2,3-dihydro-1,4-benzoxazepine, (O142) 2-(2-fluoro-6-[(8-fluoro-2-methylquinolin-3-yl)oxy]phenyl}propan-2-ol, (O143) 2-{2-[(7,8-difluoro-2-methylquinolin-3-yl)oxy]-6-fluorophenyl}propan-2-ol, (O144) 4-(2-chloro-4-fluorophenyl)-N-(2-fluorophenyl)-1,3-dimethyl-1H-pyrazol-5-amine, (O145) 4-(2-chloro-4-fluorophenyl)-N-(2,6-difluorophenyl)-1,3-dimethyl-1H-pyrazol-5-amine, (O146) 4-(2-chloro-4-fluorophenyl)-N-(2-chloro-6-fluorophenyl)-1,3-dimethyl-1H-pyrazol-5-amine, (O147) 4-(2-bromo-4-fluorophenyl)-N-(2-chloro-6-fluorophenyl)-1,3-dimethyl-1H-pyrazol-5-amine, (O148) N-(2-bromo-6-fluorophenyl)-4-(2-chloro-4-fluorophenyl)-1,3-dimethyl-1H-pyrazol-5-amine, (O149) 4-(2-bromo-4-fluorophenyl)-N-(2-bromophenyl)-1,3-dimethyl-1H-pyrazol-5-amine, (O150) 4-(2-bromo-4-fluorophenyl)-N-(2-bromo-6-fluorophenyl)-1,3-dimethyl-1H-pyrazol-5-amine, (O151) 4-(2-bromo-4-fluorophenyl)-N-(2-chlorophenyl)-1,3-dimethyl-1H-pyrazol-5-amine, (O152) N-(2-bromophenyl)-4-(2-chloro-4-fluorophenyl)-1,3-dimethyl-1H-pyrazol-5-amine, (O153) 4-(2-chloro-4-fluorophenyl)-N-(2-chlorophenyl)-1,3-dimethyl-1H-pyrazol-5-amine, (O154) 4-(2-bromo-4-fluorophenyl)-N-(2,6-difluorophenyl)-1,3-dimethyl-1H-pyrazol-5-amine, (O155) 4-(2-bromo-4-fluorophenyl)-N-(2-fluorophenyl)-1,3-dimethyl-1H-pyrazol-5-amine, (O156) N'-(4-{3-[(difluoromethyl)sulfanyl]phenoxy}-2,5-dimethylphenyl)-N-ethyl-N-methylimidoformamide, (O157) N'-(2,5-dimethyl-4-{3-[(1,1,2,2-tetrafluoroethyl)sulfanyl]phenoxy}phenyl)-N-ethyl-N-methylimidoformamide, (O158) N'-(2,5-dimethyl-4-{3-[(2,2,2- trifluoroethyl)sulfanyl]phenoxy}phenyl)-N-ethyl-N-methylimidoformamide, (O159) N'-(2,5-dimethyl-4-{3-[(2,2,3,3-tetrafluoropropyl)sulfanyl]phenoxy}phenyl)-N-ethyl-N-methylimidoformamide, (O160) N'-(2,5-dimethyl-4-{3-[(pentafluoroethyl)sulfanyl]phenoxy}phenyl)-N-ethyl-N-methylimidoformamide, (O161) N'-(4-{[3-(difluoromethoxy)phenyl]sulfanyl}-2,5-dimethylphenyl)-N-ethyl-N-methylimidoformamide, (O162) N'-(2,5-dimethyl-4-{[3-(1,1,2,2-tetrafluoroethoxy)phenyl]sulfanyl)phenyl)-N-ethyl-N-methylimidoformamide, (O163) N'-(2,5-dimethyl-4-{[3-(2,2,2-trifluoroethoxy)phenyl]sulfanyl}phenyl)-N-ethyl-N-methylimidoformamide, (O164) N'-(2,5-dimethyl-4-{[3-(2,2,3,3-tetrafluoropropoxy)phenyl]sulfanyl)phenyl)-N-ethyl-N-methylimidoformamide, (O165) N'-(2,5-dimethyl-4-{[3-(pentafluoroethoxy)phenyl]sulfanyl}phenyl)-N-ethyl-N-methylimidofomiamide, (O166) 2-[3,5-bis(difluoromethyl)-1H-pyrazol-1-yl]-1-[4-(4-(5-[2-(prop-2-yn-1-yloxy)phenyl]-4,5-dihydro-1,2-oxazol-3-yl}-1,3-thiazol-2-yl}piperidin-1-yl]ethanone, (O167) 2-[3,5-bis(difluoromethyl)-H-pyrazol-1-yl]-1-[4-(4-{5-[2-fluoro-6-(prop-2-yn-1-yloxy)phenyl]-4,5-dihydro-1,2-oxazol-3-yl)-1,3-thiazol-2-yl}piperidin-1-yl]ethanone, (O168) 2-[3,5-bis(difluoromethyl)-H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (O169) 2-{3-[2-(1-{[3,5-bis(difluoromethyl)-1H-pyrazol-1-yl]acetyl}pi- peridin-4-yl)-1,3-thiazol-4-yl]-4,5-dihydro-1,2-oxazol-5-yl} phenyl methanesulfonate, (O170) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (O171) 2-[3,5-bis(difluoromethyl)-H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (O172) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl]-1,3-thiazol-2-yl}piperidin-1-yl]ethanone, (O173) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl)-1,3-thiazol-2-yl}piperidin-1-yl]ethanone, (O174) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl)-1,3-thiazol-2-yl}piperidin-1-yl]ethanone, (O175) 2-[3,5-bis(difluoromethyl)-1H-pyrazol-1-yl]-1-[4-(4-{(5S)-5-[2-chloro-6-(prop-2-yn- 1-yloxy)phenyl]-4,5-dihydro-1,2-oxazol-3-yl)-1,3-thiazol-2-yl}piperidin-1-yl]ethanone, (O176) 2-[3,5-bis(difluoromethyl)-1H-pyrazol-1-yl]-1-[4-(4-{(SR)-5-[2-chloro-6-(prop-2-yn-1-yloxy)phenyl]-4,5-dihydro-1,2-oxazol-3-yl)-1,3-thiazol-2-yl}piperidin-1-yl]ethanone, (O177) 2-((5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl)phenyl methanesulfonate, (O178) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (O179) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (O180) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (O181) (3S,6S,7R,8R)-8-benzyl-3-[(isobutyryloxy)methoxy]-4-methoxypicolinamido)-6-methyl-4,9-dioxo-1,5-dioxonan-7-yl isobutyrate, (O182) N'-(4-(4-chloro-3-trifluoromethyl-phenoxy)-2,5-dimethyl-phenyl]-N-ethyl-N-methyl formamidine, (O183) N'-(4-(4-fluoro-3-trifluoromethyl-phenoxy)-2,5-dimethyl-phenyl)-N-ethyl-N-methylformamidine, (O184) N'-[4-[[3-[(4-chlorophenyl)methyl]-1,2,4-thiadiazol-5-yl]oxy]-2,5-dimethyl-phenyl]-N-ethyl-N-methyl-formamidine, (O185) N'-(5-bromo-6-indan-2-yloxy-2-methyl-3-pyridyl)-N-ethyl-N-methyl-formamidine, (O186) N'-[5-bromo-6-[1-(3,5-difluorophenyl)ethoxy]-2 methyl-3-pyridyl]-N-ethyl-N-methyl-formamidine, (O187) N'-[5-bromo-6-(4-isopropyl-cyclohexoxy)-2-methyl-3-pyridyl]-N-ethyl-N-methyl-formamidine, (O188) N'-[5-bromo-2-methyl-6-(1-phenylethoxy)-3-pyridyl]-N-ethyl-N-methylformamidine, (O189) N'-(2-methyl-5-trifluoromethyl-4-(3-trimethylsilanyl-propoxy)phenyl)-N-ethyl-N-methyl formamidine, (O190) N'-(5-difluoromethyl-2-methyl-4-(3-trimethylsilanyl-propoxy)-phenyl)-N-ethyl-N-methyl formamidine, (O191), (N-ethyl-N'-(4-(2-fluorophenoxy)-2,5-dimethylphenyl)-N-methylformimidamide, (O192) N'-(2-chloro-4-(2-fluorophenoxy)-5-methylphenyl)-N-ethyl-N-methylformimidamide, (O193)$^2$-[$^2$-[(7,8-difluoro-2-methyl-3-quinolyl)oxy]-6-fluoro-phenyl]propan-2-ol, (O194)$^2$-[$^2$-fluoro-6-[(8-fluoro-2-methyl-3-quinolyl)oxy]-phen-yl]propan-2-ol, (O195)quinofumelin, (O196) 9-fluoro-2,2-dimethyl-5-(3-quinolyl)-3H-1,4-benzoxazepine, (O197) 2-(6-benzyl-2-pyridyl)quinazoline, (O198) 2-[6-(3-fluoro-4-methoxy-phenyl)-5-methyl-2-pyridyl]quinazoline, (O199) Fluopimomide, (O200) 3-chloro-4-(2,6-difluorophenyl)-6-methyl-5-phenylpyridazine, (O201) 1-[2-[[[ 1-(4-chlorophenyl)-H-pyrazol-3-yl]oxy]methyl]-3-methylphenyl]-1,4-dihydro-4-methyl-5H-tetrazol-5-one, (O202) (4-phenoxyphenyl)methyl 2-amino-6-methyl-3-pyridinecarboxylate (CAS. NO.: 1531626-08-0), (O203) 3-(difluoromethyl)-N-[(3R)-2,3-dihydro-1,1,3-trimethyl-1H-inden-4-yl]-1-methyl-H-pyrazole-4-carboxamide (CAS. NO.:1352994-67-2), (O204) 3-(difluoromethyl)-N-(7-fluoro-2,3-dihydro-1,1,3-trimethyl-1H-inden-4-yl)-1-methyl-1H-pyrazole-4-carboxamide (CAS NO.:1383809-87-7), (O205) [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropanoate (CAS No 517875-34-2), (O206) (S)-2,2-bis(4-fluorophenyl)-1-methylethyl N-[[3-(acetyloxy)-4-methoxy-2-pyridinyl]carbonyl]-L-alaninate (CAS. NO.:1961312-55-9).

P) Growth regulators, for example abscisic acid, amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapacethyl and uniconazole;

The active substances referred above, their preparation and their activity e.g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141317; EP-A 152031; EP-A 226917; EP-A 243 970; EP-A 256503; EP-A 428941; EP-A 532022; EP-A 1028125; EP-A1035122; EP-A 1201648; EP-A 1122244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 94/01546, EP 2865265, WO 07/129454, WO 12/165511, WO 11/081174, WO 13/47441).

As described above the compound of formula (I) can be mixed with one or more active compatible compound selected from insecticides/acaricides/nematicides class, which are specified herein by their common names that are known and described, for example in *The Pesticide Manual* 17th Ed., or can be searched in the internet (e.g. under www.alanwood.net/pesticides).

(1) Acetylcholinesterase (AChE) inhibitors such as carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb or organophosphates, such as acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as cyclodiene organochlorines, for example chlordane and endosulfan or phenylpyrazoles (fiproles), for example ethiprole and fipronil.

(3) Sodium channel modulators/voltage-dependent sodium channel blockers, such as pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer), prallethrin, pyrethrins (pyrethrum), resmethrin, silafluofen, tefluthrin, tetramethrin, tetramethrin [(1R)-isomers], tralomethrin and transfluthrin or DDT or methoxychlor.

(4) Nicotinic acetylcholine receptor (nAChR) competitive modulators, such as neonicotinoids, for example acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as spinosyns, for example spinetoram and spinosad.

(6) Glutamate-gated chloride channel (GluCl) allosteric modulators, such as avermectins/milbemycins, for example abamectin, emamectin benzoate, lepimectin and milbemectin.

(7) Juvenile hormone mimics such as juvenile hormone analogues, for example hydroprene, kinoprene and methoprene or fenoxycarb or pyriproxyfen.

(8) Active compounds with unknown or non-specific mechanisms of action, such as alkyl halides for example as methyl bromide and other alkyl halides or chloropicrin or fluorides or borates or tartar emetic or methyl isocyanate generators.

(9) Chordotonal organ TRPV channel modulators such as pyridine azomethine derivatives, for example pymetrozine and pyrifluquinazon or flonicamid.

(10) Mite growth inhibitors, for example clofentezine, hexythiazox and diflovidazin or etoxazole.

(11) Microbial disruptors of insect gut midgut, for example *Bacillus thuringiensis* subspecies *israelensis*, *Bacillus thuringiensis* subspecies *aizawai*, *Bacillus thuringiensis* subspecies kurstaki, *Bacillus thuringiensis* subspecies tenebrionis and *Bacillus sphaericus* and BT crop proteins: Cry1Ab, Cry1Ac, Cry1Fa, Cry1A 105, Cry2Ab, Vip3a, mCry3A, Cry3Ab, Cry3Bb, Cry34Ab1/Cry35Ab1.

(12) Inhibitors of mitochondrial ATP synthase such as organotin miticides, for example azocyclotin, cyhexatin and fenbutatin oxide or diafenthiuron or propargite or tetradifon.

(13) Uncouplers of oxidative phosphorylation acting via disruption of the proton gradient, for example chlorfenapyr, DNOC and sulfluramid.

(14) Nicotinic acetylcholine receptor (nAChR) channel blockers, such as bensultap, cartap-hydrochloride, thiocyclam and thiosultap-sodium.

(15) Inhibitors of chitin biosynthesis, type 0, such as bistrifluoron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, such as buprofezin.

(17) Molting disruptors (particularly in Dipteran), such as cyromazine.

(18) Ecdysone receptor agonists, such as chromafenozide, halofenozide, methoxyfenozide and tebufenozide.

(19) Octopamine receptor agonists, such as amitraz.

(20) Mitochondrial complex III electron transport inhibitors such as hydramethylnon or acequinocyl or fluacrypyrim or bifenazate.

(21) Mitochondrial complex I electron transport inhibitors, for example, METI acaricides and insecticides, for example fenazaquin, fenpyroximate, pyrimidifen, pyridaben, tebufenpyrad and tolfenpyrad or rotenone (Derris).

(22) Voltage-dependent sodium channel blockers such as indoxacarb or metaflumizone.

(23) Inhibitors of acetyl CoA carboxylase, such as tetronic and tetramic acid derivatives, for example spirodiclofen, spiromesifen and spirotetramat.

(24) Mitochondrial complex IV electron transport inhibitors, such as phosphides, for example aluminum phosphide, calcium phosphide, zinc phosphide and phosphine or cyanides.

(25) Mitochondrial complex II electron transport inhibitors such as beta-ketonitrile derivatives, for example cyenopyrafen and cyflumetofen or carboxanilides.

(28) Ryanodine receptor modulators such as diamides, for example chlorantraniliprole, cyantraniliprole, flubendiamide, tetraniliprole, (R)-3-chloro-N-1-{2-methyl-4-[1,2,2,2-tetrafluoro-1-(trifluoromethyl)ethyl]phenyl}-N2-(1-methyl-2-methylsulfonylethyl)phthalamide, (S)-3-chloro-N1-{2-methyl-4-[1,2,2,2-tetrafluoro-1-(trifluoromethyl)ethyl]phenyl}-N2-(1-methyl-2-methylsulfonylethyl)phthalamide, methyl-2-[3,5-dibromo-2-({[3-bromo-1-(3-chloropyridin-2-yl)-1H-pyrazol-5-yl]carbonyl}amino)benzoyl]-1,2-dimethylhydrazinecarboxylate, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide, N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide, N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide, N-[4,6-dichloro-2-[(di-2-propyl-lambda-4-sulfanylidene)carbamoyl]phenyl]-2-(3-chloro-2-pyridyl)-5-(trifluoromethyl)pyrazole-3-carboxamide, N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide, N-[2-(5-amino-1,3,4-thiadiazol-2-yl)-4-chloro-6-methylphenyl]-3-bromo-1-(3-chloro-2-pyridinyl)-1H-pyrazole-5-carboxamide; 3-chloro-1-(3-chloro-2-pyridinyl)-N-[2,4-dichloro-6-[[(1-cyano-1-methylethyl)amino]carbonyl]phenyl]-1H-pyrazole-5-carboxamide, 3-bromo-N-[2,4-dichloro-6-(methylcarbamoyl)phenyl]-1-(3,5-dichloro-2-pyridyl)-1H-pyrazole-5-carboxamide, N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide and cyhalodiamide.

(29) Chordotonal organ modulators on undefined target site such as flonicamid.

Further active ingredients with unknown or indeterminate mode of action, such as afidopyropen, afoxolaner, azadirachtin, benclothiaz, benzoximate, bifenazate, broflanilide, bromopropylate, chinomethionat, cryolite, cyclaniliprole, cycloxaprid, cyhalodiamide, dicloromezotiaz, dicofol, diflovidazin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetrachlorantraniliprole, tioxazafen, triflumezopyrim and iodomethane; furthermore, preparations based on *Bacillus firmus* (I-1582, BioNeem, Votivo), and the following known active compounds: 1-{2-fluoro-4-methyl-5-[(2,2,2-trifluoroethyl)sulfinyl]phenyl}-3-(trifluoromethyl)-1H-1,2,4-triazol-5-amine (known from WO2006043635), {1'-[(2E)-3-(4-chlorophenyl)prop-2-ene-1-yl]-5-fluorospiro[indole-3,4'-piperidine]-1(2H)-yl}(2-chloropyridin-4-yl)methanone (known from WO2003106457), 2-chloro-N-[2-{-[(2E)-3-(4-chlorophenyl)prop-2-en-1-yl]piperidin-4-yl}-4-(trifluoromethyl)phenyl]isonicotinamide (known from WO2006003494), 3-(2,5-dimethylphenyl)-4-hydroxy-8-methoxy-1,8-diazaspiro[4.5]dec-3-en-2-one (known from WO2009049851), 3-(2,5-dimethylphenyl)-8-methoxy-2-oxo-1,8-diazaspiro[4.5]dec-3-en-4-yl ethyl carbonate (known from WO2009049851), 4-(but-2-in-1-yloxy)-6-(3,5-dimethylpiperidin-1-yl)-5-fluoropyrimidine (known from WO2004099160), 4-(but-2-in-1-yloxy)-6-(3-chlorophenyl)pyrimidine (known from WO2003076415), PF1364 (CAS-Reg. No. 1204776-60-2), [methyl-2-[2-({[3-bromo-1-(3-chloropyridin-2-yl)-1H-pyrazol-5-yl]carbonyl)amino)-5-chloro-3-methylbenzoyl]-2-methylhydrazincarboxylate, methyl-2-[2-(([3-bromo-1-(3-chloropyridin-2-yl)-1H-pyrazol-5-yl]carbonyl}amino)-5-cyano-3-methylbenzoyl]-2-ethylhydrazincarboxylate, methyl-2-[2-({[3-bromo-1-(3-chloro-pyridin-2-yl)-1H-pyrazol-5-yl]carbonyl)amino)-5-cyano-3-methylbenzoyl]-2-methylhydrazincarboxylate and methyl-2-[3,5-dibromo-2-(([3-bromo-1-(3-chloro-pyridin-2-yl)-1H-pyrazol-5-yl]carbonyl}amino)benzoyl]-2-ethylhydrazincarboxylate (known from WO2005085216)], N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009080250), N-[(2E)-1-[(6-chloropyridine-3-yl)methyl]pyridin-2(1H)-ylidene]-2,2,2-trifluoroacetamide (known from WO2012029672), 1-[(2-chloro-1,3-thiazol-5-yl)methyl]-4-oxo-3-phenyl-4H-pyrido[1,2-a]pyrimidin-1-ium-2-olate (known from WO2009099929), 1-[(6-chloropyridin-3-yl)methyl]-4-oxo-3-phenyl-4H-pyrido[1,2-a]pyrimidin-1-ium-2-olate (known from WO2009099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008134969), butyl-[2-(2,4-dichlorophenyl)-3-oxo-4-oxaspiro[4.5]dec-1-en-1-yl] carbonate (disclosed in CN102060818), 3(E)-3-[1-[(6-chloro-3-pyridyl)methyl]-2-pyridyliden]-1,1,1-trifluoropropan-2-one (known from WO2013144213), N-(methylsulfonyl)-6-[2-(pyridin-3-yl)-1,3-thiazol-5-yl]pyridine-2-carboxamide (known from WO2012000896), N-[3-(benzylcarbamoyl)-4-chlorophenyl]-1-methyl-3-(pentafluoroethyl)-4-(trifluoromethyl)-1H-pyrazole-5-carboxamide (known from WO2010051926).

Other active compounds of unknown or uncertain mode of action: II-(4-chloro-2,6-dimethylphenyl)-12-hydroxy-1,4-dioxa-9-azadispiro[4.2.4.2]-tetradec-11-en-10-one, 3-(4'-fluoro-2,4-dimethylbiphenyl-3-yl)-4-hydroxy-8-oxa-1-azaspiro[4.5]dec-3-en-2-one, 1-[2-fluoro-4-methyl-5-[(2,2,2-trifluoroethyl)sulfinyl]phenyl]-3-(trifluoromethyl)-1H-1,2,4-triazole-5-amine, *Bacillus firmus*; (E/Z)—N-[1-[(6-chloro-3-pyridyl) methyl]-2-pyridylidene]-2,2,2-trifluoroacetamide; (E/Z)—N-[1-[(6-chloro-5-fluoro-3-pyridyl) methyl]-2-pyridylidene]-2,2,2-trifluoro-acetamide; (E/Z)-2,2,2-trifluoro-N-[1-[(6-fluoro-3-pyridyl)methyl]-2-pyridylidene]acetamide; (E/Z)—N-[1-[(6-bromo-3-pyridyl) methyl]-2-pyridylidene]-2,2,2-trifluoroacetamide; (E/Z)—N-[1-[1-(6-chloro-3-pyridyl)ethyl]-2-pyridylidene]-2,2,2-trifluoroacetamide; (E/Z)—N-[1-[(6-chloro-3-pyridyl) methyl]-2-pyridylidene]-2,2-difluoro-acetamide; (E/Z)-2-chloro-N-[1-[(6-chloro-3-pyridyl) methyl]-2-pyridylidene]-2,2-difluoro-acetamide; (E/Z)—N-[1-[(2-chloropyrimidin-5-yl)methyl]-2-pyridylidene]-2,2,2-trifluoro-acetamide; (E/Z)—N-[1-[(6-chloro-3-pyridyl)methyl]-2-pyridylidene]-2,2,3,3,3-pentafluoro-propanamide; N-[1-[(6-chloro-3-pyridyl)methyl]-2-pyridylidene]-2,2,2-trifluoro-thioacetamide; N-[1-[(6-chloro-3-pyridyl)methyl]-2-pyridylidene]-2,2,2-trifluoro-N'-isopropyl-acetamidine; fluazaindolizine;

4-[5-(3,5-dichlorophenyl)-5-(trifluoromethyl)-4H-isoxazol-3-yl]-2-methyl-N-(1-oxothietan-3-yl)benzamide; fluxametamide; 5-[3-[2,6-dichloro-4-(3,3-dichloroallyloxy)phenoxy]propoxy]-1H-pyrazole; 3-(benzoylmethylamino)-N-[2-bromo-4-[1,2,2,3,3,3-hexafluoro-1-(trifluoromethyl) propyl]-6-(trifluoromethyl)phenyl]-2-fluoro-benzamide; 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methylbenzamide; 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; 3-fluoro-N-[2-fluoro-3-[[[2-iodo-4-[1,2,2,2-tetrafluoro-1-(trifluoromethyl)ethyl]-6(trifluoromethyl)phenyl]amino]carbonyl]phenyl]-N-methyl-benzamide; 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide; 4-cyano-3-[(4-cyano-2-methyl-benzoyl)amino]-N-[2,6-dichloro-4-[1,2,2,3,3,3-hexafluoro-1-(trifluoromethyl) propyl]phenyl]-2-fluoro-benzamide; N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; N-[5-[[2-bromo-6-chloro-4-[1,2,2,3,3,3-hexafluoro-1-(trifluoromethyl); propyl]phenyl]carbamoyl]-2-cyano-phenyl]-4-cyano-2-methyl-benzamide; 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; 2-(1,3-dioxan-2-yl)-6-[2-(3-pyridinyl)-5-thiazolyl]-pyridine; 2-[6-[2-(5-fluoro-3-pyridinyl)-5-thiazolyl]-2-pyridinyl]-pyrimidine; 2-[6-[2-(3-pyridinyl)-5-thiazolyl]-2-pyridinyl]-pyrimidine; N-methylsulfonyl-6-[2-(3-pyridyl)thiazol-5-yl]pyridine-2-carboxamide; N-methylsulfonyl-6-[2-(3-pyridyl)thiazol-5-yl]pyridine-2-carboxamide; N-ethyl-N-[4-methyl-2-(3-pyridyl)thiazol-5-yl]-3-methylthio-propan amide; N-methyl-N-[4-methyl-2-(3-pyridyl)thiazol-5-yl]-3-methylthio-propanamide; N,2-dimethyl-N-[4-methyl-2-(3-pyridyl)thiazol-5-yl]-3-methylthiopropanamide; N-ethyl-2-methyl-N-[4-methyl-2-(3-pyridyl)thiazol-5-yl]-3-methylthio-propanamide; N-[4-chloro-2-(3-pyridyl)thiazol-5-yl]-N-ethyl-2-methyl-3-methylthio-propanamide; N-[4-chloro-2-(3-pyridyl)thiazol-5-yl]-N,2-dimethyl-3-methylthio-propanamide; N-[4-chloro-2-(3-pyridyl)thiazol-5-yl]-N-methyl-3-methylthio-propanamide; N-[4-chloro-2-(3-pyridyl)thiazol-5-yl]-N-ethyl-3-methylthio-propanamide; 1-[(6-chloro-3-pyridinyl)methyl]-1,2,3,5,6,7-hexahydro-5-methoxy-7-methyl-8-nitro-imidazo[1,2-a]pyridine; 1-[(6-chloropyridin-3-yl)methyl]-7-methyl-8-nitro-1,2,3,5,6,7-hexahydroimidazo[1,2-a]pyridin-5-ol; 1-isopropyl-N,5-dimethyl-N-pyridazin-4-yl-pyrazole-4-carboxamide; 1-(1,2-dimethylpropyl)-N-ethyl-5-methyl-N-pyridazin-4-yl-pyrazole-4-carboxamide; N,5-dimethyl-N-pyridazin-4-yl-1-(2,2,2-trifluoro-1-methyl-ethyl)pyrazole-4-carboxamide; 1-[1-cyanocyclopropyl) ethyl]-N-ethyl-5-methyl-N-pyridazin-4-yl-pyrazole-4-carboxamide; N-ethyl-1-(2-fluoro-1-methyl-propyl)-5-methyl-N-pyridazin-4-yl-pyrazole-4-carboxamide; 1-(1,2-dimethylpropyl)-N,5-dimethyl-N-pyridazin-4-yl-pyrazole-4-carboxamide; 1-[1-(1-cyanocyclopropyl)ethyl]-N,5-dimethyl-N-pyridazin-4-yl-pyrazole-4-carboxamide; N-methyl-1-(2-fluoro-1-methyl-propyl]-5-methyl-N-pyridazin-4-yl-pyrazole-4-carboxamide; 1-(4,4-difluorocyclohexyl)-N-ethyl-5-methyl-N-pyridazin-4-yl-pyrazole-4-carboxamide; 1-(4,4-difluorocyclohexyl)-N,5-dimethyl-N-pyridazin-4-yl-pyrazole-4-carboxamide; N-(1-methylethyl)-2-(3-pyridinyl)-2H-indazole-4-carboxamide; N-cyclopropyl-2-(3-pyridinyl)-2H-indazole-4-carboxamide; N-cyclohexyl-2-(3-pyridinyl)-2H-indazole-4-carboxamide; 2-(3-pyridinyl)-N-(2,2,2-trifluoroethyl)-2H-indazole-4-carboxamide; 2-(3-pyridinyl)-N-[(tetrahydro-2-furanyl)methyl]-2H-indazole-5-carboxamide; methyl 2-[[2-(3-pyridinyl)-2H-indazol-5-yl]carbonyl]hydrazinecarboxylate; N-[(2,2-difluorocyclopropyl)methyl]-2-(3-pyridinyl)-2H-indazole-5-carboxamide; N-(2,2-difluoropropyl)-2-(3-pyridinyl)-2H-indazole-5-carboxamide; 2-(3-pyridinyl)N-(2-pyrimidinylmethyl)-2H-indazole-5-carboxamide; N-[(5-methyl-2-pyrazinyl)methyl]-2-(3-pyridinyl)-2H-indazole-5-carboxamide, N-[3-chloro-1-(3-pyridyl) pyrazol-4-yl]N-ethyl-3-(3,3,3-trifluoropropylsulfanyl) propanamide; N-[3-chloro-1-(3-pyridyl) pyrazol-4-yl]-N-ethyl-3-(3,3,3-trifluoropropylsu- lfinyl)propanamide; N-[3-chloro-1-(3-pyridyl)pyrazol-4-yl]-3-[(2,2-difluorocyclopropyl)methylsulfanyl]-N-ethyl-propanamide; N-[3-chloro-1-(3-pyridyl) pyrazol-4-yl]-3-[(2,2-difluorocyclopropyl) methylsulfinyl]-N-ethyl-propa- namide; sarolaner, lotilaner, tetrachlorantraniliprole.

The compounds of formula (I) may be used to treat several fungal pathogens. Non-limiting examples of pathogens of fungal diseases which can be treated in accordance with the invention include: diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*; *Erysiphe* species, for example *Erysiphe cichoracearu*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita*, *Puccinia graminis* or *Puccinia striiformis* and *Puccinia melanocephala*; *Uromyces* species, for example *Uromyces appendiculatus*;

In particular, *Cronartium ribicola* (White pine blister rust); *Gymnosporangium juniperi-virginianae* (Cedar-apple rust); *Hemileia vastatrix* (Coffee rust); *Phakopsora meibomiae* and *P. pachyrhizi* (Soybean rust); *Puccinia coronata* (Crown Rust of Oats and Ryegrass); *Puccinia graminis* (Stem rust of wheat and Kentucky bluegrass, or black rust of cereals); *Puccinia hemerocallidis* (Daylily rust); *Puccinia persistens* subsp. *triticina* (wheat rust or 'brown or red rust'); *Puccinia sorghi* (rust in corn); *Puccinia striiformis* ('Yellow rust' in cereals); *Puccinia melanocephala*; *Uromyces appendiculatus* (rust of beans); *Uromyces phaseoli* (Bean rust); *Puccinia melanocephala* ('Brown rust' in sugarcane); *Puccinia kuehnii* ('Orange rust' in sugarcane).

diseases caused by pathogens from the group of the Oomycetes, for example *Albugo* species, for example *Albugo candida*; *Bremia* species, for example *Bremia lac-* tucae; Peronospora species, for example Peronospora pisi or P. brassicae; Phytophthora species, for example Phytophthora infestans; Plasmopara species, for example Plasmopara viticola; Pseudoperonospora species, for example Pseudoperonospora humuli or Pseudoperonospora cubensis; Pythium species, for example Pythium ultimum;

leaf blotch diseases and leaf wilt diseases caused, for example, by Alternaria species, for example Alternaria solani; Cercospora species, for example Cercospora beticola; Cladiosporium species, for example Cladiosporium cucumerinum; Cochliobolus species, for example Cochliobolus sativus (conidial form: Drechslera, syn: Helminthosporium) or Cochliobolus miyabeanus; Colletotrichum species, for example Colletotrichum lindemuthanium; Cycloconium species, for example Cycloconium oleaginum; Diaporthe species, for example Diaporthe citri; Elsinoe species, for example Elsinoe fawcettii; Gloeosporium species, for example Gloeosporium laeticolor; Glomerella species, for example Glomerella cingulata; Guignardia species, for example Guignardia bidwelli; Leptosphaeria species, for example Leptosphaeria maculans; Magnaporthe species, for example Magnaporthe grisea; Microdochium species, for example Microdochium nivale; Mycosphaerella species, for example Mycosphaerella graminicola, Mycosphaerella arachidicola or Mycosphaerella fijiensis; Phaeosphaeria species, for example Phaeosphaeria nodorum; Pyrenophora species, for example Pyrenophora teres or Pyrenophora tritici repentis; Ramularia species, for example Ramularia collo-cygni or Ramularia areola; Rhynchosporium species, for example Rhynchosporium secalis; Septoria species, for example Septoria apii or Septoria lycopersici; Stagonospora species, for example Stagonospora nodorum; Typhula species, for example Typhula incarnata; Venturia species, for example Venturia inaequalis;

root and stem diseases caused, for example, by Corticium species, for example Corticium graminearum; Fusarium species, for example Fusarium oxysporum; Gaemnannomyces species, for example Gaeumannomyces graminis; Plasmodiophora species, for example Plasmodiophora brassicae; Rhizoctonia species, for example Rhizoctonia solani; Sarocladium species, for example Sarocladium oryzae; Sclerotium species, for example Sclerotium oryzae; Tapesia species, for example Tapesia acuformis; Thielaviopsis species, for example Thielaviopsis basicola; Ganoderma species, for example Ganoderma lucidum;

ear and panicle diseases (including corn cobs) caused, for example, by Alternaria species, for example Alternaria spp.; Aspergillus species, for example Aspergillus flavus; Cladosporium species, for example Cladosporium cladosporioides; Claviceps species, for example Claviceps purpurea; Fusarium species, for example Fusarium culmorum; Gibberella species, for example Gibberella zeae; Monographella species, for example Monographella nivalis; Stagnospora species, for example Stagnospora nodorum; diseases caused by smut fungi, for example Sphacelotheca species, for example Sphacelotheca reiliana; Tilletia species, for example Tilletia caries or Tilletia controversa; Urocystis species, for example Urocystis occulta; Ustilago species, for example Ustilago nuda;

fruit rot caused, for example, by Aspergillus species, for example Aspergillus favus; Botrytis species, for example Botrytis cinerea; Penicillium species, for example Penicillium expansum or Penicillium purpurogenum; Rhizopus species, for example Rhizopus stolonifer; Sclerotinia species, for example Sclerotinia sclerotiorum; Verticilium species, for example Verticilium alboatrum;

seed- and soil-borne rot and wilt diseases, and also diseases of seedlings, caused, for example, by Alternaria species, for example Alternaria brassicicola; Aphanomyces species, for example Aphanomyces euteiches; Ascochyta species, for example Ascochyta lentis; Aspergillus species, for example Aspergillus flavus; Cladosporium species, for example Cladosporium herbarum; Cochliobolus species, for example Cochliobolus sativus (conidial form: Drechslera, Bipolaris Syn: Helminthosporium); Colletotrichum species, for example Colletotrichum coccodes; Fusarium species, for example Fusarium culmorum; Gibberella species, for example Gibberella zeae; Macrophomina species, for example Macrophomina phaseolina; Microdochium species, for example Microdochium nivale; Monographella species, for example Monographella nivalis; Penicillium species, for example Penicillium expansum; Phoma species, for example Phoma lingam; Phomopsis species, for example Phomopsis sojae; Phytophthora species, for example Phytophthora cactorum; Pyrenophora species, for example Pyrenophora graminea; Pyricularia species, for example Pyricularia oryzae; Pythium species, for example Pythium ultimum; Rhizoctonia species, for example Rhizoctonia solani; Rhizopus species, for example Rhizopus oryzae; Sclerotium species, for example Sclerotium rolfsii; Septoria species, for example Septoria nodorum; Typhula species, for example Typhula incarnata; Verticillium species, for example Verticillium dahliae; cancers, galls and witches' broom caused, for example, by Nectria species, for example Nectria galligena;

wilt diseases caused, for example, by Monilinia species, for example Monilinia laxa; deformations of leaves, flowers and fruits caused, for example, by Exobasidium species, for example Exobasidium vexans; Taphrina species, for example Taphrina deformans;

degenerative diseases in woody plants, caused, for example, by Esca species, for example Phaeomoniella chlamydospora, Phaeoacremonium aleophilum or Fomitiporia mediterranea; Ganoderma species, for example Ganoderma boninense;

diseases of flowers and seeds caused, for example, by Botrytis species, for example Botryis cinerea; diseases of plant tubers caused, for example, by Rhizoctonia species, for example Rhizoctonia solani; Helminthosporium species, for example Helminthosporium solani;

diseases caused by bacterial pathogens, for example Xanthomonas species, for example Xanthomonas campestris pv. oryzae; Pseudomonas species, for example Pseudomonas syringae pv. lachrymans; Erwinia species, for example Erwinia amylovora; Ralstonia species, for example Ralstonia solanacearum;

Fungal diseases on roots and the stem base caused, for example, by black root rot (Calonectria crotalariae), charcoal rot (Macrophomina phaseolina), Fusarium blight or wilt, root rot, and pod and collar rot (Fusarium oxysporum, Fusarium orthoceras, Fusarium semitectum, Fusarium equiseti), mycoleptodiscus root rot (Mycoleptodiscus terrestris), neocosmospora (Neocosmospora vasinfecta), pod and stem blight (Diaporthe phaseolorum), stem canker (Diaporthe phaseolorum var. caulivora), phytophthora rot (Phytophthora megasperma), brown stem rot (Phialophora gregata), pythium rot (Pythium aphanidermatum, Pythium irregulare, Pythium debaryanum, Pythium myriotylwn, Pythium ultimum), Rhizoctonia root rot, stem decay, and damping-off (Rhizoctonia solam), sclerotinia stem decay (Sclerotinia sclerotiorum), Sclerotinia southern blight (Sclerotinia rolfsi), Thielaviopsis root rot (Thielaviopsis basicola).

Plants which can be treated in accordance with the invention include the following: cotton, flax, grapevine, fruits, vegetables, such as Rosaceae sp (for example pome fruits such as apples, pears, apricots, cherries, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Vitaceae sp. (for example grapes); Solanaceae sp. (for example tomatoes, peppers), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leek, onion), Papilionaceae sp. (for example peas); major crop plants, such as Poaceae/Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak choi, kohlrabi, radishes, and oilseed rape, mustard, horseradish and cress), Fabacae sp. (for example bean, peanuts), Papilionaceae sp. (for example soya bean), Solanaceae sp. (for example potatoes), Chenopodiaceae sp. (for example sugar beet, fodder beet, swiss chard, beetroot); Malvaceae (for example cotton); useful plants and ornamental plants for gardens and wooded areas; and genetically modified varieties of each of these plants.

More preference is given to controlling the following diseases of soya beans: Fungal diseases on leaves, stems, pods and seeds caused, for example, by *Altemaria* leaf spot (*Altemaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), *leptosphaerulina* leaf spot (*Leptosphaerulina trifoli*), phyllostica leaf spot (*Phyllosticta sojaecola*), pod and stem blight (*Phomopsis sojae*), powdery mildew (*Microsphaera difusa*), pyrenochaeta leaf spot (*Pyrenochaeta glycines*), rhizoctonia aerial, foliage, and web blight (*Rhizoctonia solam*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

The present invention also relates to the use of compounds of formula I, the combinations or the compositions thereof for controlling or preventing the following plant diseases: *Puccinia* spp. (rusts) on various plants, for example, but not limited to *P. triticina* (brown or leaf rust), *P. striiformis* (stripe or yellow rust), *Puccinia melanocephala* (sugarcane rust), *P. hordei* (dwarf rust), *P. graminis* (stem or black rust) or *P. recondita* (brown or leaf rust) on cereals, such as e. g. wheat, barley or rye and *Phakopsoraceae* spp. on various plants, in particular *Phakopsora pachyrhizi* and *P. meibomiae* (soybean rust) on soybeans, *Hemileia vastatrix* (Coffee rust), *Uromyces appendiculatus, Uromyces fabae* and *Uromyces phaseoli* (rust of beans).

The present invention further relates to the use of compounds of formula I, the combinations or the compositions thereof for controlling or preventing against phytopathogenic fungi such as *Phakopsora pachyrhizi, Phakopsora meibomiae*, of agricultural crops and or horticultural crops.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

The invention furthermore includes a method for treating seed, particularly seeds (dormant, primed, pregerminated or even with emerged roots and leaves) treated with at least one of the compounds of the formula (I) and compositions thereof. The inventive seeds are used in methods for protection of seeds and emerged plants from the seeds from phytopathogenic harmful fungi. In these methods, seed treated with at least one inventive active ingredient is used.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which have been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests, microorganisms, weeds or abiotic stress.

The compounds of the formula (I) are suitable for protection of seed of any plant variety which is used in agriculture, in the greenhouse, in forests or in horticulture.

More particularly, the seed is that of cereals (such as wheat, barley, rye, millet and oats), oilseed rape, maize, cotton, soybean, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The compounds of the formula (I) can be applied directly, i.e. without containing any other components and without having been diluted. In general, it is preferable to apply the compositions to the seed in the form of a suitable formulation. Suitable formulations and methods for seed treatment are known to those skilled in the art. The compounds of the formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

In the treatment of seeds to facilitate plantability seeds can be coated with polymer. The polymer coating is comprised of a binder, a wax and a pigment, and one or more stabilizers in an amount effective to stabilize the suspension. The binder can be a polymer selected from the group consisting of vinyl acetate-ethylene copolymer, vinyl acetate homopolymer, vinyl acetate-acrylic copolymer, vinylacrylic, acrylic, ethylene-vinyl chloride, vinyl ether maleic anhydride, or butadiene styrene. Other similar polymers can be used.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutynaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The compounds of the invention and compositions thereof are also suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds. The application of the compounds of the present invention to seeds is a preferred application method.

The application rate of the formulations usable in accordance with the invention can be varied within a relatively wide range. It is guided by the particular content of the active ingredients in the formulations and by the seeds. The application rates of each single active ingredient are generally between 0.001 and 15 g per kilogram of seed, preferably between 0.01 and 5 g per kilogram of seed.

When using the compounds of the formula (I) as fungicides, the application rates can be varied within a relatively wide range, depending on the kind of application. The application rate of the inventive active ingredients is:

in the case of treatment of plant parts, for example leaves: from 0.1 to 10000 g/ha, preferably from 10 to 1000 g/ha, more preferably from 30 to 300 g/ha (in the case of application by watering or dripping, it is even possible to reduce the application rate, especially when inert substrates such as rockwool or perlite are used);

in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;

in the case of soil treatment: from 0.1 to 10000 g/ha, preferably from 1 to 5000 g/ha.

These application rates are merely by way of example and are not limiting for the purposes of the invention.

In some cases, the compounds of the formula (I) can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms).

The compounds of the formula (I) intervene in physiological processes of plants and can therefore also be used as plant growth regulators. Plant growth regulators may exert various effects on plants. The effect of the substances depends essentially on the time of application in relation to the developmental stage of the plant, the plant variety and also on the amounts of active ingredient applied to the plants or their environment and on the type of application. In each case, growth regulators should have a particular desired effect on the crop plants.

Growth regulating effects, comprise earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectolitre weight as well as to improved product quality, comprising: improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.; and further comprising decreased undesired ingredients such as e.g. less mycotoxines, less aflatoxines, geosmin level, phenolic aromas, lacchase, polyphenol oxidases and peroxidases, nitrate content etc.

Plant growth-regulating compounds can be used, for example, to slow down the vegetative growth of the plants. Such growth depression is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, vegetative growth depression allows denser planting, and it is thus possible to achieve higher yields based on the soil surface. Another advantage of the smaller plants obtained in this way is that the crop is easier to cultivate and harvest.

Reduction of the vegetative plant growth may also lead to increased or improved yields because the nutrients and assimilates are of more benefit to flower and fruit formation than to the vegetative parts of the plants.

Alternatively, growth regulators can also be used to promote vegetative growth. This is of great benefit when harvesting the vegetative plant parts. However, promoting vegetative growth may also promote generative growth in that more assimilates are formed, resulting in more or larger fruits.

Furthermore, beneficial effects on growth or yield can be achieved through improved nutrient use efficiency, especially nitrogen (N)-use efficiency, phosphorus (P)-use efficiency, water use efficiency, improved transpiration, respiration and/or $CO_2$ assimilation rate, better nodulation, improved Ca-metabolism etc.

Likewise, growth regulators can be used to alter the composition of the plants, which in turn may result in an improvement in quality of the harvested products. Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Furthermore, growth regulators can modulate plant senescence, which may result in prolonged green leaf area duration, a longer grain filling phase, improved yield quality, etc.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"). In addition, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to synchronize maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

The compounds of the formula (I) also exhibit a potent strengthening effect in plants. Accordingly, they can be used for mobilizing the defences of the plant against attack by undesirable microorganisms.

Plant-strengthening (resistance-inducing) substances in the present context are substances capable of stimulating the defence system of plants in such a way that the treated plants, when subsequently inoculated with undesirable microorganisms, develop a high degree of resistance to these microorganisms.

Further, in context with the present invention plant physiology effects comprise the following: Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc.

Biotic stress tolerance comprising increased fungal resistance and increased resistance against nematodes, viruses and bacteria. In context with the present invention, biotic stress tolerance preferably comprises increased fungal resistance and increased resistance against nematodes.

Increased plant vigor, comprising plant health/plant quality and seed vigor, reduced stand failure, improved appearance, increased recovery after periods of stress, improved pigmentation (e.g. chlorophyll content, stay-green effects, etc.) and improved photosynthetic efficiency.

In addition, the compounds of the formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum (Gibberella zeae), F. equiseti, F. fujikoroi, F. musarum, F. oxysporum, F. proiferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec, and others.

The compounds of the formula (I) can also be used in the protection of materials, for protection of industrial materials against attack and destruction by phytopathogenic fungi.

In addition, the compounds of the formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of the formula (I) may prevent adverse effects, such as rotting, decay, discoloration, decoloration or formation of mould.

In the case of treatment of wood the compounds of the formula (I) may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the compounds of the formula (I) can be used to protect objects which come into contact with saltwater or brackish water, especially hulls, screens, nets, buildings, moorings and signalling systems, from fouling.

The compounds of the formula (I) can also be employed for protecting storage goods. Storage goods are understood to mean natural substances of vegetable or animal origin or processed products thereof which are of natural origin, and for which long-term protection is desired.

Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puelana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp, and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp, and *Saccharomyces* spp., such as *Saccharomyces cerevisae*.

In addition, the compounds of the formula (I) also have very good antimycotic effects. They have a very broad antimycotic activity spectrum, especially against dermatophytes and yeasts, moulds and diphasic fungi (for example against *Candida* species, such as *Candida albicans*, *Candida glabrata*), and *Epidermophyton floccosum*, *Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The enumeration of these fungi by no means constitutes a restriction of the mycotic spectrum covered, and is merely of illustrative character.

The compounds can be used also to control important fungal pathogens in fish and crustacea farming, e.g. saprolegnia diclina in trouts, saprolegnia parasitica in crayfish.

The compounds of the formula (I) can therefore be used both in medical and in non-medical applications.

The compounds of the formula (I) can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

It is possible to treat all plants and their parts in accordance with the invention, preferably with wild plant species and plant cultivars, or those obtained by conventional biological breeding methods, such as crossing or protoplast fusion, and also parts thereof. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—

RNAi—technology or microRNA—miRNA—technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as tobacco plants, with altered post-translational protein modification patterns.

Compounds of the present invention as defined by general formula (I) and/or in table 1 may be prepared, in known manner, in a variety of ways as described in Schemes 1-4.

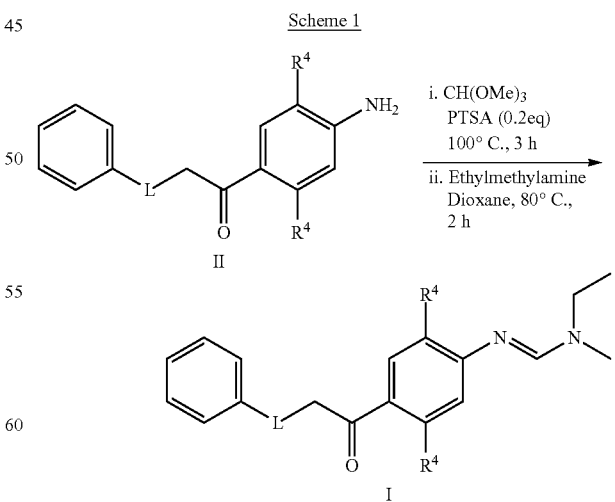

Scheme 1

The compound of formula I can be prepared by treating the corresponding aniline derivative (II) with an excess of trimethylorthoformate using catalytic amount of p-toluensulphonic acid. The resulting intermediate was heated with N-ethylmethyl amine in 1,4 dioxane to get the compound of formula II as mentioned in US20110130282.

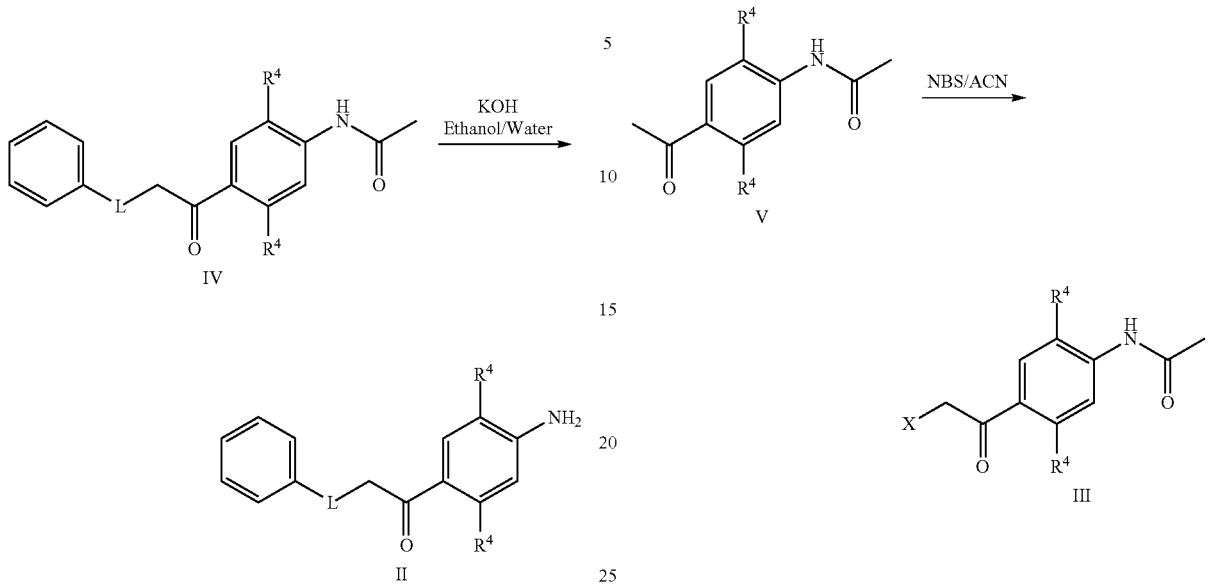

Compounds of formula IV were deprotected to get the aniline derivatives (11) by refluxing in aqueous potassium hydroxide as mentioned in Journal of Physical Chemistry B, 111(20), 5581-5586; 2007

The intermediate III upon treatment with different anilines, phenols or thiophenols under basic condition gives the corresponding compound of formula IV as mentioned in Journal of Organic Chemistry, 45(1), 80-9; 1980 or Journal of Heterocyclic Chemistry, 19(6), 1305-8; 1982.

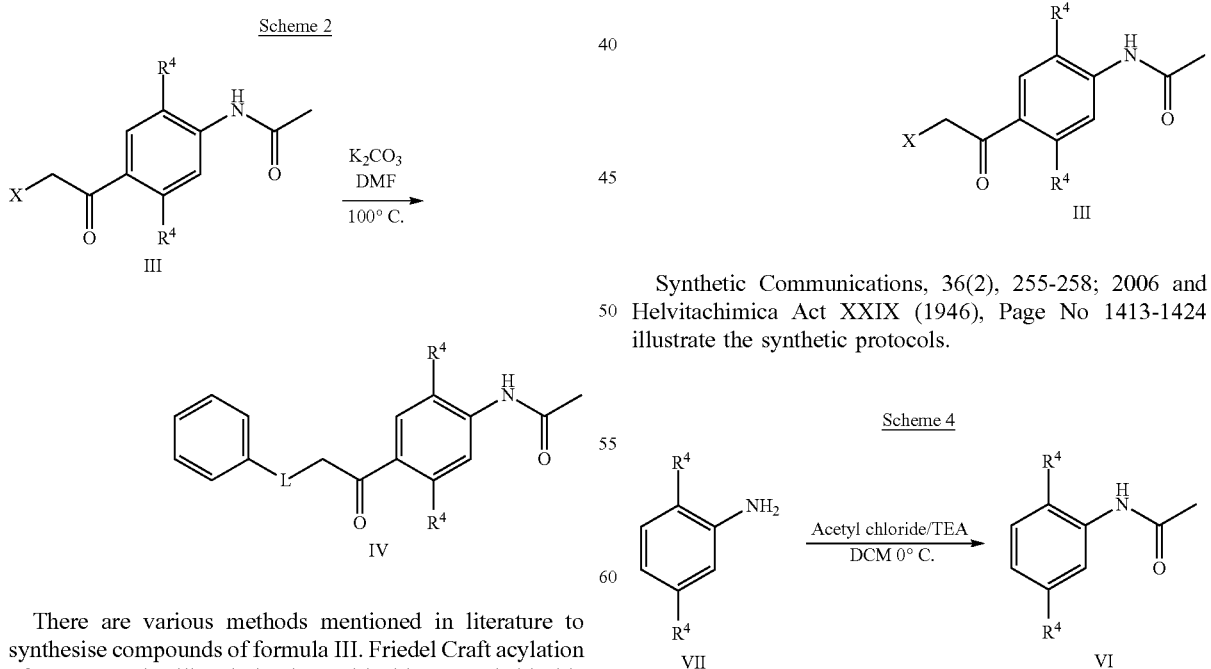

There are various methods mentioned in literature to synthesise compounds of formula III. Friedel Craft acylation of N-protected aniline derivatives with chloroacetyl chloride gives compound of formula III in good yield. Alternatively, bromination of acetyl derivative (V) with N-bromo succinimide gives compound of formula III in good yield.

Synthetic Communications, 36(2), 255-258; 2006 and Helvitachimica Act XXIX (1946), Page No 1413-1424 illustrate the synthetic protocols.

European Journal of Medicinal Chemistry (2014), 83, 569-580, illustrates the synthetic protocols.

General Scheme

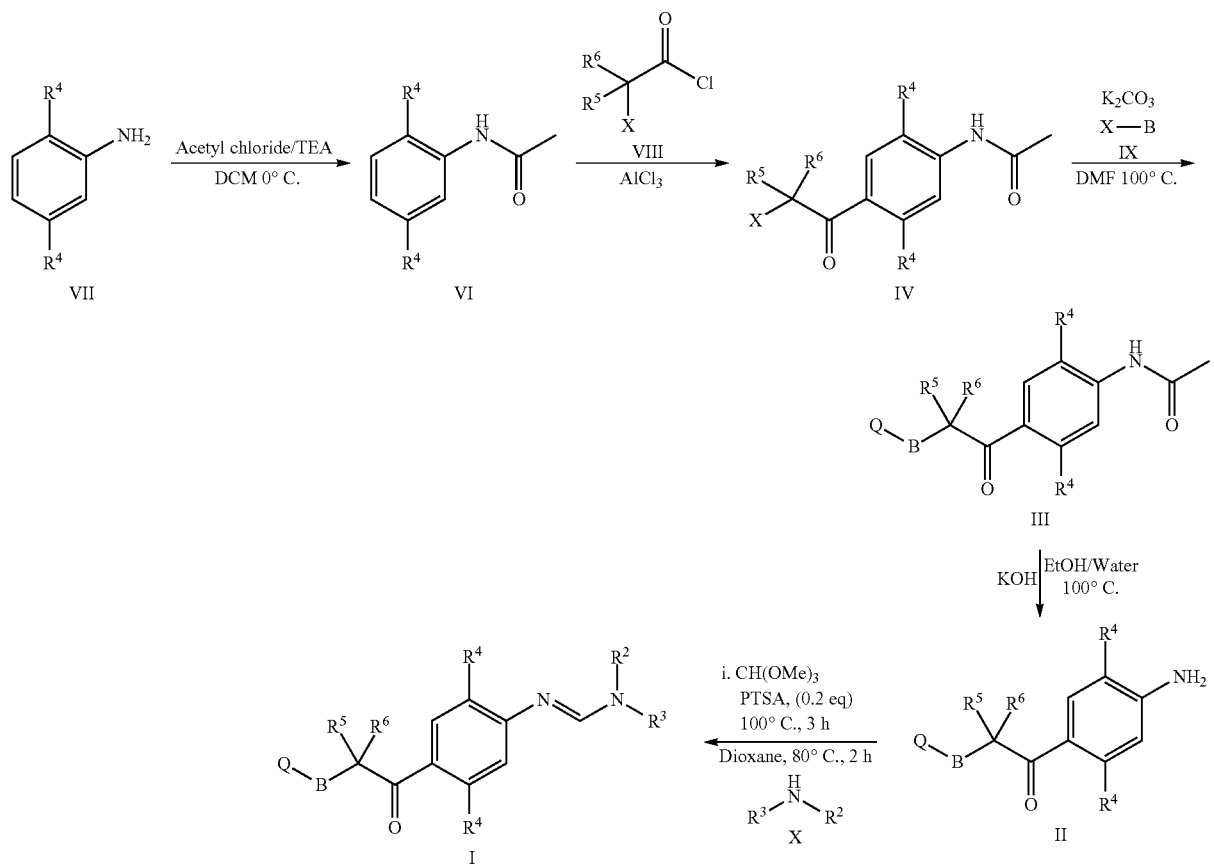

Procedure:

Preparation of Compound VI Step-A

To a stirred solution of compound VII in dichloromethane, triethyl amine and acetyl chloride were added at 0° C. The reaction mixture was stirred for 2 h at 0° C. After completion of reaction, the reaction mixture was poured into water. The aqueous layer was extracted with dichloromethane. The dichloromethane layer was separated and washed with water and brine solution. The organic layer was separated and dried over anhydrous sodium sulphate, filtered and evaporated under reduced pressure to give the desired compound VI Preparation of Compound IV Step-B To a mixture of compound VI and aluminium chloride, compound VIII was added slowly at 0° C. The reaction mixture was stirred at 0° C. for h. After completion of reaction, the reaction mixture was quenched cautiously by addition of water and the aqueous layer was extracted with dichloromethane. The organic layer was separated and washed with brine solution. The organic layer was dried over anhydrous sodium sulphate, filtered and evaporated under reduced pressure to obtain a crude solid. The solid was washed with bicarbonate solution to remove any acidic impurities to get the desired compound IV.

Preparation of Compound III Step-C

To a stirred solution of compound IV in N,N-dimethylformamide compound IX and potassium carbonate were added. The reaction mixture was stirred for 2 h at 100° C. After completion of the reaction, the reaction mixture was cooled to room temperature and poured into water. The aqueous mixture was extracted with ethyl acetate. The organic layers were collected and washed with water and brine solution. The organic layer was dried over sodium sulphate, filtered and evaporated to get crude compound which was purified by flash chromatography using ethyl acetate and hexane as eluent to get the desired compound III.

Preparation of Compound II Step-D

To a stirred solution of compound III in ethanol and water, potassium hydroxide was added at room temperature. The reaction mixture was stirred for 2 h at 100° C. After completion of the reaction, the volatiles were evaporated. The residue was cooled to room temperature, diluted with water and extracted with dichloromethane. The combined organic layers were washed with water and brine solution. The organic layer was separated, dried over sodium sulphate, filtered and evaporated at reduced pressure to get the desired compound II.

Preparation of Compound I Step-E

To a stirred solution of compound II in trimethylorthoformate, p-toluenesulfonic acid monohydrate was added, and the resulting mixture was stirred at 105° C. for 2 h. After the complete conversion of the aniline derivative, the volatiles were evaporated to give the intermediate. This intermediate was dissolved in 1,4 dioxane, compound X was added and the mixture was stirred for 2 h at 105° C. After completion of the reaction, the reaction mixture was evaporated to give the crude compound, which was purified by preparative HPLC to get the desired compound I.

Example 1: Preparation of N-ethyl-N'-(4-(2-((3-fluorophenyl)thio)acetyl)-2,5-dimethylphenyl)-N-methylformimidamide Step-A Preparation of N-(2,5-Dimethylphenyl)Acetamide To a stirred solution of 2,5-dimethylaniline (50 g, 413 mmol) in dichloromethane (500 ml), triethylamine (144 ml, 1031 mmol) and acetyl chloride (35.2 ml, 495 mmol) were added at 0° C. The reaction mixture was stirred for 2 h at 0° C. After completion of the reaction, the reaction mixture was poured into water. The aqueous layer was extracted with dichloromethane (3×1000 mL). The combined dichloromethane layers were separated and washed with water (2×500 mL) and brine solution (1×250 mL). The organic layer was separated and dried over anhydrous sodium sulphate, filtered and evaporated under high vacuum to give the desired N-(2,5-dimethylphenyl)acetamide (60 g, 368 mmol, 89% yield). LCMS (M+H): 165.50

Step B: Preparation of N-(4-(2-chloroacetyl)-2,5-dimethylphenyl)acetamide

To a mixture of N-(2,5-dimethylphenyl)acetamide (7.0 g, 42.9 mmol) and aluminum chloride (17.15 g, 129 mmol), chloroacetyl chloride (17.18 ml, 214 mmol) was added slowly at 0° C. The reaction mixture was stirred at 0° C. for 1 h. After completion of the reaction, the reaction mixture was quenched cautiously by addition of water and the aqueous layer was extracted with dichloromethane (3×250 mL). The organic layer was separated and washed with brine solution (1×250 mL). The organic layer was dried over anhydrous sodium sulphate, filtered and evaporated under high vacuum to obtain a crude solid. The solid was washed with bicarbonate solution to remove any acidic impurities to get the desired N-(4-(2-chloroacetyl)-2,5-dimethylphenyl)acetamide (8.5 g, 35.5 mmol, 83% yield). LCMS (M+H): 240.70

Step C: Preparation of N-(4-(2-((3-fluorophenyl)thio)acetyl)-2,5-dimethylphenyl)acetamide To a stirred solution of N-(4-(2-chloroacetyl)-2,5-dimethylphenyl)acetamide (0.7 g, 2.92 mmol) in N,N-dimethylformamide (7 ml), 3-fluorobenzenethiol (0.561 g, 4.38 mmol) and potassium carbonate (1.009 g, 7.30 mmol) were added. The reaction mixture was stirred for 2 h at 100° C. After completion of the reaction, the reaction mixture was cooled to room temperature and poured into water. The aqueous mixture was extracted with ethyl acetate (3×200 mL). The organic layers were collected and washed with water (2×100 mL) and brine solution (1×100 mL). The organic layer was dried over anhydrous sodium sulphate, filtered and evaporated to get the crude compound which was purified by flash chromatography using ethyl acetate and hexane as eluent to get desired N-(4-(2-((3-fluorophenyl)thio)acetyl)-2,5-dimethylphenyl)acetamide (0.5 g, 1.509 mmol, 52% yield). LCMS (M+H): 332.40

Step D: Preparation of 1-(4-amino-2,5-dimethylphenyl)-2-((3-fluorophenyl)thio)ethan-1-one To a stirred solution of N-(4-(2-((3-fluorophenyl)thio)acetyl)-2,5-dimethylphenyl)acetamide (0.5 g, 1.509 mmol) in ethanol (5 ml) and water (5 ml) potassium hydroxide (2.54 g, 45.3 mmol) was added at room temperature. The reaction mixture was stirred for 2 h at 100° C. After completion of the reaction, the volatiles were evaporated. The residue was cooled to room temperature, diluted with water and extracted with dichloromethane (3×100 mL). The combined organic layers were washed with water (1×100 mL) and brine solution (1×100 mL). The organic layer was separated, dried over anhydrous sodium sulphate, filtered and evaporated at high vacuum to get the desired 1-(4-amino-2,5-dimethylphenyl)-2-((3-fluorophenyl)thio)ethan-1-one (0.4 g, 1.382 mmol, 92% yield). LCMS (M+H): 290.30

Step E: Preparation of N-ethyl-N'-(4-(2-((3-fluorophenyl)thio)acetyl)-2,5-dimethylphenyl)-N-methylformimidamide To a stirred solution of 1-(4-amino-2,5-dimethylphenyl)-2-((3-fluorophenyl)thio)ethan-1-one (0.45 g, 1.555 mmol) in trimethylorthoformate (10 ml) p-toluenesulfonic acid monohydrate (2.96 mg, 0.016 mmol) was added, and the resulting mixture was stirred at 105° C. for 2 h. After the complete conversion of the aniline derivative, the volatiles were evaporated to give the intermediate. This intermediate was dissolved in 1,4 dioxane (10 ml), N-ethylmethylamine (1.35 ml, 15.55 mmol) was added and the mixture was stirred for 2 h at 105° C. After completion of the reaction, the reaction mixture was evaporated to give the crude compound, which was purified by preparative HPLC to get the desired N-ethyl-N'-(4-(2-((3-fluorophenyl)thio)acetyl)-2,5-dimethylphenyl)-N-methylformimidamide (222 mg, 0.619 mmol, 40% yield). $^1$H-NMR (400 MHz, DMSO-D6) δ 7.78 (d, 2H), 7.67 (s, 1H), 7.34-7.28 (m, 1H), 7.18-7.22 (m, 1H), 7.14 (d, 1H), 6.96-7.00 (m, 1H), 6.69 (d, 1H), 4.62 (s, 2H), 3.51-3.33 (2H), 3.06-2.89 (3H), 2.32 (s, 3H), 2.19 (s, 3H), 1.13 (t, 3H), LCMS (M+H): 359.48.

Example 3: Preparation of N'-(4-(2-((3-chloro-5-(trifluoromethyl)pyridin-2-yl)thio)acetyl)-2,5-dimethylphenyl)-N-ethyl-N-methylformimidamide Step A-D Carried Out According to the Procedure Described for General Scheme To a stirred solution of 1-(4-amino-2,5-dimethylphenyl)-2-((3-chloro-5-(trifluoromethyl)pyridin-2-yl)thio)ethan-1-one (0.25 g, 0.667 mmol) in trimethylorthoformate (10 ml) p-toluenesulfonic acid monohydrate (6.34 mg, 0.033 mmol) was added, and the resulting mixture was stirred at 105° C. for 2 h. After the complete conversion of the aniline derivative, the volatiles were evaporated to give the intermediate. This intermediate was dissolved in 1,4 dioxane (10 ml), N-ethylmethylamine (0.394 g, 6.67 mmol) was added and the mixture was stirred for 2 h at 105° C. After completion of the reaction, the reaction mixture was evaporated to give the crude compound, which was purified by preparative HPLC to get the desired N'-(4-(2-((3-chloro-5-(trifluoromethyl)pyridin-2-yl)thio)acetyl)-2,5-dimethylphenyl)-N-ethyl-N-methylformimidamide (152 mg, 0.342 mmol, 51% yield). $^1$H-NMR (400 MHz, DMSO-D6) S 8.69 (q, 1H), 8.35 (d, 1H), 7.85-7.62 (2H), 6.77-6.65 (bs, H), 4.79 (s, 2H), 3.51-3.34 (2H), 3.50-3.29 (2H), 3.06-2.90 (3H), 2.33 (s, 3H), 2.21 (s, 3H), 1.14 (t, J=6.7 Hz, 3H), LCMS (M+H): 444.54

Example 4: Preparation of N'-(2-chloro-5-methyl-4-(2-(m-tolylthio)acetyl)phenyl)-N-ethyl-N-methyl-formimidamide Step A-D Carried Out According to the Procedure Described for General Scheme To a stirred solution of 1-(4-amino-5-chloro-2-methylphenyl)-2-(m-tolylthio)ethan-1-one (0.3 g, 0.981 mmol) in trimethylorthoformate (10 ml) p-toluenesulfonic acid monohydrate (9.33 mg, 0.049 mmol) was added, and the resulting mixture was stirred at 105° C. for 2 h. After the complete conversion of the aniline derivative, the volatiles were evaporated to give the intermediate. This intermediate was dissolved in 1,4 dioxane (10 ml), N-ethylmethylamine (0.580 g, 9.81 mmol) was added and the mixture was stirred for 2 h at 105° C. After completion of the reaction, the reaction mixture was evaporated to give the crude compound, which was purified by preparative HPLC to get the desired N'-(2-chloro-5-methyl-4-(2-(m-tolylthio)acetyl)phenyl)-N-ethyl-N-methylformimidamide (0.234 g, 0.624 mmol, 64% yield). $^1$H-NMR (400 MHz, DMSO-D6) 7.94 (s, 1H), 7.77-7.86 (I H), 7.09-7.18 (m, 3H), 6.99 (d, 1H), 6.89 (d, 1H), 4.50 (s, 2H), 3.54-3.34 (2H), 3.09-2.89 (3H), 2.27 (s, 3H), 2.24 (s, 3H), 1.11-1.18 (m, 3H). LCMS (M+H): 375.15

Example 5: Preparation of N'-(4-(2-((3,4-dimethylphenyl)thio)acetyl)-2,5-dimethylphenyl)-N-isopropyl-N-methylformimidamide Step A-D Carried Out According to the Procedure Described for General Scheme To a stirred solution of 1-(4-amino-2,5-dimethylphenyl)-2-((3,4-dimethylphenyl)thio)ethan-1-one (0.3 g, 1.002 mmol) in trimethylorthoformate (6 ml) p-toluenesulfonic acid monohydrate (0.038 g, 0.200 mmol) was added, and the resulting mixture was stirred at 105° C. for 2 h. After the complete conversion of the aniline derivative, the volatiles were evaporated to give the intermediate. This intermediate was dissolved in 1,4 dioxane (6 ml), N-methylpropan-2-amine (0.366 g, 5.01 mmol) was added and the mixture was stirred for 2 h at 105° C. After completion of the reaction, the reaction mixture was evaporated to give the crude compound, which was purified by preparative HPLC to get the desired N'-(4-(2-((3,4-dimethylphenyl)thio)acetyl)-2,5-dimethylphenyl)-N-isopropyl-N-methylformimidamide (0.187 g, 0.489 mmol, 49% yield). $^1$H-NMR (400 MHz, DMSO-D6) δ 7.90-7.60 (2H), 7.10 (s, 1H), 7.05 (d, 2H), 6.68 (s, 1H), 4.37 (s, 2H), 3.80-3.86 (m, 1H), 2.86 (s, 3H), 2.30 (s, 3H), 2.17 (d, 9H), 1.18-1.22 (m, 7H). LCMS (M+H): 383.50

Example 6: Preparation of N-allyl-N'-(4-(2-((3,4-dimethylphenyl)thio)acetyl)-2,5-dimethylphenyl)-N-methylformimidamide Step A-D Carried Out According to the Procedure Described for General Scheme To a stirred solution of 1-(4-amino-2,5-dimethylphenyl)-2-((3,4-dimethylphenyl)thio)ethan-1-one (0.3 g, 1.002 mmol) in trimethylorthoformate (6 ml) p-toluenesulfonic acid monohydrate (0.038 g, 0.200 mmol) was added, and the resulting mixture was stirred at 105° C. for 2 h. After the complete conversion of the aniline derivative, the volatiles were evaporated to give the intermediate. This intermediate was dissolved in 1,4 dioxane (6 ml), N-methylprop-2-en-1-amine (0.356 g, 5.01 mmol) was added and the mixture was stirred for 2 h at 105° C. After completion of the reaction, the reaction mixture was evaporated to give the crude compound, which was purified by preparative HPLC to get the desired N-allyl-N'-(4-(2-((3,4-dimethylphenyl)thio)acetyl)-2,5-dimethylphenyl)-N-methylformimidamide (0.199 g, 0.523 mmol, 52% yield). $^1$H-NMR (400 MHz, DMSO-D6) δ 7.77 (d, 1H), 7.64 (s, 1H), 7.10 (s, 1H), 7.04 (d, 2H), 6.68 (s, 1H), 5.86 (s, 1H), 5.19-5.24 (m, 2H), 4.37 (s, 2H), 3.94-4.06 (m, 2H), 3.04-2.84 (3H), 2.30 (s, 3H), 2.15 (s, 9H). LCMS (M+H): 381.4

Example 7: Preparation of 1-(2,5-dimethyl-4-((morpholinomethylene)amino)phenyl)-2-((3,4-dimethylphenyl)thio)ethan-1-one Step A-D Carried Out According to the Procedure Described for General Scheme To a stirred solution of 1-(4-amino-2,5-dimethylphenyl)-2-((3,4-dimethylphenyl)thio)ethan-1-one (0.3 g, 1.002 mmol) in trimethylorthoformate (6 ml) p-toluenesulfonic acid monohydrate (0.038 g, 0.200 mmol) was added, and the resulting mixture was stirred at 105° C. for 2 h. After the complete conversion of the aniline derivative, the volatiles were evaporated to give the intermediate. This intermediate was dissolved in 1,4 dioxane (6 ml), morpholine (0.436 g, 5.01 mmol) was added and the mixture was stirred for 2 h at 105° C. After completion of the reaction, the reaction mixture was evaporated to give the crude compound, which was purified by preparative HPLC to get the desired 1-(2,5-dimethyl-4-((morpholinomethylene)amino)phenyl)-2-((3,4-dimethylphenyl)thio)ethan-1-one (0.144 g, 0.363 mmol, 36% yield). $^1$H-NMR (400 MHz, DMSO-D6) δ 7.75 (s, 1H), 7.62 (s, 1H), 7.08 (s, 1H), 7.02 (d, 2H), 6.68 (s, 1H), 4.35 (s, 2H), 3.63-3.34 (8H), 2.27 (s, 3H), 2.14-2.11 (9H). LCMS (M+H): 397.3

Example 8: Preparation of 1-(2,5-dimethyl-4-((thiomorpholinomethylene)amino)phenyl)-2-((3,4-dimethylphenyl)thio)ethan-1-one Step A-D Carried Out According to the Procedure Described for General Scheme To a stirred solution of 1-(4-amino-2,5-dimethylphenyl)-2-((3,4-dimethylphenyl)thio)ethan-1-one (0.225 g, 0.751 mmol) in trimethylorthoformate (5 ml) p-toluenesulfonic acid monohydrate (0.029 g, 0.150 mmol) was added, and the resulting mixture was stirred at 100° C. for 2 h. After the complete conversion of the aniline derivative, the volatiles were evaporated to give the intermediate. This intermediate was dissolved in 1,4 dioxane (5 ml), thiomorpholine (0.155 g, 1.503 mmol) was added and the mixture was stirred for 2 h at 105° C. After completion of the reaction, the reaction mixture was evaporated to give the crude compound, which was purified by preparative HPLC to get the desired 1-(2,5-dimethyl-4-((thiomorpholinomethylene)amino)phenyl)-2-((3,4-dimethylphenyl)thio)ethan-1-one (0.120 g, 0.291 mmol, 39% yield). $^1$H-NMR (400 MHz, DMSO-D6) δ 7.74 (s, 1H), 7.65 (s, 1H), 7.10 (s, 1H), 7.04 (d, 2H), 6.70 (s, 1H), 4.38 (s, 2H), 3.77 (d, 4H), 2.64 (s, 4H), 2.29 (s, 3H), 2.15 (s, 6H), 2.14 (s, 3H). LCMS (M+H): 413.50

Example 9: Preparation of N'-(2,5-dimethyl-4-(2-phenoxyacetyl)phenyl)-N-ethyl-N-methylformimidamide Step A, and Step B were Carried Out as Mentioned in Example 1

Step C: Preparation of Desired N-(2,5-dimethyl-4-(2-phenoxyacetyl)phenyl)acetamide To a stirred solution of N-(4-(2-chloroacetyl)-2,5-dimethylphenyl)acetamide (0.8 g, 3.34 mmol) in N,N-dimethylformamide (6 ml), sodium hydride (0.160 g, 6.68 mmol) was added at 0° C. under nitrogen atmosphere. The reaction mass was stirred for 10 min at 0° C. Phenol (0.471 g, 5.01 mmol) was added and the reaction was stirred for 30 min at 0° C. After completion of the reaction, the reaction mixture was poured into ice cold water cautiously and extracted with ethyl acetate (3×100 mL). The combined ethyl acetate layers were washed with water (2×100 mL) and brine solution (1×100 mL). The organic layer was dried over anhydrous sodium sulphate, filtered and evaporated under high vacuum to get the crude compound which was purified by flash chromatography using ethyl acetate and hexane as eluent to obtain the desired N-(2,5-dimethyl-4-(2-phenoxyacetyl) phenyl)acetamide (0.5 g, 1.681 mmol, 50% yield). LCMS (M+H): 298.35

Step D: Preparation of 1-(4-amino-2,5-dimethylphenyl)-2-phenoxyethan-1-one

To a stirred solution of N-(2,5-dimethyl-4-(2-phenoxyacetyl)phenyl)acetamide (0.45 g, 1.513 mmol) in ethanol (3 ml) and water (3 ml), potassium hydroxide (2.55 g, 45.4 mmol) was added. The reaction mixture was stirred for 2 h at 100° C. After completion of the reaction, the reaction mixture was diluted with water and extracted with dichloromethane (3×100 mL). The organic layers were combined and washed with water (2×100 mL) and brine solution (1×100 mL). The organic layer was separated and dried over anhydrous sodium sulphate. The organic layer was filtered and evaporated to get the desired 1-(4-amino-2,5-dimethylphenyl)-2-phenoxyethan-1-one (0.3 g, 1.175 mmol, 78% yield). LCMS (M+H): 256.32

Step E: Preparation of N'-(2,5-dimethyl-4-(2-phenoxyacetyl)phenyl)-N-ethyl-N-methylformimidamide To a stirred solution of 1-(4-amino-2,5-dimethylphenyl)-2-phenoxyethan-1-one (0.3 g, 1.175 mmol) in trimethylorthoformate (10 ml) p-toluenesulfonic acid monohydrate (2.235 mg, 0.012 mmol) was added, and the resulting mixture was stirred at 105° C. for 2 h. After the complete conversion of the aniline derivative, the volatiles were evaporated to give the intermediate. This intermediate was dissolved in 1,4 dioxane (10 ml), N-ethylmethylamine (1 ml, 11.75 mmol) was added and the mixture was stirred for 2 h at 105° C. After completion of the reaction, the reaction mixture was evaporated to give the crude compound, which was purified by preparative HPLC to get the desired N'-(2,5-dimethyl-4-(2-phenoxyacetyl)phenyl)-N-ethyl-N-methylformimidamide (190 mg, 0.586 mmol, 50% yield). $^1$H-NMR (400 MHz, DMSO-D6) δ 7.68-7.79 (m, 2H), 7.23-7.29 (m, 2H), 6.89-6.93 (m, 3H), 6.71 (d, 1H), 5.33 (s, 2H), 3.52-3.33 (2H), 3.07-2.88 (3H), 2.53 (d, 1H), 2.38 (s, 3H), 2.20 (s, 3H), 1.14 (t, 3H). LCMS (M+H): 325.5

Example 10: Preparation of N'-(2,5-dimethyl-4-(2-(3-((perfluoroethyl)thio)phenoxy)acetyl)phenyl)-N-ethyl-N-methylformimidamide Step A-D Carried Out According to the Procedure Described for General Scheme To a stirred solution of 1-(4-amino-2,5-dimethylphenyl)-2-(3-((perfluoroethyl)thio)phenoxy)ethan-1-one (0.3 g, 0.740 mmol) in trimethylorthoformate (6 ml) p-toluenesulfonic acid monohydrate (0.028 g, 0.148 mmol) was added, and the resulting mixture was stirred at 105° C. for 2 h. After the complete conversion of the aniline derivative, the volatiles were evaporated to give the intermediate. This intermediate was dissolved in 1,4 dioxane (6 ml), N-ethylmethylamine (0.437 g, 7.40 mmol) was added and the mixture was stirred for 2 h at 105° C. After completion of the reaction, the reaction mixture was evaporated to give the crude compound, which was purified by preparative HPLC to get the desired N'-(2,5-dimethyl-4-(2-(3-((perfluoroethyl)thio)phenoxy)acetyl)phenyl)-N-ethyl-N-methylformimidamide (0.135 g, 0.285 mmol, 38% yield). $^1$H-NMR (400 MHz, DMSO-D6) δ 7.68-7.80 (m, 2H), 7.43 (t, 1H), 7.17-7.27 (m, 3H), 6.72 (d, 1H), 5.48 (s, 2H), 3.57-3.34 (2H), 3.09-2.80 (3H), 2.37 (s, 3H), 2.21 (s, 3H), 1.12-1.16 (m, 3H). LCMS (M+H): 475.5

Example 11: Preparation of N'-(4-(2-(3-bromophenoxy)acetyl)-2,5-dimethylphenyl)-N-ethyl-N-methylformimidamide Step A-D Carried Out According to the Procedure Described for General Scheme To a stirred solution of 1-(4-amino-2,5-dimethylphenyl)-2-(3-bromophenoxy)ethan-1-one (0.4 g, 1.197 mmol) in trimethylorthoformate (15 ml) p-toluenesulfonic acid monohydrate (4.55 mg, 0.024 mmol) was added, and the resulting mixture was stirred at 105° C. for 2 h. After the complete conversion of the aniline derivative, the volatiles were evaporated to give the intermediate. This intermediate was dissolved in 1,4 dioxane (15 ml), N-ethylmethylamine (1.021 ml, 11.75 mmol) was added and the mixture was stirred for 2 h at 105° C. After completion of the reaction, the reaction mixture was evaporated to give the crude compound, which was purified by preparative HPLC to get the desired N'-(4-(2-(3-bromophenoxy)acetyl)-2,5-dimethylphenyl)-N-ethyl-N-methylformimidamide (91 mg, 0.226 mmol, 19% yield). $^1$H-NMR (400 MHz, DMSO-D6) δ 7.69-7.81 (m, 2H), 7.23 (t, 1H), 7.11-7.16 (m, 2H), 6.93-6.96 (m, 1H), 6.74 (s, 1H), 5.43 (s, 2H), 3.55-3.34 (2H), 3.10-2.84 (3H), 2.39 (s, 3H), 2.21 (s, 3H), 1.13-1.17 (m, 3H). LCMS (M+H): 404.23

Example 12: Preparation of N'-(4-(2-(3-(dimethylamino)phenoxy)acetyl)-2,5-dimethylphenyl)-N-ethyl-N-methylformimidamide Step A-D Carried Out According to the Procedure Described for General Scheme To a stirred solution of 1-(4-amino-2,5-dimethylphenyl)-2-(3-(dimethylamino)phenoxy)ethan-1-one (0.28 g, 0.938 mmol) in trimethylorthoformate (6 ml) p-toluenesulfonic acid monohydrate (0.036 g, 0.188 mmol) was added, and the resulting mixture was stirred at 100° C. for 2 h. After the complete conversion of the aniline derivative, the volatiles were evaporated to give the intermediate. This intermediate was dissolved in 1,4 dioxane (6 ml), N-ethylmethylamine (0.555 g, 9.38 mmol) was added and the mixture was stirred for 2 h at 105° C. After completion of the reaction, the reaction mixture was evaporated to give the crude compound, which was purified by preparative HPLC to get the desired N'-(4-(2-(3-(dimethylamino)phenoxy)acetyl)-2,5-dimethylphenyl)-N-ethyl-N-methylformimidamide (0.141 g, 0.384 mmol, 41% yield). $^1$H-NMR (400 MHz, DMSO-D6) δ 7.67-7.80 (m, 2H), 7.02 (t, 1H), 6.74 (s, 1H), 6.30 (d, 1H), 6.19 (d, 2H), 5.24 (s, 2H), 3.51-3.34 (2H), 3.05-2.90 (3H), 2.84 (d, 6H), 2.83-2.83 (OH), 2.37 (s, 3H), 2.19 (s, 3H), 1.10-1.16 (m, 3H). LCMS (M+H): 368.1

Example 13: Preparation of N'-(2,5-dimethyl-4-(2-methyl-2-(m-tolyloxy)propanoyl)phenyl)-N-ethyl-N-methylformimidamide Step A was Carried Out as Mentioned in Example 1

Step B: Preparation of N-(4-isobutyryl-2,5-dimethylphenyl)acetamide

To a mixture of N-(2,5-dimethylphenyl)acetamide (5.0 g, 30.6 mmol) and aluminum chloride (12.25 g, 92 mmol), isobutyryl chloride (6.53 ml, 61.3 mmol) was added slowly at 0° C. The reaction mixture was stirred at 0° C. for 1 h. After completion of the reaction, the reaction mixture was quenched cautiously by addition of cold water. The aqueous layer was extracted with dichloromethane (3×200 mL). The organic layer was separated, washed with brine solution (1×200 mL). The organic layer was dried over anhydrous sodium sulphate, filtered and evaporated under high vacuum to obtain a crude solid. The solid was washed with sodium bicarbonate solution to remove any acidic impurities to get desired N-(4-isobutyryl-2,5-dimethylphenyl)acetamide (4.0 g, 17.4 mmol, 56% yield). LCMS (M+)=234.35

Step C: Preparation of N-(4-(2-bromo-2-methylpropanoyl)-2,5-dimethylphenyl)acetamide To a solution of N-(4-(2-bromo-2-methylpropanoyl)-2,5-dimethylphenyl)acetamide (4.0 g, 17.14 mmol) in acetic acid (40 ml), Bromine (0.88 ml, 17.14 mmol) was added slowly at room temperature. The reaction mixture was stirred at RT for 2 h. After completion of the reaction, the reaction mixture was quenched cautiously by addition of sodium thiosulphate. The volatiles were evaporated; the residue was diluted with water (100 ml). The aqueous mixture was extracted with dichloromethane (3×150 mL). The combined organic layers were collected and washed with sodium hydroxide solution (1×200 mL). The organic layer was dried over anhydrous sodium sulphate, filtered and evaporated under high vacuum to obtain a crude N-(4-(2-bromo-2-methylpropanoyl)-2,5-dimethylphenyl)acetamide (4.0 g, 12.81 mmol, 75% yield). LCMS (M+): 313.25

Step D: Preparation of desired N-(2,5-dimethyl-4-(2-phenoxyacetyl)phenyl)acetamide To a stirred solution of N-(4-(2-bromo-2-methylpropanoyl)-2,5-dimethylphenyl)acetamide (1 g, 3.20 mmol) in N,N-dimethylformamide (6 ml) potassium carbonate (1.1 g, 8.01 mmol) was added at 0° C. under nitrogen atmosphere. The reaction mass was stirred for 10 min at room temperature. m-cresol (0.41 g, 5.01 mmol) was added and the reaction was stirred for 30 min at 0° C. After completion of the reaction, the reaction mixture was poured cautiously into ice cold water and the aqueous mixture was extracted with ethyl acetate (3×100 mL). The combined ethyl acetate layers were collected and washed with water (2×100 mL) and brine solution (1×100 mL). The organic layer was dried over anhydrous sodium sulphate, filtered and evaporated under high vacuum to get a crude compound which was purified by prep HPLC to obtain the desired N-(2,5-dimethyl-4-(2-methyl-2-(m-tolyloxy)propanoyl)phenyl)acetamide (0.45 g, 1.326 mmol, 42% yield). LCMS (M+): 339.41

Step-E Preparation of 1-(4-amino-2,5-dimethylphenyl)-2-methyl-2-(m-tolyloxy)propan-1-one To a stirred solution of N-(2,5-dimethyl-4-(2-methyl-2-(m-tolyloxy)propanoyl)phenyl)acetamide (0.45 g, 1.17 mmol) in ethanol (4 ml) and water (4.00 ml), potassium hydroxide (1.32 g, 23.57 mmol) was added added at room temperature. The reaction mixture was stirred for 2 h at 85° C. After completion of the reaction, the reaction mixture was diluted with water and extracted with dichloromethane (3×50 mL). The combined organic layers were washed with water (2×100 mL) and brine solution (1×100 mL). The organic layer was separated, dried over anhydrous sodium sulphate, filtered and evaporated at reduced pressure to get the desired 1-(4-amino-2,5-dimethylphenyl)-2-methyl-2-(m-tolyloxy)propan-1-one (0.3 g, 1.009 mmol, 86% yield). LCMS (M+): 298.50

Step F: Preparation of N'-(2,5-dimethyl-4-(2-methyl-2-(m-tolyloxy)propanoyl)phenyl)-N-ethyl-N-methylformimidamide To a stirred solution of 1-(4-amino-2,5-dimethylphenyl)-2-methyl-2-(m-tolyloxy)propan-1-one (0.3 g, 1.009 mmol) in trimethylorthoformate (6 ml) p-toluenesulfonic acid monohydrate (0.038 g, 0.202 mmol) was added, and the resulting mixture was stirred at 100° C. for 2 h. After the complete conversion of the aniline derivative, the volatiles were evaporated to give the intermediate. This intermediate was dissolved in 1,4 dioxane (6 ml), N-ethylmethylamine (0.596 g, 10.09 mmol) was added and the mixture was stirred for 2 h at 105° C. After completion of the reaction, the reaction mixture was evaporated to give the crude compound, which was purified by preparative HPLC to get the desired N'-(2,5-dimethyl-4-(2-methyl-2-(m-tolyloxy)propanoyl)phenyl)-N-ethyl-N-methylformimidamide (0.18 g, 0.491 mmol, 49% yield). $^1$H-NMR (400 MHz, DMSO-D6) δ 7.87 (s, 1H), 7.73 (s, 1H), 7.04 (t, 1H), 6.67-6.71 (m, 2H), 6.54 (s, 1H), 6.49 (dd, 1H), 3.47-3.32 (2H), 3.03-2.85 (3H), 2.35 (s, 3H), 2.17 (s, 3H), 2.08 (s, 3H), 1.58 (s, 6H), 1.10 (q, 3H). LCMS (M+H): 367.65.

Example 14: Preparation of N'-(2,5-dimethyl-4-(N-methyl-N-phenylglycyl)phenyl)-N-ethyl-N-methylformimidamide Step A: Preparation of N-methylaniline To a stirred solution of N-methyl-N-phenylacetamide (1.0 g, 6.70 mmol) in 50% aq ethanol (5 ml) potassium hydroxide (7.52 g, 134 mmol) was added at room temperature. The reaction mixture was allowed to stir for 2 h at 80° C. After completion of the reaction, the reaction mixture was diluted with water and extracted with dichloromethane (3×100 mL). The combined organic layers were washed with water (2×100 mL) and brine solution (1×100 mL). The organic layer was separated, dried over anhydrous sodium sulphate, filtered and evaporated get the desired N-methylaniline (0.6 g, 5.60 mmol, 84% yield).

Step B: Preparation of N-(4-(2-chloroacetyl)-2,5-dimethylphenyl)acetamide

To a mixture of N-(2,5-dimethylphenyl)acetamide (7.0 g, 42.9 mmol) and aluminum chloride (17.15 g, 129 mmol), chloroacetyl chloride (17.18 ml, 214 mmol) was added at 0° C. The reaction mixture was stirred at 0° C. for 1 h. After compilation of the reaction, the reaction mixture was quenched cautiously by addition of water and the aqueous layer was extracted with dichloromethane (3×250 mL). The combined organic layers were washed with water (2×100 mL) and brine solution (1×100 mL). The organic layer was separated, dried over anhydrous sodium sulphate, filtered and evaporated under reduced pressure to obtain a crude solid. The solid was washed with bicarbonate solution to get the desired N-(4-(2-chloroacetyl)-2,5-dimethylphenyl)acetamide (8.5 g, 35.5 mmol, 83% yield).

Step C: Preparation of desired N-(2,5-dimethyl-4-(N-methyl-N-phenylglycyl)phenyl)acetamide To a stirred solution of N-(4-(2-chloroacetyl)-2,5-dimethylphenyl)acetamide (0.8 g, 3.34 mmol) in N,N-dimethylformamide (8 ml) sodium bicarbonate (0.56 g, 6.68 mmol) and potassium iodide (0.055 g, 0.33 mmol) were added at room temperature followed by addition of N-methylaniline (0.42 g, 4.01 mmol), The reaction mixture was stirred for 16 h at room temperature. After completion the reaction mixture was quenched cautiously by addition of water and the aqueous layer was extracted with ethyl acetate (3×100 mL). The combined organic layers were washed with water (2×100 mL) and brine solution (1×100 mL). The organic layer was separated, dried over anhydrous sodium sulphate, filtered and evaporated get the a crude product this was purified by column chromatography to get the desired N-(2,5-dimethyl-4-(N-methyl-N-phenylglycyl)phenyl)acetamide (0.5 g, 1.61 mmol, 48% yield).

Step D: Preparation of 1-(4-amino-2,5-dimethylphenyl)-2-(methyl(phenyl)amino)ethan-1-one To a stirred solution of N-(2,5-dimethyl-4-(N-methyl-N-phenylglycyl)phenyl)acetamide (0.4 g, 1.28 mmol) in ethanol (4 ml) and water (4.00 ml), potassium hydroxide (1.44 g, 25.8 mmol) was added at room temperature. The reaction mixture was stirred for 2 h at 85° C. After completion of the reaction, the reaction mixture was diluted with water and extracted with dichloromethane (3×50 mL). The combined organic layers were washed with water (2×100 mL) and brine solution (1×100 mL). The organic layer was separated, dried over anhydrous sodium sulphate, filtered and evaporated at reduced pressure to get the desired 1-(4-amino-2,5-dimethylphenyl)-2-phenoxyethan-1-one (0.3 g, 1.11 mmol, 47% yield).

Step E: Preparation of N'-(2,5-dimethyl-4-(N-methyl-N-phenylglycyl)phenyl)-N-ethyl-N-methylformimidamide To a stirred solution of 1-(4-amino-2,5-dimethylphenyl)-2-(methyl(phenyl)amino)ethan-1-one (0.25 g, 0.932 mmol) in trimethylorthoformate (5 ml) p-toluenesulfonic acid monohydrate (8.86 mg, 0.048 mmol) was added, and the resulting mixture was stirred at 105° C. for 2 h. After the complete conversion of the aniline derivative, the volatiles were evaporated to give the intermediate. This intermediate was dissolved in 1,4 dioxane (5 ml), N-ethylmethylamine (0.55 g, 9.32 mmol) was added and the mixture was stirred for 2 h at 105° C. After completion of the reaction, the reaction mixture was evaporated to give the crude compound, which was purified by preparative HPLC to get the desired N'-(2,5-dimethyl-4-(N-methyl-N-phenylglycyl)phenyl)-N-ethyl-N-methylformimidamide (150 mg, 0.444 mmol, 48% yield)

The following table-1 illustrates in a non-limiting manner examples of compounds according to the invention which can analogously synthesised according to the synthesis described for the example 1-14 or the procedure mentioned for general scheme.

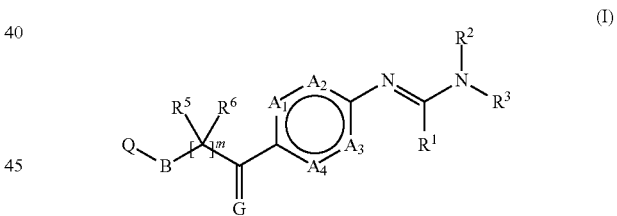

(I)

TABLE 1

| Compd. No. | Compound Name | Analytical Data |
|---|---|---|
| 1 | N'-(2,5-dimethyl-4-(2-(phenylthio)acetyl)phenyl)-N-ethyl-N-methylformimidamide | $^1$H-NMR(400 MHz, DMSO-D6) δ 7.79 (d, 2H), 7.34-7.29 (m, 4H), 7.22-7.18 (m, 1H), 6.69 (d, 1H), 4.51 (s, 2H), 3.30-3.47 (m, 2H), 3.06-2.92 (s, 3H), 2.30 (s, 3H), 2.18 (s, 3H), 1.14 (t, 3H); (M + 1): 341.2 |
| 2 | N'-(2,5-dimethyl-4-(2-phenoxyacetyl)phenyl)-N-ethyl-N-methylformimidamide | $^1$H-NMR(400 MHz, DMSO-D6) δ 7.79-7.68 (m, 2H), 7.29-7.23 (m, 2H), 6.97-6.93 (m, 3H), 6.71 (d, 1H), 5.33 (s, 2H), 3.52-3.33 (m, 2H), 2.88 (s, 3H), 2.38 (s, 3H), 2.20 (s, 3H), 1.14 (t, 3H); (M + 1): 325.25 |
| 3 | N'-(4-(2-(3-bromophenoxy)acetyl)-2,5-dimethylphenyl)-N-ethyl-N-methylformimidamide | $^1$H-NMR(400 MHz, DMSO-D6) δ 7.81-7.69 (m, 2H), 7.23 (t, 1H), 7.16-7.11 (m, 2H), 6.93-6.90 (m, 1H), 6.74 (s, 1H), 5.43 (s, 2H), 3.55-3.34 (m, 2H), 2.84 (s, 3H), 2.39 (s, 3H), 2.21 (s, 3H), 1.13-1.10 (m, 3H); (M + 1): 404.90 |
| 4 | N-ethyl-N'-(4-(2-((3-fluorophenyl)thio)acetyl)-2,5-dimethylphenyl)-N-methylformimidamide | $^1$H-NMR(400 MHz, DMSO-D6) δ 7.78 (s, 1H), 7.67 (s, 1H), 7.34-7.28 (m, 1H), 7.22-7.18 (m, 1H), 7.14 (d, 1H), 7.00-6.96 (m, 1H), 6.69 (d, 1H), 4.62 (s, 2H), 3.51-3.33 (m, 2H), 3.06-2.89 (s, 3H), 2.32 (s, 3H), 2.19 (s, 3H), 1.13 (t, 3H); (M + 1): 359.35 |

TABLE 1-continued

| | | |
|---|---|---|
| 5 | N'-(2,5-dimethyl-4-(2-(m-tolylthio)acetyl)phenyl)-N-ethyl-N-methylformimidamide | ¹H-NMR(400 MHz, DMSO-D6) δ 7.78 (s, 1H), 7.68 (d, 1H), 7.10-7.19 (m, 3H), 6.98 (d, 1H), 6.74-6.61 (1H), 4.46 (s, 2H), 3.51-3.34 (m, 2H), 2.88 (s, 3H), 2.30 (s, 3H), 2.24 (s, 3H), 2.17 (s, 3H), 1.13 (t, 3H); (M + 1): 355.35 |
| 6 | N'-(4-(2-((3-bromophenyl)thio)acetyl)-2,5-dimethylphenyl)-N-ethyl-N-methylformimidamide | ¹H-NMR(400 MHz, DMSO-D6) δ 7.77 (s, 1H), 7.67 (s, 1H), 7.50 (t, 1H), 7.36-7.31 (m, 2H), 7.23 (t, 1H), 6.74-6.61 (1H), 4.61 (s, 2H), 3.51-3.33 (m, 2H), 2.85 (s, 3H), 2.31 (s, 3H), 2.18 (s, 3H), 1.13 (t, 3H); (M + 1): 420.95 |
| 7 | N-ethyl-N'-(4-(2-((4-methoxyphenyl)thio)acetyl)-2,5-dimethylphenyl)-N-methylformimidamide | ¹H-NMR(400 MHz, DMSO-D6) δ 7.82-7.63 (1H), 7.59 (s, 1H), 7.31-7.27 (m, 2H), 6.89-6.85 (m, 2H), 6.67 (s, 1H), 4.30 (s, 2H), 3.72 (s, 3H), 3.50-3.33 (m, 2H), 2.89 (s, 3H), 2.29 (s, 3H), 2.14 (s, 3H), 1.13 (t, 3H); (M + 1): 371.41 |
| 8 | N'-(4-(2-((3,4-dichlorophenyl)thio)acetyl)-2,5-dimethylphenyl)-N-ethyl-N-methylformimidamide | ¹H-NMR(400 MHz, DMSO-D6) δ 7.87 (s, 1H), 7.77 (s, 1H), 7.69 (d, 1H), 7.62 (d, 1H), 7.41 (dd, 1H), 6.84-6.74 (1H), 4.76 (s, 2H), 3.61-3.42 (m, 2H), 3.01 (s, 3H), 2.42 (s, 3H), 2.28 (s, 3H), 1.24 (t, 3H); (M + 1): 400.9 |
| 9 | N-ethyl-N'-(4-(2-(3-fluorophenoxy)acetyl)-2,5-dimethylphenyl)-N-methylformimidamide | ¹H-NMR(400 MHz, DMSO-D6) δ 7.68-7.80 (m, 2H), 7.28 (td, 1H), 6.71-6.83 (m, 4H), 5.40 (s, 2H), 3.53-3.34 (m, 2H), 2.91 (s, 3H), 2.38 (s, 3H), 2.20 (s, 3H), 1.14 (t, 3H); (M + 1): 343.35 |
| 10 | N-ethyl-N'-(4-(2-(4-methoxyphenoxy)acetyl)-2,5-dimethylphenyl)-N-methylformimidamide | ¹H-NMR(400 MHz, DMSO-D6) δ 7.79-7.67 (m, 2H), 6.86-6.80 (m, 4H), 6.71 (d, 1H), 5.24 (s, 2H), 3.69 (s, 3H), 3.50-3.34 (m, 2H), 2.89 (s, 3H), 2.37 (s, 3H), 2.19 (s, 3H), 1.14 (t, 3H); (M + 1): 355.35 |
| 11 | N'-(4-(2-((3,4-dimethylphenyl)thio)acetyl)-2,5-dimethylphenyl)-N-ethyl-N-methylformimidamide | ¹H-NMR(400 MHz, DMSO-D6) δ 7.71 (br, 2H), 7.10 (s, 1H), 7.05 (s, 2H), 6.68 (s, 1H), 4.37 (s, 2H), 3.51-3.33 (m, 2H), 3.06-2.88 (3H), 2.30 (s, 3H), 2.16 (s, 9H), 1.13 (t, 3H); (M + 1): 369.20 |
| 12 | N'-(2,5-dimethyl-4-(2-(m-tolyloxy)acetyl)phenyl)-N-ethyl-N-methylformimidamide | ¹H-NMR(400 MHz, DMSO-D6) δ 7.79-7.67 (m, 2H), 7.14-7.10 (m, 1H), 6.74-6.67 (m, 4H), 5.30 (s, 2H), 3.51-3.33 (m, 2H), 2.90 (s, 3H), 2.38 (s, 3H), 2.25 (s, 3H), 2.20 (s, 3H), 1.14 (t, 3H); (M + 1): 339.35 |
| 13 | N'-(4-(2-(3-chlorophenoxy)acetyl)-2,5-dimethylphenyl)-N-ethyl-N-methylformimidamide | ¹H-NMR(400 MHz, DMSO-D6) δ 7.80-7.68 (m, 2H), 7.28 (t, 1H), 7.02-6.96 (m, 2H), 6.90 (ddd, 1H), 6.72 (d, 1H), 5.42 (s, 2H), 3.52-3.34 (m, 2H), 2.94 (s, 3H), 2.38 (s, 3H), 2.20 (s, 3H), 1.14 (t, 3H); (M + 1): 359.35 |
| 14 | N'-(2,5-dimethyl-4-(2-(4-(trifluoromethoxy)phenoxy)acetyl)phenyl)-N-ethyl-N-methylformimidamide | ¹H-NMR(400 MHz, DMSO-D6) δ 7.80-7.68 (m, 2H), 7.26 (dd, 2H), 6.98-6.94(m, 2H), 6.72 (d, 1H), 5.41 (s, 2H), 3.52-3.33 (m, 2H), 2.91 (s, 3H), 2.38 (s, 3H), 2.20 (s, 3H), 1.14 (t, 3H); (M + 1): 409.2 |
| 15 | N'-(2,5-dimethyl-4-(2-(p-tolyloxy)acetyl)phenyl)-N-ethyl-N-methylformimidamide | ¹H-NMR(400 MHz, DMSO-D6) δ 7.79-7.67 (m, 2H), 7.03-7.00 (m, 2H), 6.77-6.81 (m, 2H), 6.71 (d, 1H), 5.27 (s, 2H), 3.52-3.33 (m, 2H), 2.89 (s, 3H), 2.37 (s, 3H), 2.21 (s, 3H), 2.19 (s, 3H), 1.16-1.12 (m, 3H); (M + 1): 339.65 |
| 16 | N'-(4-(2-(4-chlorophenoxy)acetyl)-2,5-dimethylphenyl)-N-ethyl-N-methylformimidamide | ¹H-NMR(400 MHz, DMSO-D6) δ 7.80-7.68 (m, 2H), 7.28-7.24 (m, 2H), 6.96-6.91 (m, 2H), 6.72 (d, 1H), 5.38 (s, 2H), 3.52-3.33 (m, 2H), 2.90 (s, 3H), 2.38 (s, 3H), 2.20 (s, 3H), 1.14 (t, 3H); (M + 1): 359.30 |
| 17 | N'-(2,5-dimethyl-4-(2-(3-(methylthio)phenoxy)acetyl)phenyl)-N-ethyl-N-methylformimidamide | ¹H-NMR(400 MHz, DMSO-D6) δ 7.80-7.68 (m, 2H), 7.19 (t, 1H), 6.82-6.77 (m, 1H), 6.73-6.70 (m, 2H), 5.35 (s, 2H), 3.53-3.34 (m, 2H), 2.89 (s, 3H), 2.43 (s, 3H), 2.38 (s, 3H), 2.20 (s, 3H), 1.16-1.12 (m, 3H); (M + 1): 370 |
| 18 | N'-(4-(2-((3-chloro-5-(trifluoromethyl)pyridin-2-yl)thio)acetyl)-2,5-dimethylphenyl)-N-ethyl-N-methylformimidamide | ¹H-NMR(400 MHz, DMSO-D6) δ 8.69 (q, 1H), 8.35 (d, 1H), 7.85-7.62 (2H), 6.77-6.65 (bs, 1H), 4.79 (s, 2H), 3.50-3.29 (m, 2H), 2.90 (s, 3H), 2.33 (s, 3H), 2.21 (s, 3H), 1.14 (t, 3H); (M + 1): 444.15 |
| 19 | N'-(2-chloro-5-methyl-4-(2-phenoxyacetyl)phenyl)-N-ethyl-N-methylformimidamide | ¹H-NMR(400 MHz, DMSO-D6) δ 7.96 (s, 2H), 7.24-7.20 (m, 2H), 6.90-6.85 (m, 4H), 5.35 (s, 2H), 3.51-3.33 (m, 2H), 2.91 (s, 3H), 2.38 (s, 3H), 1.17-1.12 (m, 3H); (M + 1): 345.10 |
| 20 | N'-(2-chloro-4-(2-(3-chlorophenoxy)acetyl)-5-methylphenyl)-N-ethyl-N-methylformimidamide | ¹H-NMR(400 MHz, DMSO-D6) δ 7.98-7.79 (m, 2H), 7.28 (t, 1H), 7.05 (t, 1H), 6.99-6.90 (m, 3H), 5.45 (s, 2H), 3.53-3.37 (m, 2H), 2.93 (s, 3H), 2.38 (s, 3H), 1.18-1.12 (m, 3H); (M + 1): 379.05 |
| 21 | N'-(2-chloro-4-(2-(4-chlorophenoxy)acetyl)-5-methylphenyl)-N-ethyl-N-methylformimidamide | ¹H-NMR(400 MHz, DMSO-D6) δ 7.98-7.79 (m, 2H), 7.30 (d,, 2H), 6.97-6.92 (m, 3H), 5.40 (s, 2H), 3.52-3.39 (m, 2H), 2.94 (s, 3H), 2.37 (s, 3H), 1.15 (t, 3H); (M + 1): 379.10 |
| 22 | N'-(4-(2-((4-bromophenyl)thio)acetyl)-2,5-dimethylphenyl)-N-ethyl-N-methylformimidamide | ¹H-NMR(400 MHz, DMSO-D6) δ 7.78-7.67 (m, 2H), 7.47 (d, 2H), 7.27 (d, 2H), 6.69 (bs, 1H), 4.55 (s, 2H), 3.49-3.37 (m, 2H), 2.88 (s, 3H), 2.30 (s, 3H), 2.17 (s, 3H), 1.12-1.15 (m, 3H); (M + 1): 420.95 |
| 23 | N'-(4-(2-(3-bromophenoxy)acetyl)-2-chloro-5-methylphenyl)-N-ethyl-N-methylformimidamide | ¹H-NMR(400 MHz, DMSO-D6) δ 7.98 (s, 1H), 7.85 (d, 1H), 7.22 (t, 1H), 7.18 (t, 1H), 7.12-7.09 (m, 1H), 6.93-6.90 (m, 2H), 5.45 (s, 2H), 3.53-3.34 (m, 2H), 2.90 (s, 3H), 2.38 (s, 3H), 1.18-1.12 (m, 3H); (M + 1): 424.3 |
| 24 | N'-(2-chloro-4-(2-(3-fluorophenoxy)acetyl)-5-methylphenyl)-N-ethyl-N-methylformimidamide | ¹H-NMR(400 MHz, DMSO-D6) δ 7.98-7.79 (m, 2H), 7.33-7.24 (m, 1H), 6.99-6.91 (m, 1H), 6.89-6.82 (m, 1H), 6.81-6.70 (m, 2H), 5.42 (s, 2H), 3.53-3.36 (m, 2H), 2.93 (s, 3H), 2.38 (s, 3H), 1.18-1.12 (m, 3H); (M + 1): 363.10 |

TABLE 1-continued

| | | |
|---|---|---|
| 25 | N'-(2-chloro-5-methyl-4-(2-(p-tolyloxy)acetyl)phenyl)-N-ethyl-N-methylformimidamide | ¹H-NMR(400 MHz, DMSO-D6) δ 7.95-7.78 (m, 2H), 7.05 (d, 2H), 6.93 (d, 1H), 6.79-6.75 (m, 2H), 5.29 (s, 2H), 3.53-3.36 (m, 2H), 2.93 (s, 3H), 2.37 (s, 3H), 2.21 (s, 3H), 1.17-1.12 (m, 3H); (M + 1): 359.10 |
| 26 | N'-(2-chloro-5-methyl-4-(2-(m-tolyloxy)acetyl)phenyl)-N-ethyl-N-methylformimidamide | ¹H-NMR(400 MHz, DMSO-D6) δ 7.95-7.78 (m, 2H), 7.12 (t, 1H), 6.93 (d, 1H), 6.69-6.65 (m, 3H), 5.32 (s, 2H), 3.52-3.35 (m, 2H), 2.93 (s, 3H), 2.38 (s, 3H), 2.25 (s, 3H), 1.18-1.12 (m, 3H); (M + 1): 359.10 |
| 27 | N-ethyl-N'-(4-(2-((3-methoxyphenyl)thio)acetyl)-2,5-dimethylphenyl)-N-methylformimidamide | ¹H-NMR(400 MHz, DMSO-D6) δ 7.78-7.66 (m, 2H), 7.24-7.20 (m, 1H), 6.86-6.85 (m, 2H), 6.74-6.66 (m, 2H), 4.50 (s, 2H), 3.71 (s, 3H), 3.52-3.33 (m, 2H), 2.85 (s, 3H), 2.30 (s, 3H), 2.17 (s, 3H), 1.13 (t, 3H); (M + 1): 371.35 |
| 28 | N-ethyl-N'-(4-(2-((4-fluorophenyl)thio)acetyl)-2,5-dimethylphenyl)-N-methylformimidamide | ¹H-NMR(400 MHz, DMSO-D6) δ 7.73 (d, 2H), 7.44-7.40 (m, 2H), 7.17-7.12 (m, 2H), 6.68 (bs, 1H), 4.47 (s, 2H), 3.51-3.32 (m, 2H), 2.88 (s, 3H), 2.29 (s, 3H), 2.16 (s, 3H), 1.13 (t, 3H); (M + 1): 359.35 |
| 29 | N'-(4-(2-((4-chlorophenyl)thio)acetyl)-2,5-dimethylphenyl)-N-ethyl-N-methylformimidamide | ¹H-NMR(400 MHz, DMSO-D6) δ 7.78-7.67 (m, 2H), 7.34 (s, 4H), 6.68 (d, 1H), 4.55 (s, 2H), 3.51-3.32 (m, 2H), 2.89 (s, 3H), 2.30 (s, 3H), 2.17 (s, 3H), 1.13 (t, 3H); (M + 1): 375.3 |
| 30 | N'-(4-(2-((2-bromophenyl)thio)acetyl)-2,5-dimethylphenyl)-N-ethyl-N-methylformimidamide | ¹H-NMR(400 MHz, DMSO-D6) δ 7.82-7.68 (m, 2H), 7.59 (d, 1H), 7.33 (d, 2H), 7.14-7.10 (m, 1H), 6.70 (d, 1H), 4.64 (s, 2H), 3.51-3.35 (m, 2H), 2.87 (s, 3H), 2.36 (d, 3H), 2.20 (s, 3H), 1.14 (t, 3H); (M + 1): 420.95 |
| 31 | N'-(4-(2-(2-bromophenoxy)acetyl)-2-chloro-5-methylphenyl)-N-ethyl-N-methylformimidamide | ¹H-NMR(400 MHz, DMSO-D6) δ 7.99-7.78 (m, 2H), 7.56 (dd, 1H), 7.24-7.20 (m, 1H), 6.99-6.92 (m, 2H), 6.86 (td, 1H), 5.50 (s, 2H), 3.55-3.44 (m, 2H), 2.93 (s, 3H), 2.37 (s, 3H), 1.17-1.12 (m, 3H); (M + 1): 424.95 |
| 32 | N-ethyl-N'-(4-(2-(2-fluorophenoxy)acetyl)-2,5-dimethylphenyl)-N-methylformimidamide | ¹H-NMR(400 MHz, DMSO-D6) δ 7.74 (t, 2H), 7.17-7.10 (m, 1H), 7.08-7.01 (m, 2H), 6.94-6.88 (m, 1H), 6.72 (d, 1H), 5.46 (s, 2H), 3.51-3.33 (m, 2H), 2.87 (s, 3H), 2.38 (s, 3H), 2.20 (s, 3H), 1.14 (t, 3H); (M + 1): 343.25 |
| 33 | N-ethyl-N'-(4-(2-(4-fluorophenoxy)acetyl)-2,5-dimethylphenyl)-N-methylformimidamide | ¹H-NMR(400 MHz, DMSO-D6) δ 7.79-7.67 (m, 2H), 7.07-7.12 (m, 2H), 6.95-6.91 (m, 2H), 6.71 (d, 1H), 5.33 (s, 2H), 3.53-3.34 (m, 2H), 2.89(s, 3H), 2.38 (s, 3H), 2.20 (s, 3H), 1.14 (t, 3H); (M + 1): 343.25 |
| 34 | N'-(4-(2-(2-bromophenoxy)acetyl)-2,5-dimethylphenyl)-N-ethyl-N-methylformimidamide | ¹H-NMR(400 MHz, DMSO-D6) δ 7.80-7.68 (m, 2H), 7.57 (dd, 1H), 7.24-7.20 (m, 1H), 6.92-6.90 (m, 1H), 6.84-6.80 (m, 1H), 6.72 (d, 1H), 5.49 (s, 2H), 3.53-3.34 (m, 2H), 2.89 (s, 3H), 2.38 (s, 3H), 2.20 (s, 3H), 1.14 (t, 3H); (M + 1): 404.5 |
| 35 | N'-(2-chloro-5-methyl-4-(2-(m-tolylthio)acetyl)phenyl)-N-ethyl-N-methylformimidamide | ¹H-NMR(400 MHz, DMSO-D6) δ 7.94 (s, 1H), 7.86-7.77 (1H), 7.18-7.09 (m, 3H), 6.99 (d, 1H), 6.89 (d, 1H), 4.50 (s, 2H), 3.54-3.34 (m, 2H), 2.89 (s, 3H), 2.27 (s, 3H), 2.24 (s, 3H), 1.11-1.18 (m, 3H); (M + 1): 375.15 |
| 36 | N'-(4-(2-((3-bromophenyl)thio)acetyl)-2-chloro-5-methylphenyl)-N-ethyl-N-methylformimidamide | ¹H-NMR(400 MHz, DMSO-D6) δ 8.00 (s, 1H), 7.92-7.76 (1H), 7.50 (t, 1H), 7.36-7.30 (m, 2H), 7.23 (t, 1H), 6.90 (d, 1H), 4.65 (s, 2H), 3.54-3.34 (m, 2H), 2.91 (s, 3H), 2.29 (s, 3H), 1.18-1.13 (m, 3H); (M + 1): 440.95 |
| 37 | N'-(2-chloro-4-(2-((3-fluorophenyl)thio)acetyl)-5-methylphenyl)-N-ethyl-N-methylformimidamide | ¹H-NMR(400 MHz, DMSO-D6) δ 8.01 (s, 1H), 7.90-7.78 (m, 1H), 7.34-7.28 (m, 1H), 7.21 (dt, 1H), 7.12-7.15 (m, 1H), 7.01-6.96 (m, 1H), 6.90 (d, 1H), 4.66 (s, 2H), 3.53-3.34 (m, 2H), 2.91 (s, 3H), 2.29 (s, 3H), 1.17-1.13 (m, 3H); (M + 1): 379.10 |
| 38 | N'-(2-chloro-4-(2-((4-chlorophenyl)thio)acetyl)-5-methylphenyl)-N-ethyl-N-methylformimidamide | ¹H-NMR(400 MHz, DMSO-D6) δ 7.97 (s, 1H), 7.92-7.73 (1H), 7.34 (s, 4H), 6.90 (d, 1H), 4.59 (s, 2H), 3.52-3.34 (m, 2H), 2.90 (m, 3H), 2.28 (s, 3H), 1.17-1.11 (m, 3H); (M + 1): 395.5 |
| 39 | N'-(4-(2-((2-bromophenyl)thio)acetyl)-2-chloro-5-methylphenyl)-N-ethyl-N-methylformimidamide | ¹H-NMR(400 MHz, DMSO-D6) δ 8.06 (s, 1H), 7.93-7.76 (1H), 7.58 (d, 1H), 7.33 (d, 2H), 7.06-7.11 (m, 1H), 6.92 (d, 1H), 4.68 (s, 2H), 3.53-3.35 (m, 2H), 2.91 (s, 3H), 2.32 (s, 3H), 1.18-1.12 (m, 3H); (M + 1): 440.1 |
| 40 | 2-(3-chlorophenoxy)-1-(2,5-dimethyl-4-((morpholinomethylene)amino)phenyl)ethan-1-one | ¹H-NMR(400 MHz, DMSO-D6) δ 7.80 (s, 1H), 7.75 (s, 1H), 7.28 (t, 1H), 7.02 (t, 1H), 7.00-6.94 (m, 1H), 6.94-6.85 (m, 1H), 6.76 (s, 1H), 5.43 (s, 2H), 3.68-3.38 (8H), 2.38 (s, 3H), 2.20 (s, 3H); (M + 1): 387.10 |
| 41 | 2-(3-chlorophenoxy)-1-(2,5-dimethyl-4-((piperidin-1-ylmethylene)amino)phenyl)ethan-1-one | ¹H-NMR(400 MHz, DMSO-D6) δ 7.74 (s, 2H), 7.28 (t, 1H), 7.01 (t, 1H), 7.00-6.94 (m, 1H), 6.93-6.85 (m, 1H), 6.73 (s, 1H), 5.42 (s, 2H), 3.66-3.33 (4H), 2.38 (s, 3H), 2.19 (s, 3H), 1.60-1.63 (m, 2H), 1.53 (s, 4H); (M + 1): 385.15 |
| 42 | N'-(4-(2-(3-chlorophenoxy)acetyl)-2,5-dimethylphenyl)-N-isopropyl-N-methylformimidamide | ¹H-NMR(400 MHz, DMSO-D6) δ 7.85-7.67 (m, 2H), 7.28 (t, 1H), 7.01 (t, 1H), 7.00-6.94 (m, 1H), 6.93-6.86 (m, 1H), 6.72 (d, 1H), 5.42 (s, 2H), 3.88-3.81 (m, 1H), 2.79 (s, 3H), 2.38 (s, 3H), 2.21 (s, 3H), 1.25-1.19 (m, 6H); (M + 1): 373.15 |
| 43 | N-allyl-N'-(4-(2-(3-chlorophenoxy)acetyl)-2,5-dimethylphenyl)-N-methylformimidamide | ¹H-NMR(400 MHz, DMSO-D6) δ 7.78 (t, 2H), 7.28 (t, 1H), 7.02 (t, 1H), 7.00-6.94 (m, 1H), 6.94-6.86 (m, 1H), 6.73 (s, 1H), 5.86 (q, 1H), 5.42 (s, 2H), 5.20-5.25 (m, 2H), 4.07-3.95 (m, 2H), 3.04-2.85 (3H), 2.38 (s, 3H), 2.21 (s, 3H); (M + 1): 371.15 |

TABLE 1-continued

| | | |
|---|---|---|
| 44 | N'-(2-chloro-4-(2-(2-fluorophenoxy)acetyl)-5-methylphenyl)-N-ethyl-N-methylformimidamide | ¹H-NMR(400 MHz, DMSO-D6) δ 7.97-7.79 (m, 2H), 7.23-7.17 (m, 1H), 7.10-7.03 (m, 2H), 6.96-6.89 (m, 2H), 5.49 (s, 2H), 3.53-3.34 (m, 2H), 2.90 (s, 3H), 2.38 (s, 3H), 1.18-1.12 (m, 3H); (M + 1): 363.10 |
| 45 | N'-(2-chloro-4-(2-(4-fluorophenoxy)acetyl)-5-methylphenyl)-N-ethyl-N-methylformimidamide | ¹H-NMR(400 MHz, DMSO-D6) δ 7.96-7.78 (m, 2H), 7.11-7.07 (m, 2H), 6.96-6.92 (m, 3H), 5.36 (s, 2H), 3.43-3.37 (m, 2H), 2.92 (s, 3H), 2.37 (s, 3H), 1.12-1.17 (m, 3H); (M + 1): 363.10 |
| 46 | N'-(4-(2-(3-chlorophenoxy)acetyl)-2,5-dimethylphenyl)-N-cyanoformimidamide | — |
| 47 | N'-(4-(2-((3,4-dimethylphenyl)thio)acetyl)-2,5-dimethylphenyl)-N-isopropyl-N-methylformimidamide | ¹H-NMR(400 MHz, DMSO-D6) δ 7.90-7.60 (2H), 7.10 (s, 1H), 7.05 (d, 2H), 6.68 (s, 1H), 4.37 (s, 2H), 3.86-3.80 (m, 1H), 2.86 (s, 3H), 2.30 (s, 3H), 2.17 (s, 9H), 1.22 (d, 6H); (M + 1): 383.50 |
| 48 | N-allyl-N'-(4-(2-((3,4-dimethylphenyl)thio)acetyl)-2,5-dimethylphenyl)-N-methylformimidamide | ¹H-NMR(400 MHz, DMSO-D6) δ 7.77 (d, 1H), 7.64 (s, 1H), 7.10 (s, 1H), 7.04 (d, 2H), 6.68 (s, 1H), 5.86 (s, 1H), 5.24-5.19 (m, 2H), 4.37 (s, 2H), 4.06-3.94 (m, 2H), 3.04-2.84 (3H), 2.30 (s, 3H), 2.15 (s, 9H); (M + 1): 381.4 |
| 49 | 1-(2,5-dimethyl-4-((morpholinomethylene)amino)phenyl)-2-((3,4-dimethylphenyl)thio)ethan-1-one | ¹H-NMR(400 MHz, DMSO-D6) δ 7.75 (s, 1H), 7.62 (s, 1H), 7.08 (s, 1H), 7.02 (d, 2H), 6.68 (s, 1H), 4.35 (s, 2H), 3.63-3.34 (8H), 2.27 (s, 3H), 2.14-2.11 (9H); (M + 1): 397.3 |
| 50 | N'-(2-chloro-4-(2-((3,4-dichlorophenyl)thio)acetyl)-5-methylphenyl)-N-ethyl-N-methylformimidamide | ¹H-NMR(400 MHz, DMSO-D6) δ 8.01 (s, 1H), 7.95-7.73 (1H), 7.60 (d, 1H), 7.53 (d, 1H), 7.31 (dd, 1H), 6.91 (d, 1H), 4.70 (s, 2H), 3.55-3.34 (m, 2H), 2.90 (s, 3H), 2.30 (s, 3H), 1.17-1.11 (m, 3H); (M + 1): 430.90 |
| 51 | N'-(2-chloro-4-(2-((3,5-dichlorophenyl)thio)acetyl)-5-methylphenyl)-N-ethyl-N-methylformimidamide | ¹H-NMR(400 MHz, DMSO-D6) δ 8.04 (s, 1H), 7.94-7.74 (1H), 7.39-7.37 (m, 3H), 6.91 (d, 1H), 4.77 (s, 2H), 3.56-3.34 (m, 2H), 2.91 (s, 3H), 2.31 (s, 3H), 1.17-1.12 (m, 3H); (M + 1): 430.8 |
| 52 | N'-(2-chloro-5-methyl-4-(2-(3-(methylthio)phenoxy)acetyl)phenyl)-N-ethyl-N-methylformimidamide | ¹H-NMR(400 MHz, DMSO-D6) δ 7.97-7.79 (m, 2H), 7.19 (t, 1H), 6.94 (d, 1H), 6.81-6.79 (m, 2H), 6.71-6.68 (m, 1H), 5.39 (s, 2H), 3.53-3.35 (m, 2H), 2.94 (s, 3H), 2.43 (s, 3H), 2.37 (s, 3H), 1.17-1.11 (m, 3H); (M + 1): 391.10 |
| 53 | N'-(2-chloro-5-methyl-4-(2-(4-(trifluoromethoxy)phenoxy)acetyl)phenyl)-N-ethyl-N-methylformimidamide | ¹H-NMR(400 MHz, DMSO-D6) δ 7.98-7.79 (m, 2H), 7.27 (d, 2H), 7.05-7.00 (m, 2H), 6.95 (d, 1H), 5.45 (s, 2H), 3.53-3.35 (m, 2H), 2.91 (s, 3H), 2.38 (s, 3H), 1.18-1.12 (m, 3H); (M + 1): 429.15 |
| 54 | N'-(2-chloro-4-(2-((4-fluorophenyl)thio)acetyl)-5-methylphenyl)-N-ethyl-N-methylformimidamide | ¹H-NMR(400 MHz, DMSO-D6) δ 7.93 (s, 1H), 7.91-7.74 (1H), 7.39-7.36 (m, 2H), 7.17-7.12 (m, 2H), 6.89 (d, 1H), 4.51 (s, 2H), 3.52-3.35 (m, 2H), 2.92 (s, 3H), 2.26 (s, 3H), 1.17-1.12 (m, 3H); (M + 1): 379.15 |
| 55 | N'-(4-(2-((4-bromophenyl)thio)acetyl)-2-chloro-5-methylphenyl)-N-ethyl-N-methylformimidamide | ¹H-NMR(400 MHz, DMSO-D6) δ 7.96 (s, 1H), 7.93-7.72 (1H), 7.48-7.44 (m, 2H), 7.25-7.23 (m, 2H), 6.89 (d, 1H), 4.59 (s, 2H), 3.53-3.33 (m, 2H), 2.90 (s, 3H), 2.28 (s, 3H), 1.17-1.11 (m, 3H); (M + 1): 440.90 |
| 56 | N'-(2-chloro-4-(2-((3-methoxyphenyl)thio)acetyl)-5-methylphenyl)-N-ethyl-N-methylformimidamide | — |
| 57 | N'-(2-chloro-5-methyl-4-(2-(phenylthio)acetyl)phenyl)-N-ethyl-N-methylformimidamide | ¹H-NMR(400 MHz, DMSO-D6) δ 7.96 (s, 1H), 7.92-7.72 (1H), 7.26-7.33 (m, 4H), 7.15-7.19 (m, 1H), 6.89 (d, 1H), 4.54 (s, 2H), 3.54-3.34 (m, 2H), 2.92 (s, 3H), 2.26 (s, 3H), 1.17-1.11 (m, 3H); (M + 1): 361.15 |
| 58 | N'-(2-chloro-4-(2-((2-fluorophenyl)thio)acetyl)-5-methylphenyl)-N-ethyl-N-methylformimidamide | ¹H-NMR(400 MHz, DMSO-D6) δ 7.99 (s, 1H), 7.94-7.72 (1H), 7.39 (td, 1H), 7.27-7.12 (m, 3H), 6.90 (d, 1H), 4.56 (s, 2H), 3.53-3.35 (m, 2H), 2.91 (s, 3H), 2.27 (s, 3H), 1.17-1.11 (m, 3H); (M + 1): 379.10 |
| 59 | N-ethyl-N'-(4-(2-((2-fluorophenyl)thio)acetyl)-2,5-dimethylphenyl)-N-methylformimidamide | ¹H-NMR(400 MHz, DMSO-D6) δ 7.74 (d, 2H), 7.37 (td, 1H), 7.24-7.10 (m, 3H), 6.67 (s, 1H), 4.50 (s, 2H), 3.51-3.31 (m, 2H), 2.85 (s, 3H), 2.27 (s, 3H), 2.15 (s, 3H), 1.11 (t, 3H); (M + 1): 359.30 |
| 60 | N'-(2,5-dimethyl-4-(2-((3-(trifluoromethyl)phenyl)thio)acetyl)phenyl)-N-ethyl-N-methylformimidamide | ¹H-NMR(400 MHz, DMSO-D6) δ 7.78-7.66 (m, 2H), 7.62-7.60 (m, 2H), 7.53-7.50 (m, 2H), 6.67 (d, 1H), 4.64 (s, 2H), 3.52-3.31 (m, 2H), 2.83 (s, 3H), 2.26 (s, 3H), 2.16 (s, 3H), 1.11 (t, 3H); (M + 1): 409.15 |
| 61 | 2-(3-chlorophenoxy)-1-(2,5-dimethyl-4-((thiomorpholinomethylene)amino)phenyl)ethan-1-one | ¹H-NMR(400 MHz, DMSO-D6) δ 7.76 (d, 2H), 7.28 (t, 1H), 7.02-6.89 (m, 3H), 6.76 (s, 1H), 5.42 (s, 2H), 3.93-3.59 (4H), 2.64 (4H), 2.38 (s, 3H), 2.20 (s, 3H); (M + 1): 403.10 |
| 62 | 1-(2,5-dimethyl-4-((thiomorpholinomethylene)amino)phenyl)-2-((3,4-dimethylphenyl)thio)ethan-1-one | ¹H-NMR(400 MHz, DMSO-D6) δ 7.74 (s, 1H), 7.65 (s, 1H), 7.10 (s, 1H), 7.04 (d, 2H), 6.70 (s, 1H), 4.38 (s, 2H), 3.77 (t, 4H), 2.64 (t, 4H), 2.29 (s, 3H), 2.15 (s, 6H), 2.14 (s, 3H); (M + 1): 413.30 |
| 63 | N'-(4-(2-((3-chlorophenyl)thio)acetyl)-2,5-dimethylphenyl)-N-ethyl-N-methylformimidamide | ¹H-NMR(400 MHz, DMSO-D6) δ 7.78 (d, 2H), 7.38 (t, 1H), 7.32-7.26 (m, 2H), 7.21 (dt, 1H), 6.69 (d, 1H), 4.62 (s, 2H), 3.55-3.34 (m, 2H), 2.86 (s, 3H), 2.31 (s, 3H), 2.18 (s, 3H), 1.13 (t, 3H); (M + 1): 375.15 |

TABLE 1-continued

| | | |
|---|---|---|
| 64 | N'-(2,5-dimethyl-4-(2-((4-(methylthio)phenyl)thio)acetyl)phenyl)-N-ethyl-N-methylformimidamide | $^1$H-NMR(400 MHz, DMSO-D6) δ 7.66 (s, 2H), 7.27 (d, 2H), 7.18 (d, 2H), 6.68 (s, 1H), 4.44 (s, 2H), 3.52-3.34 (m, 2H), 2.87 (s, 3H), 2.44 (s, 3H), 2.30 (s, 3H), 2.16 (s, 3H), 1.13 (t, 3H); (M + 1): 387.10 |
| 65 | N'-(2-chloro-4-(2-((3-chlorophenyl)thio)acetyl)-5-methylphenyl)-N-ethyl-N-methylformimidamide | $^1$H-NMR(400 MHz, DMSO-D6) δ 8.00 (s, 1H), 7.93-7.74 (1H), 7.39 (t, 1H), 7.32-7.20 (m, 3H), 6.90 (d, 1H), 4.66 (s, 2H), 3.53-3.34 (m, 2H), 2.92 (s, 3H), 2.29 (s, 3H), 1.11-1.17 (m, 3H); (M + 1): 397.10 |
| 66 | N'-(2-chloro-5-methyl-4-(2-((3-(trifluoromethyl)phenyl)thio)acetyl)phenyl)-N-ethyl-N-methylformimidamide | $^1$H-NMR(400 MHz, DMSO-D6) δ 7.98 (s, 1H), 7.89-7.72 (1H), 7.59 (t, 2H), 7.47-7.45 (m, 2H), 6.87 (d, 1H), 4.69 (s, 2H), 3.49-3.30 (m, 2H), 2.91 (s, 3H), 1.14-1.09 (m, 3H); (M + 1): 429.10 |
| 67 | N'-(2,5-dimethyl-4-(2-(3-((perfluoroethyl)thio)phenoxy)acetyl)phenyl)-N-ethyl-N-methylformimidamide | $^1$H-NMR(400 MHz, DMSO-D6) δ 7.80-7.68 (m, 2H), 7.43 (t, 1H), 7.27-7.17 (m, 3H), 6.72 (d, 1H), 5.48 (s, 2H), 3.57-3.34 (m, 2H), 2.80 (s, 3H), 2.37 (s, 3H), 2.21 (s, 3H), 1.12-1.08 (m, 3H); (M + 1): 475.40 |
| 68 | N'-(2,5-dimethyl-4-(2-(3-((trifluoromethyl)thio)phenoxy)acetyl)phenyl)-N-ethyl-N-methylformimidamide | $^1$H-NMR(400 MHz, DMSO-D6) δ 7.81-7.69 (m, 2H), 7.45-7.41 (m, 1H), 7.27-7.23 (m, 2H), 7.16 (d, 1H), 6.74 (s, 1H), 5.47 (s, 2H), 3.52-3.34 (m, 2H), 2.89 (m, 3H), 2.37 (s, 3H), 2.21 (s, 3H), 1.14 (t, 3H); (M + 1): 425.35 |
| 69 | N'-(4-(2-(3-(dimethylamino)phenoxy)acetyl)-2,5-dimethylphenyl)-N-ethyl-N-methylformimidamide | $^1$H-NMR(400 MHz, DMSO-D6) δ 7.80-7.67 (m, 2H), 7.02 (t, 1H), 6.74 (s, 1H), 6.30 (d, 1H), 6.19 (d, 2H), 5.24 (s, 2H), 3.51-3.34 (m, 2H), 2.90 (s, 3H), 2.84 (s, 6H), 2.37 (s, 3H), 2.19 (s, 3H), 1.16-1.10 (m, 3H); (M + 1): 368.10 |
| 70 | N'-(2,5-dimethyl-4-(2-methyl-2-(m-tolyloxy)propanoyl)phenyl)-N-ethyl-N-methylformimidamide | $^1$H-NMR(400 MHz, DMSO-D6) δ 7.87 (s, 1H), 7.73 (s, 1H), 7.04 (t, 1H), 6.71-6.67 (m, 2H), 6.54 (s, 1H), 6.49 (dd, 1H), 3.47-3.32 (m, 2H), 2.85 (s, 3H), 2.35 (s, 3H), 2.17 (s, 3H), 2.08 (s, 3H), 1.58 (s, 6H), 1.10 (t; 3 H); (M + 1): 367.65 |
| 71 | N'-(2,5-dimethyl-4-(2-(o-tolyloxy)acetyl)phenyl)-N-ethyl-N-methylformimidamide | $^1$H-NMR(400 MHz, DMSO-D6) δ 7.73 (d, 1H), 7.63 (s, 1H), 7.02 (d, 2H), 6.92 (dd, 2H), 6.73 (s, 1H), 4.99 (s, 2H), 3.46-3.35 (m, 2H), 2.97 (s, 3H), 2.22 (s, 6H), 2.15 (s, 3H), 1.13 (t, 3H); (M + 1): 339.5 |
| 72 | N'-(2,5-dimethyl-4-(2-(3-(trifluoromethyl)phenoxy)acetyl)phenyl)-N-ethyl-N-methylformimidamide | $^1$H-NMR(400 MHz, DMSO-D6) δ 7.80-7.68 (m, 2H), 7.47-7.52 (m, 1H), 7.22-7.28 (m, 3H), 6.73 (d, 1H), 5.51 (s, 2H), 3.47-3.34 (m, 2H), 2.98 (s, 3H), 2.37 (s, 3H), 2.21 (s, 3H), 1.16-1.12 (m, 3H); (M + 1): 393.1 |
| 73 | N'-(4-(2-(3,4-dichlorophenoxy)acetyl)-2,5-dimethylphenyl)-N-ethyl-N-methylformimidamide | $^1$H-NMR(400 MHz, DMSO-D6) δ 7.80-7.68 (m, 2H), 7.50 (d, 1H), 7.25 (d, 1H), 6.96 (dd, 1H), 6.72 (d, 1H), 5.46 (s, 2H), 3.47-3.34 (m, 2H), 2.98 (s, 3H), 2.38 (s, 3H), 2.20 (s, 3H), 1.14 (t, 3H); (M + 1): 393.5 |
| 74 | N'-(4-(2-(2,6-dimethylphenoxy)acetyl)-2,5-dimethylphenyl)-N-ethyl-N-methylformimidamide | $^1$H-NMR(400 MHz, DMSO-D6) δ 7.73 (d, 1H), 7.63 (s, 1H), 7.02 (d, 2H), 6.92 (dd, 2H), 6.73 (s, 1H), 4.99 (s, 2H), 3.46-3.35 (m, 2H), 2.97 (, 3H), 2.44 (s, 3H), 2.22 (s, 6H), 2.15 (s, 3H), 1.13 (t, 3H); (M + 1): 353.20 |
| 75 | N'-(4-(2-(2-(tert-butyl)phenoxy)acetyl)-2,5-dimethylphenyl)-N-ethyl-N-methylformimidamide | $^1$H-NMR(400 MHz, DMSO-D6) δ 7.79-7.68 (m, 2H), 7.22 (dd, 1H), 7.14-7.10 (m, 1H), 6.88-6.83 (m, 2H), 6.71 (d, 1H), 5.33 (s, 2H), 3.46-3.35 (m, 2H), 2.97 (s, 3H), 2.40 (s, 3H), 2.19 (s, 3H), 1.36 (s, 9H), 1.14 (t, 3H); (M + 1): 381.20 |
| 76 | N'-(4-(2-(3,4-dimethylphenoxy)acetyl)-2,5-dimethylphenyl)-N-ethyl-N-methylformimidamide | $^1$H-NMR(400 MHz, DMSO-D6) δ 7.79-7.67 (m, 2H), 6.98 (d, 1H), 6.72-6.70 (m, 2H), 6.60 (dd, 1H), 5.25 (s, 2H), 3.46-3.35 (m, 2H), 2.97 (s, 3H), 2.38 (s, 3H), 2.19 (s, 3H), 2.15 (s, 3H), 2.11 (s, 3H), 1.16-1.12 (m, 3H); (M + 1): 353.20 |
| 77 | N'-(2,5-dimethyl-4-(2-(m-tolyloxy)propanoyl)phenyl)-N-ethyl-N-methylformimidamide | $^1$H-NMR(400 MHz, DMSO-D6) δ 7.80 (s, 2H), 7.09 (t, 1H), 6.72-6.68 (m, 3H), 6.61 (dd, 1H), 5.79 (q, 1H), 3.46-3.35 (m, 2H), 2.97 (s, 3H), 2.33 (s, 3H), 2.20 (s, 6H), 1.43 (d, 3H), 1.13 (t, 3H); (M + 1): 353.20 |
| 78 | N'-(2,5-dimethyl-4-(2-(3-((3,4,4-trifluorobut-3-en-1-yl)thio)phenoxy)acetyl)phenyl)-N-ethyl-N-methylformimidamide | $^1$H-NMR(400 MHz, DMSO-D6) δ 7.80-7.68 (m, 2H), 7.24-7.20 (m, 1H), 6.92-6.90 (m, 2H), 6.78-6.70 (m, 2H), 5.37 (s, 2H), 3.46-3.35 (m, 2H), 3.17 (t, 2H), 3.03 (s, 3H), 2.65-2.55 (m, 2H), 2.37 (s, 3H), 2.20 (s, 3H), 1.14 (t, 3H); (M + 1): 465.50 |
| 79 | N'-(2,5-dimethyl-4-(2-(4-((trifluoromethyl)thio)phenoxy)acetyl)phenyl)-N-ethyl-N-methylformimidamide | $^1$H-NMR(400 MHz, DMSO-D6) δ 7.79-7.67 (m, 2H), 7.07-7.12 (m, 2H), 6.95-6.91 (m, 2H), 6.71 (d, 1H), 5.33 (s, 2H), 3.53-3.34 (2H), 3.06-2.89 (3H), 2.38 (s, 3H), 2.20 (s, 3H), 1.14 (t, 3H); (M + 1): 425.25 |
| 80 | N'-(4-(2-(3-bromo-4-methylphenoxy)acetyl)-2,5-dimethylphenyl)-N-ethyl-N-methylformimidamide | $^1$H-NMR(400 MHz, DMSO-D6) δ 7.80-7.68 (m, 2H), 7.22 (d, 1H), 7.14 (d, 1H), 6.86 (dd, 1H), 6.72 (d, 1H), 5.37 (s, 2H), 3.47-3.35 (m, 2H), 2.98 (s, 3H), 2.37 (s, 3H), 2.25 (s, 6H), 1.15-1.07 (m, 3H); (M + 1): 418.95 |
| 81 | N'-(4-(2-(2-bromo-4-methylphenoxy)acetyl)-2,5-dimethylphenyl)-N-ethyl-N-methylformimidamide | $^1$H-NMR(400 MHz, DMSO-D6) δ 7.80-7.68 (m, 2H), 7.39 (d, 1H), 7.05 (d, 1H), 6.82 (d, 1H), 6.71 (d, 1H), 5.42 (s, 2H), 3.46-3.34 (m, 2H), 2.98 (s, 3H), 2.36 (s, 3H), 2.20 (s, 6H), 1.22-1.08 (m, 3H); (M + 1): 418.95 |
| 82 | N'-(4-(2-((2,6-dimethylphenyl)thio)acetyl)-2,5-dimethylphenyl)-N-ethyl-N-methylformimidamide | $^1$H-NMR(400 MHz, DMSO-D6) δ 7.71 (d, 1H), 7.51 (s, 1H), 7.15-7.07 (m, 3H), 6.64 (d, 1H), 4.03 (s, 2H), 3.46-3.35 (m, 2H), 2.97 (s, 3H), 2.31 (s, 6H), 2.20 (s, 3H), 2.10 (s, 3H), 1.15-1.12 (m, 3H); (M + 1): 369.45 |

TABLE 1-continued

| | | |
|---|---|---|
| 83 | N'-(2,5-dimethyl-4-(2-methyl-2-(m-tolylthio)propanoyl)phenyl)-N-ethyl-N-methylformimidamide | $^1$H-NMR(400 MHz, DMSO-D6) δ 7.77 (s, 1H), 7.67 (d, 1H), 7.25-7.19 (m, 4H), 6.66 (s, 1H), 3.35 (s, 2H), 2.95 (s, 3H), 2.26 (s, 3H), 2.17 (s, 3H), 2.09 (s, 3H), 1.38 (s, 6H), 1.13 (t, 3H); (M + 1): 383.35 |
| 84 | N'-(4-(N-(4-chlorophenyl)-N-methylglycyl)-2,5-dimethylphenyl)-N-ethyl-N-methylformimidamide | $^1$H-NMR(400 MHz, DMSO-D6) δ 7.78-7.66 (m, 2H), 7.14-7.10 (m, 2H), 6.69 (d, 1H), 6.63-6.58 (m, 2H), 4.81 (s, 2H), 3.46-3.35 (m, 2H), 2.95 (s, 6H), 2.35 (s, 3H), 2.21 (s, 3H), 1.14 (t, 3H); (M + 1): 372.9 |
| 85 | N'-(2,5-dimethyl-4-(N-methyl-N-phenylglycyl)phenyl)-N-ethyl-N-methylformimidamide | $^1$H-NMR(400 MHz, DMSO-D6) δ 7.86-7.56 (2H), 7.20-7.00 (2H), 6.79-6.44 (4H), 4.88(m, 2H), 3.41-3.23 (m, 2H), 3.13(s, 3H), 2.68-2.08 (s, 9H), 1.31-1.06 (t, 3H); (M + 1): 338.60 |
| 86 | N'-(4-(2-(2,6-dichlorophenoxy)acetyl)-2,5-dimethylphenyl)-N-ethyl-N-methylformimidamide | $^1$H-NMR(400 MHz, DMSO-D6) δ 7.90-7.41 (4H), 7.31-7.13 (1H), 6.84-6.66 (1H), 5.32 (s, 2H), 3.57-3.25 (m, 2H), 3.11 (s, 3H), 2.26 (s, 2H), 2.31 (s, 3H), 1.41-0.95 (m, 3H); (M + 1): 394.3 |
| 87 | N'-(4-(2-(2,6-dibromophenoxy)acetyl)-2,5-dimethylphenyl)-N-ethyl-N-methylformimidamide | $^1$H-NMR(400 MHz, DMSO-D6) δ 7.93-7.52 (4H), 7.18-6.99 (1H), 6.83-6.64 (1H), 5.24 (2H), 3.56-3.22 (2H), 3.11 (3H), 2.25 (3H), 2.09 (3H), 1.34-0.98 (3H); (M + 1): 483.2 |
| 88 | N'-(4-(2-(2-bromo-6-methylphenoxy)acetyl)-2,5-dimethylphenyl)-N-ethyl-N-methylformimidamide | $^1$H-NMR(400 MHz, DMSO-D6) δ 7.74 (s, 1H), 7.64 (s, 1H), 7.45 (d, 1H), 7.24 (d, 1H), 7.00 (t, 1H), 6.72 (d,, 1H), 5.10 (s, 2H), 3.46-3.35 (m, 2H), 2.97 (s, 3H), 2.45 (s, 3H), 2.28 (s, 3H), 2.15 (s, 3H), 1.14 (t, 3H); (M + 1): 418.95 |
| 89 | N'-(4-(2-(2-bromo-4,6-dimethylphenoxy)acetyl)-2,5-dimethylphenyl)-N-ethyl-N-methylformimidamide | $^1$H-NMR(400 MHz, DMSO-D6) δ 7.74 (s, 1H), 7.64 (s, 1H), 7.45 (d, 1H), 7.24 (d, 1H), 6.72 (d,, 1H), 5.10 (s, 2H), 3.46-3.35 (m, 2H), 2.97 (s, 3H), 2.45 (s, 3H), 2.28 (s, 6H), 2.15 (s, 3H), 1.14 (t, 3H); (M + 1): 432.9 |
| 90 | N'-(4-(2-(2-bromo-5-methylphenoxy)acetyl)-2,5-dimethylphenyl)-N-ethyl-N-methylformimidamide | $^1$H-NMR(400 MHz, DMSO-D6) δ 7.78 (d, 2H), 7.41 (d, 1H), 6.78 (s, 1H), 6.73-6.67 (m, 2H), 5.45 (s, 2H), 3.39-3.35 (m, 2H), 2.98 (s, 3H), 2.38 (s, 3H), 2.19 (s, 6H), 1.14 (t, 3H); (M + 1): 418.95 |
| 91 | N'-(4-(2-(2-chloro-6-methylphenoxy)acetyl)-2,5-dimethylphenyl)-N-ethyl-N-methylformimidamide | $^1$H-NMR(400 MHz, DMSO-D6) δ 7.79 (s, 1H), 7.64 (s, 1H), 7.30 (d, 1H), 7.20 (d, 1H), 7.06 (t, 1H), 6.73 (s, 1H), 5.12 (s, 2H), 3.39-3.35 (m, 2H), 2.97 (s, 3H), 2.44 (s, 3H), 2.26 (s, 3H), 2.15 (s, 3H), 1.13 (t, 3H); (M + 1): 373.8 |
| 92 | N'-(2,5-dimethyl-4-(N-methyl-N-(p-tolyl)glycyl)phenyl)-N-ethyl-N-methylformimidamide | $^1$H-NMR(400 MHz, DMSO-D6) δ 7.86-7.56 (2H), 7.20 (1H), 6.79-6.44 (4H), 4.88(m, 2H), 3.41-3.23 (m, 2H), 3.13(s, 3H), 2.68-2.08 (s, 12H), 1.31-1.06 (t, 3H); (M + 1): 352.5 |
| 93 | N'-(4-(2-(2-chloro-4-methylphenoxy)acetyl)-2,5-dimethylphenyl)-N-ethyl-N-methylformimidamide | $^1$H-NMR(400 MHz, DMSO-D6) δ 7.78 (d, 2H), 7.41 (d, 1H), 6.78 (s, 1H), 6.73-6.67 (m, 2H), 5.45 (s, 2H), 3.39-3.35 (m, 2H), 2.98 (s, 3H), 2.38 (s, 3H), 2.19 (s, 6H), 1.14 (t, 3H); (M + 1): 373.8 |
| 94 | N'-(4-(2-(2,4-dichlorophenoxy)acetyl)-2,5-dimethylphenyl)-N-ethyl-N-methylformimidamide | $^1$H-NMR(400 MHz, DMSO-D6) δ 7.78 (d, 2H), 7.41 (d, 1H), 6.78 (s, 1H), 6.73-6.67 (m, 2H), 5.45 (s, 2H), 3.39-3.35 (m, 2H), 2.98 (s, 3H), 2.38 (s, 3H), 2.19 (s, 6H), 1.14 (t, 3H); (M + 1): 394.3 |
| 95 | N'-(4-(2-(2,5-dimethylphenoxy)acetyl)-2,5-dimethylphenyl)-N-ethyl-N-methylformimidamide | $^1$H-NMR(400 MHz, DMSO-D6) δ 7.78 (d, 2H), 7.41 (d, 1H), 6.78 (s, 1H), 6.73-6.67 (m, 2H), 5.45 (s, 2H), 3.39-3.35 (m, 2H), 2.98 (s, 3H), 2.38 (s, 6H), 2.19 (s, 6H), 1.14 (t, 3H); (M + 1): 353.2 |
| 96 | N'-(4-(2-(5-chloro-2-methylphenoxy)acetyl)-2,5-dimethylphenyl)-N-ethyl-N-methylformimidamide | $^1$H-NMR(400 MHz, DMSO-D6) δ 7.78 (d, 2H), 7.41 (d, 1H), 6.78 (s, 1H), 6.73-6.67 (m, 2H), 5.45 (s, 2H), 3.39-3.35 (m, 2H), 2.98 (s, 3H), 2.38 (s, 3H), 2.19 (s, 6H), 1.14 (t, 3H); (M + 1): 373.8 |
| 97 | N'-(4-(2-(3,5-dichlorophenoxy)acetyl)-2,5-dimethylphenyl)-N-ethyl-N-methylformimidamide | $^1$H-NMR(400 MHz, DMSO-D6) δ 7.90-7.55 (2H), 7.48-7.29 (2H), 6.81-6.61 (1H), 5.02 (2H), 3.24 (3H), 2.86 (3H), 2.24 (3H), 1.99 (3H), 1.31-1.04 (3H); (M + 1): 394.3 |
| 98 | N'-(4-(2-(4-chloro-3-(trifluoromethyl)phenoxy)acetyl)-2,5-dimethylphenyl)-N-ethyl-N-methylformimidamide | $^1$H-NMR(400 MHz, DMSO-D6) δ 7.80-7.68 (m, 2H), 7.22 (d, 1H), 7.14 (d, 1H), 6.86 (dd, 1H), 6.72 (d, 1H), 5.37 (s, 2H), 3.47-3.35 (m, 2H), 2.98 (s, 3H), 2.37 (s, 3H), 2.25 (s, 3H), 1.15-1.07 (m, 3H); (M + 1): 427.6 |
| 99 | N'-(4-(2-(2,3-dimethylphenoxy)acetyl)-2,5-dimethylphenyl)-N-ethyl-N-methylformimidamide | $^1$H-NMR(400 MHz, DMSO-D6) δ 7.89-7.61 (2H), 7.07-6.89 (1H), 6.83-6.60 (3H), 5.40-5.17 (2H), 3.57-3.24 (2H), 2.94 (3H), 2.45 (3H), 2.26(6H), 2.14(3H), 1.33-1.03 (3H); (M + 1): 353.2 |
| 100 | N'-(4-(2-((2-chloro-6-methylphenyl)thio)acetyl)-2,5-dimethylphenyl)-N-ethyl-N-methylformimidamide | $^1$H-NMR(400 MHz, DMSO-D6) δ 7.74 (s, 1H), 7.64 (s, 1H), 7.45 (d, 1H), 7.24 (d, 1H), 7.00 (t, 1H), 6.72 (d,, 1H), 4.03 (s, 2H), 3.46-3.35 (m, 2H), 2.97 (s, 3H), 2.45 (s, 3H), 2.28 (s, 3H), 2.15 (s, 3H), 1.14 (t, 3H); (M + 1): 390 |
| 101 | N'-(4-(2-((3,5-dichlorophenyl)thio)acetyl)-2,5-dimethylphenyl)-N-ethyl-N-methylformimidamide | $^1$H-NMR(400 MHz, DMSO-D6) δ 7.90-7.55 (2H), 7.48-7.29 (2H), 6.81-6.61 (1H), 4.83-4.64 (2H), 3.24 (3H), 2.86 (3H), 2.24 (3H), 1.99 (3H), 1.31-1.04 (3H); (M + 1): 410.50 |
| 102 | N'-(4-(2-((2,4-difluorophenyl)thio)acetyl)-2,5-dimethylphenyl)-N-ethyl-N-methylformimidamide | $^1$H-NMR(400 MHz, DMSO-D6) δ 7.78 (d, 2H), 7.41 (d, 1H), 6.78 (s, 1H), 6.73-6.67 (m, 2H), 4.64 (s, 2H), 3.39-3.35 (m, 2H), 2.98 (s, 3H), 2.38 (s, 3H), 2.19 (s, 3H), 1.14 (t, 3H); (M + 1): 376.65 |

TABLE 1-continued

| | | |
|---|---|---|
| 103 | N'-(4-(2-((2,6-difluorophenyl)thio)acetyl)-2,5-dimethylphenyl)-N-ethyl-N-methylformimidamide | ¹H-NMR(400 MHz, DMSO-D6) δ 7.74 (s, 1H), 7.64 (s, 1H), 7.45 (d, 1H), 7.24 (d, 1H), 7.00 (t, 1H), 6.72 (d,, 1H), 4.03 (s, 2H), 3.46-3.35 (m, 2H), 2.97 (s, 3H), 2.28 (s, 3H), 2.15 (s, 3H), 1.14 (t, 3H); (M + 1): 376.65 |
| 104 | N'-(4-(2-((2-bromophenyl)thio)acetyl)-2-chloro-5-methylphenyl)-N,N-dimethylformimidamide | ¹H-NMR(400 MHz, DMSO-D6) δ 8.07 (s, 1H), 7.85 (s, 1H), 7.58 (d, 1H), 7.35-7.31 (m, 2H), 7.11-7.06 (m, 1H), 6.92 (s, 1H), 4.68 (s, 2H), 3.04 (s, 3H), 2.96 (s, 3H), 2.32 (s, 3H); (M + 1): 426.80 |
| 105 | N'-(2,5-dimethyl-4-(2-(3-(methylthio)phenoxy)acetyl)phenyl)-N,N-dimethylformimidamide | ¹H-NMR(400 MHz, DMSO-D6) δ 7.74-7.69 (m, 2H), 7.21-7.17 (m, 1H), 6.82-6.78 (m, 2H), 6.72 (s, 1H), 6.69 (dd, 1H), 5.37 (s, 2H), 3.03 (s, 3H), 2.96 (s, 3H), 2.43 (s, 3H), 2.38 (s, 3H), 2.19 (s, 3H); (M + 1): 357.45 |
| 106 | N'-(4-(2-((3-fluorophenyl)thio)acetyl)-2,5-dimethylphenyl)-N,N-dimethylformimidamide | ¹H-NMR(400 MHz, DMSO-D6) δ 7.78 (d, 2H), 7.67 (s, 1H), 7.34-7.28 (m, 1H), 7.18-7.22 (m, 1H), 7.14 (d, 1H), 6.96-7.00 (m, 1H), 4.62 (s, 2H), 3.06-2.89 (6H), 2.32 (s, 3H), 2.19 (s, 3H); (M + 1): 345.2 |
| 107 | N'-(4-(2-((2,6-dimethylphenyl)thio)acetyl)-2,5-dimethylphenyl)-N,N-dimethylformimidamide. | ¹H-NMR(400 MHz, DMSO-D6) δ 7.71 (d, 1H), 7.51 (s, 1H), 7.15-7.07 (m, 3H), 6.64 (d, 1H), 4.03 (s, 2H), 2.97 (s, 6H), 2.31 (s, 6H), 2.20 (s, 3H), 2.10 (s, 3H); (M + 1): 355.15 |
| 108 | N'-(4-(2-(2-chlorophenoxy)acetyl)-2,5-dimethylphenyl)-N-ethyl-N-methylformimidamide | ¹H-NMR(400 MHz, DMSO-D6) δ 7.73 (d, 1H), 7.63 (s, 1H), 7.02 (d, 2H), 6.92 (dd, 2H), 6.73 (s, 1H), 4.99 (s, 2H), 3.46-3.35 (m, 2H), 2.97 (s, 3H), 2.22 (s, 3H), 2.15 (s, 3H), 1.13 (t, 3H); (M + 1): 359.10 |
| 109 | N'-(4-(2-(2-chlorophenoxy)acetyl)-2,5-dimethylphenyl)-N,N-dimethylformimidamide | ¹H-NMR(400 MHz, DMSO-D6) δ 7.73 (d, 1H), 7.63 (s, 1H), 7.02 (d, 2H), 6.92 (dd, 2H), 6.73 (s, 1H), 4.99 (s, 2H), 2.97 (s, 6H), 2.22 (s, 3H), 2.15 (s, 3H); (M + 1): 345.1 |
| 110 | N-ethyl-N'-(4-(2-(2-methoxyphenoxy)acetyl)-2,5-dimethylphenyl)-N-methylformimidamide | ¹H-NMR(400 MHz, DMSO-D6) δ 7.73 (d, 1H), 7.63 (s, 1H), 7.02 (d, 2H), 6.92 (dd, 2H), 6.73 (s, 1H), 4.99 (s, 2H), 3.58 (s, 3H), 3.46-3.35 (m, 2H), 2.97 (s, 3H), 2.22 (s, 3H), 2.15 (s, 3H), 1.13 (t, 3H); (M + 1): 355.2 |
| 111 | N-ethyl-N'-(4-(2-(3-(ethylthio)phenoxy)acetyl)-2,5-dimethylphenyl)-N-methylformimidamide | ¹H-NMR(400 MHz, DMSO-D6) δ 7.68-7.80 (m, 2H), 7.19 (t, 1H), 6.77-6.82 (m, 2H), 6.67-6.73 (m, 2H), 5.35 (s, 2H), 3.53-3.34 (2H), 3.05-2.89 (3H), 2.43 (s, 2H), 2.38 (s, 3H), 2.20 (s, 3H), 1.12-1.16 (m, 6H); (M + 1): 385.5 |
| 112 | N'-(2-bromo-4-(2-((3-fluorophenyl)thio)acetyl)-3,6-dimethylphenyl)-N-ethyl-N-methylformimidamide | ¹H-NMR(400 MHz, DMSO-D6) δ 7.68 (s, 1H), 7.44-7.29 (m, 2H), 7.20 (dt, 1H), 7.14-7.12 (m, 1H), 7.00 (td, 1H), 4.62 (s, 2H), 3.40 (q, 2H), 2.94 (s, 3H), 2.27 (s, 3H), 2.12 (s, 3H), 1.13 (t, 3H); (M + 1): 439.00 |
| 113 | N'-(2,5-dimethyl-4-(2-(3-(trifluoromethoxy)phenoxy)acetyl)phenyl)-N-ethyl-N-methylformimidamide | ¹H-NMR(400 MHz, DMSO-D6) δ 7.74-7.70 (m, 2H), 7.38 (t, 1H), 6.96 (dd, 1H), 6.91 (d, 2H), 6.72 (d, 1H), 5.45 (s, 2H), 3.47-3.34 (m, 2H), 2.98 (s, 3H), 2.38 (s, 3H), 2.21 (s, 3H), 1.14 (t, 3H); (M + 1): 409.20 |
| 114 | N'-(4-(2-(4H-1,2,4-triazol-4-yl)acetyl)-2,5-dimethylphenyl)-N-ethyl-N-methylformimidamide | ¹H-NMR(400 MHz, DMSO-D6) δ 8.46 (s, 1H), 7.98 (s, 1H), 7.83-7.71 (m, 2H), 6.75 (d, 1H), 5.80 (s, 2H), 3.48-3.35 (m, 2H), 2.98 (s, 3H), 2.39 (s, 3H), 2.22 (s, 3H), 1.14 (t, 3H); (M + 1): 300.30 |
| 115 | N'-(2,5-dimethyl-4-(2-(3-(trifluoromethoxy)phenoxy)acetyl)phenyl)-N,N-dimethylformimidamide | ¹H-NMR(400 MHz, DMSO-D6) δ 7.74-7.70 (m, 2H), 7.38 (t, 1H), 6.98-6.90 (m, 3H), 6.72 (s, 1H), 5.45 (s, 2H), 3.00 (s, 6H), 2.38 (s, 3H), 2.21 (s, 3H); (M + 1): 395.20 |
| 116 | N'-(4-(2-(benzo[d]thiazol-2-ylthio)acetyl)-2,5-dimethylphenyl)-N,N-dimethylformimidamide | ¹H-NMR(400 MHz, DMSO-D6) δ 7.99 (d, 1H), 7.83 (s, 1H), 7.79-7.76 (m, 2H), 7.44 (td, 1H), 7.36-7.32 (m, 1H), 6.72 (s, 1H), 5.01 (s, 2H), 3.00 (d, 6H), 2.37 (s, 3H), 2.22 (s, 3H); (M + 1): 384.10 |
| 117 | N'-(4-(2-(4H-1,2,4-triazol-4-yl)acetyl)-2,5-dimethylphenyl)-N,N-dimethylformimidamide | ¹H-NMR(400 MHz, DMSO-D6) δ 8.47 (d, 1H), 7.98 (d, 1H), 7.81 (s, 1H), 7.77 (s, 1H), 6.74 (s, 1H), 5.80 (s, 2H), 3.00 (s, 6H), 2.39 (s, 3H), 2.22 (s, 3H); (M + 1): 285.70 |
| 118 | N'-(2,5-dimethyl-4-(2-(4-(trifluoromethyl)phenoxy)acetyl)phenyl)-N,N-dimethylformimidamide | ¹H-NMR(400 MHz, DMSO-D6) δ 7.88-7.76 (m, 2H), 7.65-7.56 (m, 2H), 7.12-7.05 (m, 2H), 6.75-6.72 (m, 1H), 5.50 (s, 2H), 3.02 (s, 6H), 2.38 (s, 3H), 2.16 (s, 3H); (M + 1): 379.15 |
| 119 | N'-(2-chloro-4-(2-(2,5-dimethylphenoxy)acetyl)-5-methylphenyl)-N-ethyl-N-methylformimidamide | ¹H-NMR(400 MHz, DMSO-D6) δ 7.96 (s, 1H), 7.84 (d, 1H), 6.98 (d, 1H), 6.92 (d, 1H), 6.66 (s, 1H), 6.62 (d, 1H), 5.31 (s, 2H), 3.48-3.36 (m, 2H), 3.00 (s, 3H), 2.36 (s, 3H), 2.20 (s, 3H), 2.11 (s, 3H), 1.14 (t, 3H); (M + 1): 373.8 |
| 120 | N'-(4-(2-(2-bromo-4-methylphenoxy)acetyl)-2-chloro-5-methylphenyl)-N-ethyl-N-methylformimidamide | ¹H-NMR(400 MHz, DMSO-D6) δ 7.96 (s, 1H), 7.85 (d, 1H), 7.22 (d, 1H), 7.18 (d, 1H), 6.94 (d, 1H), 6.88 (dd, 1H), 5.40 (s, 2H), 3.44 (q, 2H), 3.01 (s, 3H), 2.38 (s, 3H), 2.24 (s, 3H), 1.18-1.12 (m, 3H); (M + 1): 438.5 |
| 121 | N'-(2-chloro-4-(2-(5-chloro-2-methylphenoxy)acetyl)-5-methylphenyl)-N-ethyl-N-methylformimidamide | ¹H-NMR(400 MHz, DMSO-D6) δ 7.99 (s, 1H), 7.85 (d, 1H), 7.15 (d, 1H), 6.99 (d, 1H), 6.93 (d, 1H), 6.88 (dd, 1H), 5.45 (s, 2H), 3.44 (q, 2H), 3.00 (s, 3H), 2.38 (s, 3H), 2.16 (s, 3H), 1.17-1.12 (m, 3H); (M + 1): 394.2 |
| 122 | N'-(4-(2-(2-bromo-4-methoxyphenoxy)acetyl)-2-chloro-5-methylphenyl)-N-ethyl-N-methylformimidamide | ¹H-NMR(400 MHz, DMSO-D6) δ 7.67-7.79 (in, 2H), 6.80-6.86 (m, 3H), 6.71 (d, 1H), 5.24 (s, 2H), 3.69 (s, 3H), 3.50-3.34 (2H), 3.05-2.89 (3H), 2.19 (s, 3H), 1.14 (t, 3H); (M + 1): 455.20 |

TABLE 1-continued

| Compd. No. | Compound |
|---|---|
| 123 | N-ethyl-N'-(4-(3-(4-fluorophenyl)propanoyl)-2,5-dimethylphenyl)-N-methylformimidamide |
| 124 | N-ethyl-N'-(2-fluoro-5-methyl-4-(3-(o-tolyl)propanoyl)phenyl)-N-methylformimidamide |
| 125 | N'-(5-chloro-4-(3-(2-fluorophenyl)propanoyl)-2-methylphenyl)-N-ethyl-N-methylformimidamide |
| 126 | N'-(2-chloro-4-(3-(3-fluorophenyl)propanoyl)-5-methylphenyl)-N-ethyl-N-methylformimidamide |
| 127 | N-ethyl-N'-(5-fluoro-4-(2-((2-fluorophenyl)thio)acetyl)-2-methylphenyl)-N-methylformimidamide |
| 128 | N-ethyl-N'-(5-fluoro-4-(2-(3-fluorophenoxy)acetyl)-2-methylphenyl)-N-methylformimidamide |
| 129 | N-ethyl-N'-(5-fluoro-4-(2-((4-fluorophenyl)thio)acetyl)-2-methylphenyl)-N-methylformimidamide |
| 130 | N-ethyl-N'-(5-fluoro-4-(2-((2-fluoro-6-methylphenyl)thio)acetyl)-2-methylphenyl)-N-methylformimidamide |
| 131 | N-ethyl-N'-(5-fluoro-4-(N-(2-fluorophenyl)-N-methylglycyl)-2-methylphenyl)-N-methylformimidamide |
| 132 | N-ethyl-N'-(5-fluoro-4-(N-(3-fluorophenyl)-N-methylglycyl)-2-methylphenyl)-N-methylformimidamide |
| 133 | N-ethyl-N'-(5-fluoro-4-(N-(4-fluorophenyl)-N-methylglycyl)-2-methylphenyl)-N-methylformimidamide |
| 134 | N-ethyl-N'-(5-fluoro-4-(N-(2-fluoro-6-methylphenyl)-N-methylglycyl)-2-methylphenyl)-N-methylformimidamide |
| 135 | N-ethyl-N'-(2-fluoro-4-(N-(2-fluorophenyl)-N-methylglycyl)-5-methylphenyl)-N-methylformimidamide |
| 136 | N-ethyl-N'-(2-fluoro-4-(N-(3-fluorophenyl)-N-methylglycyl)-5-methylphenyl)-N-methylformimidamide |
| 137 | N-ethyl-N'-(2-fluoro-4-(N-(4-fluorophenyl)-N-methylglycyl)-5-methylphenyl)-N-methylformimidamide |
| 138 | N-ethyl-N'-(2-fluoro-4-(N-(2-fluoro-6-methylphenyl)-N-methylglycyl)-5-methylphenyl)-N-methylformimidamide |
| 139 | N'-(5-chloro-4-(N-(2-fluorophenyl)-N-methylglycyl)-2-methylphenyl)-N-ethyl-N-methylformimidamide |
| 140 | N'-(5-chloro-4-(N-(3-fluorophenyl)-N-methylglycyl)-2-methylphenyl)-N-ethyl-N-methylformimidamide |
| 141 | N'-(5-chloro-4-(N-(4-fluorophenyl)-N-methylglycyl)-2-methylphenyl)-N-ethyl-N-methylformimidamide |
| 142 | N'-(5-chloro-4-(N-(2-fluoro-6-methylphenyl)-N-methylglycyl)-2-methylphenyl)-N-ethyl-N-methylformimidamide |
| 143 | N'-(2-Fluoro-4-((2-fluorophenyl)glycyl)-5-methylphenyl)-N-ethyl-N-methylformimidamide |
| 144 | N'-(2-Fluoro-4-((3-fluorophenyl)glycyl)-5-methylphenyl)-N-ethyl-N-methylformimidamide |
| 145 | N'-(2-Fluoro-4-((4-fluorophenyl)glycyl)-5-methylphenyl)-N-ethyl-N-methylformimidamide |
| 146 | N'-(2-Fluoro-4-((2-fluoro-6-methylphenyl)glycyl)-5-methylphenyl)-N-ethyl-N-methylformimidamide |
| 147 | N'-(2-chloro-4-((2-fluorophenyl)glycyl)-5-methylphenyl)-N-ethyl-N-methylformimidamide |
| 148 | N'-(2-chloro-4-((3-fluorophenyl)glycyl)-5-methylphenyl)-N-ethyl-N-methylformimidamide |
| 149 | N'-(2-chloro-4-((4-fluorophenyl)glycyl)-5-methylphenyl)-N-ethyl-N-methylformimidamide |
| 150 | N'-(2-chloro-4-((2-fluoro-6-methylphenyl)glycyl)-5-methylphenyl)-N-ethyl-N-methylformimidamide |
| 151 | N'-(2-chloro-4-(N-(2-fluorophenyl)-N-methylglycyl)-5-methylphenyl)-N-ethyl-N-methylformimidamide |
| 152 | N'-(2-chloro-4-(N-(3-fluorophenyl)-N-methylglycyl)-5-methylphenyl)-N-ethyl-N-methylformimidamide |
| 153 | N'-(2-chloro-4-(N-(4-fluorophenyl)-N-methylglycyl)-5-methylphenyl)-N-ethyl-N-methylformimidamide |
| 154 | N'-(2-chloro-4-(N-(2-fluoro-6-methylphenyl)-N-methylglycyl)-5-methylphenyl)-N-ethyl-N-methylformimidamide |
| 155 | N-ethyl-N'-(4-(N-(2-fluorophenyl)-N-methylglycyl)-2,5-dimethylphenyl)-N-methylformimidamide |
| 156 | N-ethyl-N'-(4-(N-(3-fluorophenyl)-N-methylglycyl)-2,5-dimethylphenyl)-N-methylformimidamide |
| 157 | N-ethyl-N'-(4-(N-(4-fluorophenyl)-N-methylglycyl)-2,5-dimethylphenyl)-N-methylformimidamide |
| 158 | N-ethyl-N'-(4-(N-(2-fluoro-6-methylphenyl)-N-methylglycyl)-2,5-dimethylphenyl)-N-methylformimidamide |
| 159 | N-ethyl-N'-(4-(N-(5-fluoro-2-methylphenyl)-N-methylglycyl)-2,5-dimethylphenyl)-N-methylformimidamide |
| 160 | N-ethyl-N'-(4-(N-(4-fluoro-2-methylphenyl)-N-methylglycyl)-2,5-dimethylphenyl)-N-methylformimidamide |
| 161 | N-ethyl-N'-(4-(N-(3-fluoro-2-methylphenyl)-N-methylglycyl)-2,5-dimethylphenyl)-N-methylformimidamide |
| 162 | N'-(4-(N-(2-chloro-6-fluorophenyl)-N-methylglycyl)-2,5-dimethylphenyl)-N-ethyl-N-methylformimidamide |
| 163 | N-ethyl-N'-(4-(N-(3-fluoro-4-methylphenyl)-N-methylglycyl)-2,5-dimethylphenyl)-N-methylformimidamide |
| 164 | N'-(4-(N-(4-chloro-3-fluorophenyl)-N-methylglycyl)-2,5-dimethylphenyl)-N-ethyl-N-methylformimidamide |
| 165 | N'-(4-(N-(2-chloro-5-fluorophenyl)-N-methylglycyl)-2,5-dimethylphenyl)-N-ethyl-N-methylformimidamide |
| 166 | N'-(4-(N-(2-chloro-4-fluorophenyl)-N-methylglycyl)-2,5-dimethylphenyl)-N-ethyl-N-methylformimidamide |
| 167 | N'-(4-(N-(2-chloro-3-fluorophenyl)-N-methylglycyl)-2,5-dimethylphenyl)-N-ethyl-N-methylformimidamide |
| 168 | N'-(4-(N-(4-bromo-3-fluorophenyl)-N-methylglycyl)-2,5-dimethylphenyl)-N-ethyl-N-methylformimidamide |
| 169 | N'-(4-(N-(4-bromo-2-methylphenyl)-N-methylglycyl)-2,5-dimethylphenyl)-N-ethyl-N-methylformimidamide |
| 170 | N'-(4-(N-(4-bromo-2-fluorophenyl)-N-methylglycyl)-2,5-dimethylphenyl)-N-ethyl-N-methylformimidamide |
| 171 | N'-(4-(N-(2,4-difluorophenyl)-N-methylglycyl)-2,5-dimethylphenyl)-N-ethyl-N-methylformimidamide |
| 172 | N'-(4-(N-(2,6-difluorophenyl)-N-methylglycyl)-2,5-dimethylphenyl)-N-ethyl-N-methylformimidamide |
| 173 | N'-(4-(N-(3,4-difluorophenyl)-N-methylglycyl)-2,5-dimethylphenyl)-N-ethyl-N-methylformimidamide |
| 174 | N'-(4-(N-(3,5-difluorophenyl)-N-methylglycyl)-2,5-dimethylphenyl)-N-ethyl-N-methylformimidamide |
| 175 | N'-(4-(N-(3,5-dimethoxyphenyl)-N-methylglycyl)-2,5-dimethylphenyl)-N-ethyl-N-methylformimidamide |
| 176 | N'-(4-(N-(3-chloro-5-methoxyphenyl)-N-methylglycyl)-2,5-dimethylphenyl)-N-ethyl-N-methylformimidamide |
| 177 | N'-(4-(N-(5-chloro-2-methoxyphenyl)-N-methylglycyl)-2,5-dimethylphenyl)-N-ethyl-N-methylformimidamide |
| 178 | N'-(4-(N-(3-chloro-2-methoxyphenyl)-N-methylglycyl)-2,5-dimethylphenyl)-N-ethyl-N-methylformimidamide |
| 179 | N'-(4-(N-(3-chloro-4-methoxyphenyl)-N-methylglycyl)-2,5-dimethylphenyl)-N-ethyl-N-methylformimidamide |
| 180 | N'-(4-(N-(3-chlorophenyl)-N-methylglycyl)-2,5-dimethylphenyl)-N-ethyl-N-methylformimidamide |
| 181 | N'-(4-(N-(2-chlorophenyl)-N-methylglycyl)-2,5-dimethylphenyl)-N-ethyl-N-methylformimidamide |
| 182 | N'-(4-(N-(4-chlorophenyl)-N-methylglycyl)-2,5-dimethylphenyl)-N-ethyl-N-methylformimidamide |
| 183 | N-ethyl-N'-(4-((3-fluorophenyl)glycyl)-2,5-dimethylphenyl)-N-methylformimidamide |
| 184 | N-ethyl-N'-(4-((2-fluorophenyl)glycyl)-2,5-dimethylphenyl)-N-methylformimidamide |
| 185 | N-ethyl-N'-(4-((4-fluorophenyl)glycyl)-2,5-dimethylphenyl)-N-methylformimidamide |
| 186 | N-ethyl-N'-(4-((2-fluoro-6-methylphenyl)glycyl)-2,5-dimethylphenyl)-N-methylformimidamide |
| 187 | N-ethyl-N'-(4-((4-fluoro-2-methylphenyl)glycyl)-2,5-dimethylphenyl)-N-methylformimidamide |
| 188 | N-ethyl-N'-(4-((3-fluoro-2-methylphenyl)glycyl)-2,5-dimethylphenyl)-N-methylformimidamide |
| 189 | N-ethyl-N'-(4-((3-fluoro-4-methylphenyl)glycyl)-2,5-dimethylphenyl)-N-methylformimidamide |
| 190 | N-ethyl-N'-(4-((5-fluoro-2-methylphenyl)glycyl)-2,5-dimethylphenyl)-N-methylformimidamide |
| 191 | N'-(4-((2-chloro-6-fluorophenyl)glycyl)-2,5-dimethylphenyl)-N-ethyl-N-methylformimidamide |
| 192 | N'-(4-((2-chloro-5-fluorophenyl)glycyl)-2,5-dimethylphenyl)-N-ethyl-N-methylformimidamide |

TABLE 1-continued

| | |
|---|---|
| 193 | N'-(4-((2-chloro-4-fluorophenyl)glycyl)-2,5-dimethylphenyl)-N-ethyl-N-methylformimidamide |
| 194 | N'-(4-((2-chloro-3-fluorophenyl)glycyl)-2,5-dimethylphenyl)-N-ethyl-N-methylformimidamide |
| 195 | N'-(4-((4-chloro-3-fluorophenyl)glycyl)-2,5-dimethylphenyl)-N-ethyl-N-methylformimidamide |
| 196 | N'-(4-((4-bromo-3-fluorophenyl)glycyl)-2,5-dimethylphenyl)-N-ethyl-N-methylformimidamide |
| 197 | N'-(4-((4-bromo-2-methylphenyl)glycyl)-2,5-dimethylphenyl)-N-ethyl-N-methylformimidamide |
| 198 | N'-(4-((4-bromo-2-fluorophenyl)glycyl)-2,5-dimethylphenyl)-N-ethyl-N-methylformimidamide |
| 199 | N'-(4-((2,4-difluorophenyl)glycyl)-2,5-dimethylphenyl)-N-ethyl-N-methylformimidamide |
| 200 | N'-(4-((2,6-difluorophenyl)glycyl)-2,5-dimethylphenyl)-N-ethyl-N-methylformimidamide |
| 201 | N'-(4-((3,4-difluorophenyl)glycyl)-2,5-dimethylphenyl)-N-ethyl-N-methylformimidamide |
| 202 | N'-(4-((3,5-difluorophenyl)glycyl)-2,5-dimethylphenyl)-N-ethyl-N-methylformimidamide |
| 203 | N'-(4-((3,5-dimethoxyphenyl)glycyl)-2,5-dimethylphenyl)-N-ethyl-N-methylformimidamide |
| 204 | N'-(4-((3-chloro-5-methoxyphenyl)glycyl)-2,5-dimethylphenyl)-N-ethyl-N-methylformimidamide |
| 205 | N'-(4-((5-chloro-2-methoxyphenyl)glycyl)-2,5-dimethylphenyl)-N-ethyl-N-methylformimidamide |
| 206 | N'-(4-((3-chloro-2-methoxyphenyl)glycyl)-2,5-dimethylphenyl)-N-ethyl-N-methylformimidamide |
| 207 | N'-(4-((3-chloro-4-methoxyphenyl)glycyl)-2,5-dimethylphenyl)-N-ethyl-N-methylformimidamide |
| 208 | N'-(4-((3-chlorophenyl)glycyl)-2,5-dimethylphenyl)-N-ethyl-N-methylformimidamide |
| 209 | 1-(5-chloro-2-methyl-4-((1-methylpyrrolidin-2-ylidene)amino)phenyl)-2-((4-chlorophenyl)thio)ethan-1-one |
| 210 | 2-((4-bromophenyl)thio)-1-(2,5-dimethyl-4-((1-methylpyrrolidin-2-ylidene)amino)phenyl)ethan-1-one |
| 211 | 1-(5-chloro-2-methyl-4-((1-methylpyrrolidin-2-ylidene)amino)phenyl)-2-((3-fluorophenyl)thio)ethan-1-one |
| 212 | N'-(2,5-dimethyl-4-(3-methyl-1-(methyl(phenyl)amino)but-2-en-2-yl)phenyl)-N-ethyl-N-methylformimidamide |
| 213 | N'-(4-(3-((2,6-difluorophenyl)(methyl)amino)prop-1-en-2-yl)-2,5-dimethylphenyl)-N-ethyl-N-methylformimidamide |
| 214 | N'-(4-((2-chlorophenyl)glycyl)-2,5-dimethylphenyl)-N-ethyl-N-methylformimidamide |
| 215 | N'-(4-((4-chlorophenyl)glycyl)-2,5-dimethylphenyl)-N-ethyl-N-methylformimidamide |
| 216 | N'-(4-(2-(1H-benzo[d]imidazol-1-yl)acetyl)-2,5-dimethylphenyl)-N-ethyl-N-methylformimidamide |
| 217 | N'-(4-(2-(1H-indol-1-yl)acetyl)-2,5-dimethylphenyl)-N-ethyl-N-methylformimidamide |
| 218 | N'-(4-(2-(1H-imidazo[4,5-b]pyridin-1-yl)acetyl)-2,5-dimethylphenyl)-N-ethyl-N-methylformimidamide |
| 219 | N'-(2,5-dimethyl-4-(2-(3-methyl-1H-pyrrol-1-yl)acetyl)phenyl)-N-ethyl-N-methylformimidamide |
| 220 | N'-(4-(2-(2H-isoindol-2-yl)acetyl)-2,5-dimethylphenyl)-N-ethyl-N-methylformimidamide |
| 221 | N'-(2,5-dimethyl-4-(2-(2-oxopyridin-1(2H)-yl)acetyl)phenyl)-N-ethyl-N-methylformimidamide |
| 222 | N'-(4-(2-(1H-pyrazol-1-yl)acetyl)-2,5-dimethylphenyl)-N-ethyl-N-methylformimidamide |
| 223 | N'-(2,5-dimethyl-4-(2-(4,5,6,7-tetrahydro-1H-indazol-1-yl)acetyl)phenyl)-N-ethyl-N-methylformimidamide |
| 224 | N'-(2,5-dimethyl-4-(2-(4,5,6,7-tetrahydro-1H-indol-1-yl)acetyl)phenyl)-N-ethyl-N-methylformimidamide |
| 225 | N'-(2,5-dimethyl-4-(2-(4,5,6,7-tetrahydro-2H-isoindol-2-yl)acetyl)phenyl)-N-ethyl-N-methylformimidamide |
| 226 | N'-(4-(2-(benzo[d]thiazol-3(2H)-yl)acetyl)-2,5-dimethylphenyl)-N-ethyl-N-methylformimidamide |
| 227 | N-ethyl-N'-(4-(2-(3-fluorophenoxy)-1-(methylimino)ethyl)-2,5-dimethylphenyl)-N-methylformimidamide |
| 228 | N-ethyl-N'-(4-(2-(4-methoxyphenoxy)-1-(methylimino)ethyl)-2,5-dimethylphenyl)-N-methylformimidamide |
| 229 | N'-(4-(2-((3,4-dimethylphenyl)thio)-1-(methylimino)ethyl)-2,5-dimethylphenyl)-N-ethyl-N-methylformimidamide |
| 230 | N'-(2,5-dimethyl-4-(1-(methylimino)-2-(m-tolyloxy)ethyl)phenyl)-N-ethyl-N-methylformimidamide |
| 231 | N'-(4-(2-(3-chlorophenoxy)-1-(methylimino)ethyl)-2,5-dimethylphenyl)-N-ethyl-N-methylformimidamide |
| 232 | N'-(2,5-dimethyl-4-(1-(methylimino)-2-(4-(trifluoromethoxy)phenoxy)ethyl)phenyl)-N-ethyl-N-methylformimidamide |
| 233 | N'-(2,5-dimethyl-4-(1-(methylimino)-2-(p-tolyloxy)ethyl)phenyl)-N-ethyl-N-methylformimidamide |
| 234 | N'-(4-(2-(4-chlorophenoxy)-1-(methylimino)ethyl)-2,5-dimethylphenyl)-N-ethyl-N-methylformimidamide |
| 235 | N'-(2,5-dimethyl-4-(1-(methylimino)-2-(3-(methylthio)phenoxy)ethyl)phenyl)-N-ethyl-N-methylformimidamide |
| 236 | N'-(4-(2-((3-chloro-5-(trifluoromethyl)pyridin-2-yl)thio)-1-(methylimino)ethyl)-2,5-dimethylphenyl)-N-ethyl-N-methylformimidamide |
| 237 | N'-(2-chloro-5-methyl-4-(1-(methylimino)-2-phenoxyethyl)phenyl)-N-ethyl-N-methylformimidamide |
| 238 | N'-(2-chloro-4-(2-(3-chlorophenoxy)-1-(methylimino)ethyl)-5-methylphenyl)-N-ethyl-N-methylformimidamide |
| 239 | N'-(2-chloro-4-(2-(4-chlorophenoxy)-1-(methylimino)ethyl)-5-methylphenyl)-N-ethyl-N-methylformimidamide |
| 240 | N'-(4-(2-((4-bromophenyl)thio)-1-(methylimino)ethyl)-2,5-dimethylphenyl)-N-ethyl-N-methylformimidamide |
| 241 | N'-(4-(2-(3-bromophenoxy)-1-(methylimino)ethyl)-2-chloro-5-methylphenyl)-N-ethyl-N-methylformimidamide |
| 242 | N'-(2-chloro-4-(2-(3-fluorophenoxy)-1-(methylimino)ethyl)-5-methylphenyl)-N-ethyl-N-methylformimidamide |
| 243 | N'-(2-chloro-5-methyl-4-(1-(methylimino)-2-(p-tolyloxy)ethyl)phenyl)-N-ethyl-N-methylformimidamide |
| 244 | N'-(2-chloro-5-methyl-4-(1-(methylimino)-2-(m-tolyloxy)ethyl)phenyl)-N-ethyl-N-methylformimidamide |
| 245 | N-ethyl-N'-(4-(2-((3-methoxyphenyl)thio)-1-(methylimino)ethyl)-2,5-dimethylphenyl)-N-methylformimidamide |
| 246 | N-ethyl-N'-(4-(2-((4-fluorophenyl)thio)-1-(methylimino)ethyl)-2,5-dimethylphenyl)-N-methylformimidamide |
| 247 | N'-(4-(2-((4-chlorophenyl)thio)-1-(methylimino)ethyl)-2,5-dimethylphenyl)-N-ethyl-N-methylformimidamide |
| 248 | N'-(4-(2-((2-bromophenyl)thio)-1-(methylimino)ethyl)-2,5-dimethylphenyl)-N-ethyl-N-methylformimidamide |
| 249 | N'-(4-(2-(2-bromophenoxy)-1-(methylimino)ethyl)-2-chloro-5-methylphenyl)-N-ethyl-N-methylformimidamide |
| 250 | N-ethyl-N'-(4-(2-(2-fluorophenoxy)-1-(methylimino)ethyl)-2,5-dimethylphenyl)-N-methylformimidamide |
| 251 | N-ethyl-N'-(4-(2-(4-fluorophenoxy)-1-(methylimino)ethyl)-2,5-dimethylphenyl)-N-methylformimidamide |
| 252 | N'-(4-(2-(2-bromophenoxy)-1-(methylimino)ethyl)-2,5-dimethylphenyl)-N-ethyl-N-methylformimidamide |
| 253 | N'-(2-chloro-5-methyl-4-(1-(methylimino)-2-(m-tolylthio)ethyl)phenyl)-N-ethyl-N-methylformimidamide |
| 254 | N'-(4-(2-((3-bromophenyl)thio)-1-(methylimino)ethyl)-2-chloro-5-methylphenyl)-N-ethyl-N-methylformimidamide |

TABLE 1-continued

| | |
|---|---|
| 255 | N'-(2-chloro-4-((Z)-2-((3-fluorophenyl)thio)-1-(methylimino)ethyl)-5-methylphenyl)-N-ethyl-N-methylformimidamide |
| 256 | N'-(2-chloro-4-((Z)-2-((4-chlorophenyl)thio)-1-(methylimino)ethyl)-5-methylphenyl)-N-ethyl-N-methylformimidamide |
| 257 | N'-(4-((Z)-2-((2-bromophenyl)thio)-1-(methylimino)ethyl)-2-chloro-5-methylphenyl)-N-ethyl-N-methylformimidamide |
| 258 | N'-(2,5-dimethyl-4-(1-(m-tolyloxy)cyclopropane-1-carbonyl)phenyl)-N-ethyl-N-methylformimidamide |
| 259 | N'-(2,5-dimethyl-4-(1-(o-tolyloxy)cyclopropane-1-carbonyl)phenyl)-N-ethyl-N-methylformimidamide |
| 260 | N'-(4-(2-cyano-2-((2,6-dimethylphenyl)thio)acetyl)-2,5-dimethylphenyl)-N-ethyl-N-methylformimidamide |
| 261 | N'-(4-(2-cyano-2-(m-tolylthio)propanoyl)-2,5-dimethylphenyl)-N-ethyl-N-methylformimidamide |
| 262 | N'-(4-(2-((4-chlorophenyl)(methyl)amino)-2-cyanoacetyl)-2,5-dimethylphenyl)-N-ethyl-N-methylformimidamide |
| 263 | N'-(4-(2-cyano-2-(methyl(phenyl)amino)acetyl)-2,5-dimethylphenyl)-N-ethyl-N-methylformimidamide |
| 264 | N'-(4-(2-cyano-2-(2,6-dichlorophenoxy)acetyl)-2,5-dimethylphenyl)-N-ethyl-N-methylformimidamide |
| 265 | N'-(4-(2-cyano-2-(2,6-dibromophenoxy)acetyl)-2,5-dimethylphenyl)-N-ethyl-N-methylformimidamide |
| 266 | N'-(4-(2-(2-bromo-6-methylphenoxy)-2-cyanoacetyl)-2,5-dimethylphenyl)-N-ethyl-N-methylformimidamide |
| 267 | N'-(4-(2-(dimethylamino)-2-(p-tolyloxy)acetyl)-2,5-dimethylphenyl)-N-ethyl-N-methylformimidamide |
| 268 | N'-(4-(2-(dimethylamino)-2-(m-tolyloxy)acetyl)-2,5-dimethylphenyl)-N-ethyl-N-methylformimidamide |
| 269 | N'-(4-(2-(dimethylamino)-2-phenoxyacetyl)-2,5-dimethylphenyl)-N-ethyl-N-methylformimidamide |
| 270 | N'-(2,5-dimethyl-4-(2-methyl-2-(phenylamino)propanoyl)phenyl)-N-ethyl-N-methylformimidamide |
| 271 | N'-(2,5-dimethyl-4-(1-(methyl(phenyl)amino)cyclopropane-1-carbonyl)phenyl)-N-ethyl-N-methylformimidamide |
| 272 | N'-(2,5-dimethyl-4-(1-phenoxycyclopropane-1-carbonyl)phenyl)-N-ethyl-N-methylformimidamide |
| 273 | N'-(2,5-dimethyl-4-(2-methyl-2-phenoxypropanoyl)phenyl)-N-ethyl-N-methylformimidamide |
| 274 | N'-(4-(2,2-difluoro-2-phenoxyacetyl)-2,5-dimethylphenyl)-N-ethyl-N-methylformimidamide |
| 275 | N'-(4-(2-(4-chlorophenoxy)-2,2-difluoroacetyl)-2,5-dimethylphenyl)-N-ethyl-N-methylformimidamide |
| 276 | N-ethyl-N'-(4-(2-fluoro-2-phenoxyacetyl)-2,5-dimethylphenyl)-N-methylformimidamide |
| 277 | N'-(4-(2,2-difluoro-2-(phenylthio)acetyl)-2,5-dimethylphenyl)-N-ethyl-N-methylformimidamide |
| 278 | N'-(4-(1,1-difluoro-3-phenoxyprop-1-en-2-yl)-2,5-dimethylphenyl)-N-ethyl-N-methylformimidamide |
| 279 | N'-(4-(1,1-difluoro-3-(phenylthio)prop-1-en-2-yl)-2,5-dimethylphenyl)-N-ethyl-N-methylformimidamide |
| 280 | N-ethyl-N'-(4-(2-(2-fluorophenoxy)ethanethioyl)-2,5-dimethylphenyl)-N-methylformimidamide |
| 281 | N'-(2,5-dimethyl-4-(2-(o-tolyloxy)ethanethioyl)phenyl)-N-ethyl-N-methylformimidamide |
| 282 | N'-(4-(2-(2-bromophenoxy)ethanethioyl)-2,5-dimethylphenyl)-N-ethyl-N-methylformimidamide |
| 283 | N'-(4-(2-((4-bromo-2-methylphenyl)amino)ethanethioyl)-2,5-dimethylphenyl)-N-ethyl-N-methylformimidamide |
| 284 | N'-(4-(2-((4-bromo-2-fluorophenyl)amino)ethanethioyl)-2,5-dimethylphenyl)-N-ethyl-N-methylformimidamide |
| 285 | N'-(4-(2-((2,4-difluorophenyl)amino)ethanethioyl)-2,5-dimethylphenyl)-N-ethyl-N-methylformimidamide |
| 286 | N'-(4-(2-((2,6-difluorophenyl)amino)ethanethioyl)-2,5-dimethylphenyl)-N-ethyl-N-methylformimidamide |
| 287 | N'-(4-(2-((3,4-difluorophenyl)amino)ethanethioyl)-2,5-dimethylphenyl)-N-ethyl-N-methylformimidamide |
| 288 | N'-(2-(2-((3-chlorophenyl)thio)acetyl)-4-methylpyrimidin-5-yl)-N-ethyl-N-methylformimidamide |
| 289 | N-ethyl-N'-(2-(2-(3-fluorophenoxy)acetyl)-4-methylpyrimidin-5-yl)-N-methylformimidamide |
| 290 | N-ethyl-N'-(2-(2-((4-fluorophenyl)thio)acetyl)-4-methylpyrimidin-5-yl)-N-methylformimidamide |
| 291 | N'-(5-chloro-6-(2-((3-chlorophenyl)thio)acetyl)-2-methylpyridin-3-yl)-N-ethyl-N-methylformimidamide |
| 292 | N'-(5-chloro-2-methyl-6-(2-(3-(methylthio)phenoxy)acetyl)pyridin-3-yl)-N-ethyl-N-methylformimidamide |
| 293 | N'-(5-chloro-2-methyl-6-(2-(4-(trifluoromethoxy)phenoxy)acetyl)pyridin-3-yl)-N-ethyl-N-methylformimidamide |
| 294 | N'-(5-chloro-6-(2-((4-fluorophenyl)thio)acetyl)-2-methylpyridin-3-yl)-N-ethyl-N-methylformimidamide |
| 295 | N'-(5-chloro-2-methyl-6-(2-(phenylthio)acetyl)pyridin-3-yl)-N-ethyl-N-methylformimidamide |
| 296 | N'-(2,5-dimethyl-6-(2-(phenylthio)acetyl)pyridin-3-yl)-N-ethyl-N-methylformimidamide |
| 297 | 1-(5-chloro-2-methyl-4-((1-methylpyrrolidin-2-ylidene)amino)phenyl)-2-(3-chlorophenoxy)ethan-1-one |
| 298 | 1-(5-chloro-2-methyl-4-((1-methylpyrrolidin-2-ylidene)amino)phenyl)-2-(4-chlorophenoxy)ethan-1-one |
| 299 | 1-(5-chloro-2-methyl-4-((1-methylpyrrolidin-2-ylidene)amino)phenyl)-2-(3-fluorophenoxy)ethan-1-one |
| 300 | N'-(2,5-dimethyl-4-(2-(piperidin-1-yl)acetyl)phenyl)-N-ethyl-N-methylformimidamide |
| 301 | N-ethyl-N'-(4-(2-(isoindolin-2-yl)acetyl)-2,5-dimethylphenyl)-N-methylformimidamide |
| 302 | N'-(2,5-dimethyl-4-(2-(1-oxoisoindolin-2-yl)acetyl)phenyl)-N-ethyl-N-methylformimidamide |
| 303 | N'-(4-(3-((2,6-difluorophenyl)thio)-1,1-difluoroprop-1-en-2-yl)-2,5-dimethylphenyl)-N-ethyl-N-methylformimidamide |
| 304 | N'-(4-(3-((2-bromophenyl)thio)-1,1-difluoroprop-1-en-2-yl)-2-chloro-5-methylphenyl)-N,N-dimethylformimidamide |

* Compound names generated using Chemdraw Professional 16.0

As described herein the compounds of general formula (I) show an extremely high fungicidal activity with respect to numerous phytopathogenic fungi which attacks on important agricultural crops. Compounds of present invention were assessed for activity against one or more of the following: Biological Test Examples, in vitro test

Example 1

*Pyricularia oryzae* (Rice blast): Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature & 60% Relative Humidity for seven days and radial growth was measured. Compounds 1 2 3 4 5 6 7 8 9 10 11 12 13 14 15 16 17 18 22 27 28 29 30 31 33 34 42 47 58 59 60 63 64 67 68 69 70 71 72 73 74 76 77 78 79 80 81 82 83 84 85 86 87 88 89 90 91 92 93 94 95 96 97 98 99 100 101 102 103 105 106 107 108 109 110 111 112 113 114 115 117 118 at 300 ppm gave more than 70% control in these tests when compared to the untreated check which showed extensive disease development.

Example 2

*Rhizoctonia solani* (Rice sheath blight/Potato black scurf): Compounds were dissolved in 0.3% DMSO & then added to Potato Dextrose Agar medium just prior to dispensing it into Petri dishes. 5 ml medium with compound in the desired concentration was dispensed into 60 mm sterile Petri-plates. After solidification each plate was seeded with 5 mm size mycelial disc taken form periphery of actively growing virulent culture plate. Plates were incubated in growth chambers at 25° C. temperature & 60% Relative Humidity for seven days and radial growth was measured. Compounds 1 2 3 4 6 7 8 9 10 11 12 13 14 15 17 18 22 27 28 29 30 31 33 34 41 42 47 59 60 63 64 68 69 70 71 74 76 78 79 80 81 82 83 84 86 87 88 89 90 91 92 93 94 95 96 97 99 100 102 103 105 108 111 112 114 at 300 ppm gave more than 70% control in these tests when compared to the untreated check which showed extensive disease development.

Example 3

*Botrytis cinerea* (Gray mold): Compounds were dissolved in 0.3% DMSO & then added to Potato Dextrose Agar medium just prior to dispensing it into Petri dishes. 5 ml medium with compound in the desired concentration was dispensed into 60 mm sterile Petri-plates. After solidification each plate was seeded with 5 mm size mycelial disc taken form periphery of actively growing virulent culture plate. Plates were incubated in growth chambers at 22° C. temperature & 90% Relative Humidity for seven days and radial growth was measured. Compounds 1 2 3 4 5 6 7 8 9 11 12 13 15 18 22 27 28 29 30 59 68 70 76 79 80 83 84 86 87 88 89 90 91 93 94 95 96 99 100 102 103 107 108 112 113 114 at 300 ppm gave more than 70% in these tests when compared to the untreated check which showed extensive disease development.

Example 4

*Alternaria solani* (early blight of tomato/potato): Compounds were dissolved in 0.3% DMSO & then added to Potato Dextrose Agar medium just prior to dispensing it into Petri dishes. 5 ml medium with compound in the desired concentration was dispensed into 60 mm sterile Petri-plates. After solidification each plate was seeded with 5 mm size mycelial disc taken form periphery of actively growing virulent culture plate. Plates were incubated in growth chambers at 25° C. temperature & 60% Relative Humidity for seven days and radial growth was measured. Compounds 1 2 3; 4 5 6 7 8 9 10 11 12 13 14 15 16 17 18 22 26 27 28 29 30 31 33 34 35 40 41 42 47 56 59 60 63 64 67 68 69 70 71 72 73 74 76 77 78 79 80 81 82 83 84 85 86 87 88 89 90 91 92 93 94 95 96 97 98 99 100 101 102 103 104 105 106 108 109 111 112 113 114 115 116 117 119 at 300 ppm gave more than 70% control in these tests when compared to the untreated check which showed extensive disease development.

Example 5

*Colletotrichum capsici* (anthracnose): Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature & 60% Relative Humidity for seven days and radial growth was measured. Compounds 2 3 4 5 6 9 11 12 13 15 17 27 28 70 74 76 80 83 84 86 87 88 89 90 91 92 99 102 103 108 109 112 113 114 at 300 ppm gave more than 70% control in these tests when compared to the untreated check which showed extensive disease development.

Example 6

*Septoria lycopersici* (Leaf spot of tomato): Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature & 70% Relative Humidity for seven days and radial growth was measured. Compounds 1 2 3 4 5 6 7 9 10 11 12 13 15 16 27 28 29 30 31 33 34 42 84 88 89 92 93 94 95 96 102 103 at 300 ppm gave more than 70% control in these tests when compared to the untreated check which showed extensive disease development.

Example 7

*Fusarium culmorum* (Foot rot of cereals): Compounds were dissolved in 0.3% DMSO & then added to Potato Dextrose Agar medium just prior to dispensing it into petri dishes. 5 ml medium with compound in the desired concentration was dispensed into 60 mm sterile Petri-plates. After solidification each plate was seeded with 5 mm size mycelial disc taken form periphery of actively growing virulent culture plate. Plates were incubated in growth chambers at 25° C. temperature & 60% Relative Humidity for seven days and radial growth was measured. Compounds 2 5 11 12 13 28 29 83 84 86 88 91 102 103 109 114 at 300 ppm gave 70% control in these tests when compared to the untreated check which showed extensive disease development.

Example 8 (In Vivo on Plants): *Phakopsora pachyrhizi* Test in Soybean

Compounds were dissolved in 2% DMSO/Acetone & then mixed with water to the calibrated spray volume of 50 ml and poured into the spray bottles for further applications.

To test the preventive activity of compounds, healthy young soybean plants raised in the greenhouse were sprayed with active compound preparation at the stated application rates inside the spray cabinets using hallowcone nozzles. One day after treatment, the plants were inoculated with spore suspension containing $2.1 \times 10^6$ *Phakopsora pachyrhizi* inoculum. The inoculated plants were then kept in greenhouse chamber at 25° C. temperature & 90% Relative Humidity for disease expression.

A visual assessment of compound's performance was carried out by rating the disease severity (0-100% scale) on treated plants on 3, 7, 10 & 15 days after application. Efficacy (% control) of the compounds was calculated by comparing the disease rating in the treatment with the one of the untreated control. The sprayed plants were also assessed for compound's plant compatibility by recording symptoms like necrosis, chlorosis & stunting. Compounds 1 2 4 6 8 9 10 11 12 13 15 18 20 24 25 26 32 36 37 38 39 40 41 42 43 44 45 46 47 48 49 50 showed >90% control at 500 ppm in these tests when compared to the untreated check which showed extensive disease development.

Having described the invention with reference to certain preferred embodiments, other embodiments will become apparent to one skilled in the art from consideration of the specification. It will be apparent to those skilled in the art that many modifications, both to materials and methods, may be practiced without departing from the scope of the invention.

We claim:
1. A compound of formula (I)

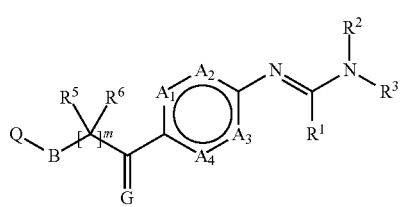

Formula (I)

wherein, $R^1$ is selected from the group consisting of hydrogen, CN, SR", OR", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl and cyclic $C_4$-$C_8$-alkynyl; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$;

$R^2$ and $R^3$ are independently selected from the group consisting of hydrogen, CN, S(O)$_n$R", OR", (C=O)—R", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl, cyclic $C_4$-$C_8$-alkynyl, $C_5$-$C_{18}$-aryl and $C_7$-$C_{19}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; or $R^1$ and $R^2$, $R^2$ and $R^3$ or $R^1$ and $R^3$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered non-aromatic ring, which for its part may be substituted by one or more X, R', OR', SR', NR'$_2$, SiR'$_3$, COOR', CN or CONR'$_2$;

each one of $R^1$, $R^2$ and $R^3$ may optionally be substituted by one or more groups selected from the group consisting of X, R', OR', SR', NR'$_2$, SiR'$_3$, COOR', CN and CONR'$_2$;

$A_1$, $A_2$, $A_3$ and $A_4$ independently represent CR$^4$ or nitrogen; with the proviso that no more than two of $A_1$, $A_2$, $A_3$ and $A_4$ are to be nitrogen simultaneously;

$R^4$ is independently selected from the group consisting of hydrogen, X, CN, NR"$_2$, NO$_2$, SCN, SF$_5$, S(O)$_n$R", SiR'$_3$, OR", (C=O)—R", CR'=NR", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl, cyclic $C_4$-$C_8$-alkynyl, $C_5$-$C_{18}$-aryl and $C_7$-$C_{19}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; or two vicinal $R^4$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a four to seven membered ring, which for its part may be substituted by one or more X, R', OR', SR', NR'$_2$, SiR'$_3$, COOR', CN or CONR'$_2$;

G and B represent O, S, NR''' or CR$^5$R$^6$;

m represents an integer 1 or 2;

$R^5$ and $R^6$ are independently selected from the group consisting of hydrogen, X, CN, NR"$_2$, SCN, S(O)$_n$R", SiR'$_3$, OR', (C=O)—R", CR'=NR", $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, cyclic $C_3$-$C_8$-alkyl, cyclic $C_4$-$C_8$-alkenyl, $C_5$-$C_{18}$-aryl and $C_7$-$C_{19}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; or $R^5$ and $R^6$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered ring, which for its part may be substituted by one or more X, R', OR', SR', NR'$_2$, SiR'$_3$, COOR', CN or CONR'$_2$; or $R^5$ and $R^6$ together represent group selected from =O, =S;

Q is selected from the group consisting of fused or non-fused $C_3$-$C_{15}$-carbocycle and $C_3$-$C_{15}$-heterocycle; which may be optionally substituted by one or more groups of $R^7$;

wherein $R^7$ is selected from the group consisting of hydrogen, X, CN, SCN, SF$_5$, OR", NO$_2$, NR"$_2$, SiR'$_3$, (C=O)—R", S(O)$_n$R", $C_1$-$C_8$-alkyl-S(O)$_n$R", $C_1$-$C_8$-alkyl-(C=O)—R", CR'=NR", S(O)$_n$$C_5$-$C_{18}$-aryl, S(O)$_n$$C_7$-$C_{19}$-aralkyl, $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, $C_1$-$C_{12}$-alkoxy, $C_1$-$C_{12}$-alkylthio, $C_1$-$C_{12}$-haloalkoxy, $C_1$-$C_{12}$-haloalkylthio, cyclic $C_3$-$C_8$-alkyl, cyclic $C_3$-$C_8$-haloalkyl, cyclic $C_4$-$C_8$-alkenyl, cyclic $C_4$-$C_8$-alkynyl, bicyclic $C_{5-12}$-alkyl, bicyclic $C_7$-$C_{12}$-alkenyl, $C_6$-$C_{15}$-aryl, $C_7$-$C_{19}$-aralkyl, $C_3$-$C_6$-heterocyclyl, $C_3$-$C_8$-heterocyclylalkyl, $C_3$-$C_6$-heterocyclyloxy and $C_3$-$C_6$-heterocyclylthio; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; or two $R^7$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered ring, which for its part may be substituted by one or more X, R', OR', SR', NR'$_2$, SiR'$_3$, COOR', CN or CONR'$_2$;

each one of $R^4$, $R^5$, $R^6$ and $R^7$ may optionally be substituted by one or more groups selected from the group consisting of X, R', R", SR', SiR'$_3$, COOR', CN and CONR'$_2$;

X represents halogen;

R' is selected from the group consisting of hydrogen, $C_1$-$C_6$-alkyl and cyclic $C_3$-$C_8$-alkyl which may be optionally substituted by one or more X;

R" is selected from the group consisting of hydrogen, CONR'$_2$, NR'$_2$, OR', $C_1$-$C_6$-alkyl, $C_1$-$C_6$-haloalkyl, cyclic $C_3$-$C_8$-alkyl which may be optionally substituted by one or more groups selected from the group consisting of X, R', OR', SR', NR'$_2$, SiR'$_3$, COOR', CN or CONR'$_2$;

and $C_6$-$C_{12}$-aryl which may be optionally substituted by one or more X, R', OR', SR', NR'$_2$, SiR'$_3$, COOR', CN or CONR'$_2$; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$;

R'" is selected from the groups consisting of hydrogen, R", OR", (C=O)—R', S(O)$_n$R", COOR', CONR'$_2$, $C_1$-$C_6$-alkyl, $C_2$-$C_6$-alkenyl, $C_2$-$C_6$-alkynyl, cyclic $C_3$-$C_8$-alkyl, $C_6$-$C_{12}$-aryl and $C_7$-$C_{12}$-aralkyl; wherein one or more carbon atoms in cyclic ring system may be replaced by heteroatoms selected from the group consisting of N, O, S and optionally including 1 to 3 ring members selected from the group consisting of C(=O), C(=S), S(O)$_m$ and SiR'$_2$; and each of the above groups may be substituted by one or more groups selected from the group consisting of X, R', OR', SR', NR'$_2$, SiR'$_3$, COOR', CN and CONR'$_2$;

n represents an integer ranging from 0 to 2;

or agronomically acceptable salts, metallic complexes, isomers/structural isomers, stereo-isomers, diastereomers, enantiomers, tautomers, polymorphs, or N-oxides thereof.

2. The compound of formula (I) according to claim 1, wherein
$R^1$ is selected from the group consisting of hydrogen, $C_1$-$C_6$-alkyl, $C_1$-$C_6$-alkoxy, $C_1$-$C_6$-alkylthio, $C_1$-$C_6$-haloalkyl and $C_3$-$C_8$-cycloalkyl;

$R^2$ and $R^3$ are independently selected from the group consisting of CN, $C_1$-$C_6$-alkyl, $C_2$-$C_6$-alkenyl, $C_2$-$C_6$-alkynyl, $C_1$-$C_6$-alkoxy, $C_1$-$C_6$-alkylthio, $C_1$-$C_6$-haloalkyl, $C_3$-$C_8$-cycloalkyl and non aromatic $C_3$-$C_8$-heterocyclyl; or $R^1$ and $R^2$, $R^2$ and $R^3$ or $R^1$ and $R^3$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a four to seven membered non-aromatic ring, which for its part may be substituted by one or more X, R', OR', SR' and CN;

$R^4$ is selected from the group consisting of hydrogen, X, CN, S(O)$_n$R", N(R'R"), (C=O)—R", CR'=NR", $C_1$-$C_6$-alkyl, $C_2$-$C_6$-alkenyl, $C_1$-$C_6$-haloalkyl, $C_1$-$C_6$-alkoxy, $C_1$-$C_6$-alkylthio, $C_1$-$C_6$-haloalkylthio, $C_3$-$C_8$-cycloalkyl, $C_3$-$C_8$-cycloalkylthio and $C_3$-$C_8$-heterocyclyl; or two vicinal $R^4$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered ring, which for its part may be substituted by one or more X, R', OR', SR', NR'$_2$, SiR'$_3$, COOR', CN or CONR'$_2$;

G and B represent O, S or NR";

$R^5$ and $R^6$ are independently selected from the group consisting of hydrogen, X, CN, S(O)$_n$R", NR'R", (C=O)—R", CR'=NR", $C_1$-$C_6$-alkyl, $C_1$-$C_6$-haloalkyl, $C_2$-$C_6$-alkenyl, $C_1$-$C_6$-alkoxy, $C_1$-$C_6$ haloalkoxy, $C_1$-$C_6$-alkylthio, $C_1$-$C_6$-haloalkylthio, $C_3$-$C_8$-cycloalkyl, $C_3$-$C_8$-cycloalkoxy, $C_3$-$C_8$-cycloalkylthio; or $R^5$ and $R^6$ together with the atom to which they are attached or together with further atoms selected from the group consisting of C, N, O, S may form a three to six membered ring, which for its part may be substituted by one or more X, R', OR', SR', NR'$_2$, SiR'$_3$, COOR', CN or CONR'$_2$;

Q is cyclopropyl, cyclobutyl, phenyl, napthalenyl, furyl, thienyl, pyrrolyl, isoxazolyl, thiazolyl, isothiazolyl, thiadiazolyl, pyrazolyl, oxazolyl, imidazolyl, oxadiazolyl, triazolyl, pyridinyl, pyridazinyl, pyrimidinyl, pyrazinyl, triazinyl, indolyl, benzimidazolyl, indazolyl, benzofuranyl, benzothiophenyl, benzothiazolyl, benzoxazolyl, quinolinyl, isoquinolinyl, iquinazolinyl, cinnonyl, indolizinyl, pyrazolo[1,5-a]pyridinyl, imidazo[1,2-a]pyridinyl, pyrrolo[1,2-a]pyrimidinyl, pyrazolo[1,5-a]pyrimidinyl, imidazo[1,2-a]pyrimidinyl, pyrrolo(1,2-a]pyrazinyl, pyrazolo[1,5-a]pyrazinyl, imidazo[1,2-a]pyrazinyl; each Q is substituted with one or more $R^7$;

$R^7$ is selected hydrogen, X, CN, SCN, SF$_5$, R", OR", NO$_2$, NR"$_2$, SiR'$_3$, OS(O)$_n$R", OSiR'3, NR'S(O)$_n$R", (C=O)—R", S(O)$_n$R", $C_{1-8}$-alkyl-S(O)$_n$R", $C_1$-$C_6$-alkyl-(C=O)—R", CR'=NR", $C_1$-$C_{12}$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-alkoxy, $C_1$-$C_6$-alkylthio, $C_1$-$C_6$-haloalkoxy, $C_1$-$C_6$-haloalkylthio, $C_3$-$C_8$-cycloalkyl, $C_{4-8}$-cycloalkenyl, $C_3$-$C_8$-cycloalkyloxy and $C_3$-$C_8$-cycloalkylthio; or two $R^7$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a four to ten membered ring, which for its part may be substituted by one or more X, R', OR', SR', NR'$_2$, SiR'$_3$, COOR', CN or CONR'$_2$;

$R^1$, $R^2$, $R^3$ $R^4$, $R^5$, $R^6$ and $R^7$ may further optionally substituted by one or more groups selected from the group consisting of X, R", OR', SR', NR'$_2$, SiR'$_3$, COOR', CN and CONR'$_2$;

or agronomically acceptable salts, isomers/structural isomers, stereo-isomers, diastereoisomers, enantiomers, tautomers, or N-oxides thereof.

3. The compound of formula (I) according to claim 1, wherein
$R^1$ is selected from the group consisting of hydrogen, $C_1$-$C_6$-alkyl and $C_3$-$C_8$-cycloalkyl;

$R^2$ and $R^3$ are independently selected from the group consisting of $C_1$-$C_6$-alkyl, $C_1$-$C_6$-haloalkyl and $C_3$-$C_8$-cycloalkyl;

$R^4$ is selected from the group consisting of hydrogen X, CN, S(O)$_n$R', OR", N(R'R"), $C_1$-$C_6$-alkyl, $C_1$-$C_6$-haloalkyl and $C_3$-$C_8$-cycloalkyl;

$R^5$ and $R^6$ are independently selected from the group consisting of hydrogen, X, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl; or $R^5$ and $R^6$ together with the atom to which they are attached or together with further atoms selected from the group consisting of C, N, O, S may form a three to four membered ring, which for its part may be substituted by one or more X, R', OR', SR', NR'$_2$, SiR'$_3$, COOR', CN or CONR'$_2$;

Q is cyclopropyl, phenyl, napthalenyl, thienyl, thiazole, thiadiazole, isothiazolyl, pyrazolyl, pyridinyl, pyridazinyl, pyrimidinyl, pyrazinyl and quinolinyl; each Q is substituted with one or more $R^7$;

$R^7$ is selected from the group consisting of hydrogen, X, CN, SCN, SF$_5$, R", OR", NO$_2$, NR"$_2$, SiR'$_3$, (C=O)—R", S(O)$_n$R", OS(O)$_n$R", NR'S(O)$_n$R", OSiR'3, $C_1$-s-alkyl-S(O)$_n$R", $C_1$-$C_6$-alkyl-(C=O)—R", CR'=NR", SC$_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-alkoxy, $C_1$-$C_6$-alkylthio, $C_1$-$C_6$-holoalkoxy, $C_1$-$C_6$-haloalkylthio, $C_3$-$C_8$-cycloalkyl, $C_{4-8}$-cycloalkenyl, $C_3$-$C_8$-cycloalkyloxy and $C_3$-$C_8$-cycloalkylthio; or two $R^7$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a four to ten membered ring, which for its part may be substituted by one or more X, R', OR', SR', NR'$_2$, SiR'$_3$, COOR', CN, and CONR'$_2$;

wherein $R^1$ to $R^7$ may further optionally substituted by one or more groups selected from the group consisting of X, R", OR', SR', NR'$_2$, SiR'$_3$, COOR', CN and CONR'$_2$;

or agronomically acceptable salts, metallic complexes, isomers/structural isomers, stereo-isomers, diastereomers, enantiomers, tautomers, polymorphs, or N-oxides thereof.

4. The compound of formula (I) according to claim 1, wherein said compound of formula (I) is selected from N'-(2,5-dimethyl-4-(2-(phenylthio)acetyl)phenyl)-N-ethyl-N-methylformimidamide; N'-(2,5-dimethyl-4-(2-phenoxyacetyl)phenyl)-N-ethyl-N-methylformimidamide; N'-(4-(2-(3-bromophenoxy)acetyl)-2,5-dimethylphenyl)-N-ethyl-N-methylformimidamide; N-ethyl-N'-(4-(2-((3-fluorophenyl)thio)acetyl)-2,5-dimethylphenyl)-N-methylformimidamide; N'-(2,5-dimethyl-4-(2-(m-tolylthio)acetyl)phenyl)-N-ethyl-N-methylformimidamide; N'-(4-(2-((3-bromophenyl)thio)acetyl)-2,5-dimethylphenyl)-N-ethyl-N-methylformimidamide; N-ethyl-N'-(4-(2-((4-methoxyphenyl)thio)acetyl)-2,5-dimethylphenyl)-N-methylformimidamide; N'-(4-(2-((3,4-dichlorophenyl)thio)acetyl)-2,5-dimethylphenyl)-N-ethyl-N-methylformimidamide; N-ethyl-N'-(4-(2-(3-fluorophenoxy)acetyl)-2,5-dimethylphenyl)-N-methylformimidamide; N-ethyl-N'-(4-(2-(4-methoxyphenoxy)acetyl)-2,5-dimethylphenyl)-N-methylformimidamide; N'-(4-(2-((3,4-dimethylphenyl)thio)acetyl)-2,5-dimethylphenyl)-N-ethyl-N-methylformimidamide; N'-(2,5-dimethyl-4-(2-(m-tolyloxy)acetyl)phenyl)-N-ethyl-N-methylformimidamide; N'-(4-(2-(3-chlorophenoxy)acetyl)-2,5-dimethylphenyl)-N-ethyl-N-methylformimidamide; N'-(2,5-dimethyl-4-(2-(4-(trifluoromethoxy)phenoxy)acetyl)phenyl)-N-ethyl-N-methylformimidamide; N'-(2,5-dimethyl-4-(2-(p-tolyloxy)acetyl)phenyl)-N-ethyl-N-methylformimidamide; N'-(4-(2-(4-chlorophenoxy)acetyl)-2,5-dimethylphenyl)-N-ethyl-N-methylformimidamide; N'-(2,5-dimethyl-4-(2-(3-(methylthio)phenoxy)acetyl)phenyl)-N-ethyl-N-methylformimidamide; N'-(4-(2-((3-chloro-5-(trifluoromethyl)pyridin-2-yl)thio)acetyl)-2,5-dimethylphenyl)-N-ethyl-N-methylformimidamide; N'-(2-chloro-5-methyl-4-(2-phenoxyacetyl)phenyl)-N-ethyl-N-methylformimidamide; N'-(2-chloro-4-(2-(3-chlorophenoxy)acetyl)-5-methylphenyl)-N-ethyl-N-methylformimidamide; N'-(2-chloro-4-(2-(4-chlorophenoxy)acetyl)-5-methylphenyl)-N-ethyl-N-methylformimidamide; N'-(4-(2-((4-bromophenyl)thio)acetyl)-2,5-dimethylphenyl)-N-ethyl-N-methylformimidamide; N'-(4-(2-(3-bromophenoxy)acetyl)-2-chloro-5-methylphenyl)-N-ethyl-N-methylformimidamide; N'-(2-chloro-4-(2-(3-fluorophenoxy)acetyl)-5-methylphenyl)-N-ethyl-N-methylformimidamide; N'-(2-chloro-5-methyl-4-(2-(p-tolyloxy)acetyl)phenyl)-N-ethyl-N-methylformimidamide; N'-(2-chloro-5-methyl-4-(2-(m-tolyloxy)acetyl)phenyl)-N-ethyl-N-methylformimidamide; N-ethyl-N'-(4-(2-((3-methoxyphenyl)thio)acetyl)-2,5-dimethylphenyl)-N-methylformimidamide; N-ethyl-N'-(4-(2-((4-fluorophenyl)thio)acetyl)-2,5-dimethylphenyl)-N-methylformimidamide; N'-(4-(2-((4-chlorophenyl)thio)acetyl)-2,5-dimethylphenyl)-N-ethyl-N-methylformimidamide; N'-(4-(2-((2-bromophenyl)thio)acetyl)-2,5-dimethylphenyl)-N-ethyl-N-methylformimidamide; N'-(4-(2-(2-bromophenoxy)acetyl)-2-chloro-5-methylphenyl)-N-ethyl-N-methylformimidamide; N-ethyl-N'-(4-(2-(2-fluorophenoxy)acetyl)-2,5-dimethylphenyl)-N-methylformimidamide; N-ethyl-N'-(4-(2-(4-fluorophenoxy)acetyl)-2,5-dimethylphenyl)-N-methylformimidamide; N'-(4-(2-(2-bromophenoxy)acetyl)-2,5-dimethylphenyl)-N-ethyl-N-methylformimidamide; N'-(2-chloro-5-methyl-4-(2-(m-tolylthio)acetyl)phenyl)-N-ethyl-N-methylformimidamide; N'-(4-(2-((3-bromophenyl)thio)acetyl)-2-chloro-5-methylphenyl)-N-ethyl-N-methylformimidamide; N'-(2-chloro-4-(2-((3-fluorophenyl)thio)acetyl)-5-methylphenyl)-N-ethyl-N-methylformimidamide; N'-(2-chloro-4-(2-((4-chlorophenyl)thio)acetyl)-5-methylphenyl)-N-ethyl-N-methylformimidamide; N'-(4-(2-((2-bromophenyl)thio)acetyl)-2-chloro-5-methylphenyl)-N-ethyl-N-methylformimidamide; 2-(3-chlorophenoxy)-1-(2,5-dimethyl-4-((morpholinomethylene)amino)phenyl)ethan-1-one; 2-(3-chlorophenoxy)-1-(2,5-dimethyl-4-((piperidin-1-ylmethylene)amino)phenyl)ethan-1-one; N'-(4-(2-(3-chlorophenoxy)acetyl)-2,5-dimethylphenyl)-N-isopropyl-N-methylformimidamide; N-allyl-N'-(4-(2-(3-chlorophenoxy)acetyl)-2,5-dimethylphenyl)-N-methylformimidamide; N'-(2-chloro-4-(2-(2-fluorophenoxy)acetyl)-5-methylphenyl)-N-ethyl-N-methylformimidamide; N'-(2-chloro-4-(2-(4-fluorophenoxy)acetyl)-5-methylphenyl)-N-ethyl-N-methylformimidamide; N'-(4-(2-(3-chlorophenoxy)acetyl)-2,5-dimethylphenyl)-N-cyanoformimidamide; N'-(4-(2-((3,4-dimethylphenyl)thio)acetyl)-2,5-dimethylphenyl)-N-isopropyl-N-methylformimidamide; N-ally-N'-(4-(2-((3,4-dimethylphenyl)thio)acetyl)-2,5-dimethylphenyl)-N-methylformimidamide; 1-(2,5-dimethyl-4-((morpholinomethylene)amino)phenyl)-2-((3,4-dimethylphenyl)thio)ethan-1-oneN'-(2-chloro-4-(2-((3,4-dichlorophenyl)thio)acetyl)-5-methylphenyl)-N-ethyl-N-methylformimidamide; N'-(2-chloro-4-(2-((3,5-dichlorophenyl)thio)acetyl)-5-methylphenyl)-N-ethyl-N-methylformimidamide; N'-(2-chloro-5-methyl-4-(2-(3-(methylthio)phenoxy)acetyl)phenyl)-N-ethyl-N-methylformimidamide; N'-(2-chloro-5-methyl-4-(2-(4-(trifluoromethoxy)phenoxy)acetyl)phenyl)-N-ethyl-N-methylformimidamide; N'-(2-chloro-4-(2-((4-fluorophenyl)thio)acetyl)-5-methylphenyl)-N-ethyl-N-methylformimidamide; N'-(4-(2-((4-bromophenyl)thio)acetyl)-2-chloro-5-methylphenyl)-N-ethyl-N-methylformimidamide; N'-(2-chloro-4-(2-((3-methoxyphenyl)thio)acetyl)-5-methylphenyl)-N- ethyl-N-methylformimidamide; N'-(2-chloro-5-methyl-4-(2-(phenylthio)acetyl)phenyl)-N-ethyl-N-methylformimidamide; N'-(2-chloro-4-(2-((2-fluorophenyl)thio)acetyl)-5-methylphenyl)-N-ethyl-N-methylformimidamide; N-ethyl-N'-(4-(2-((2-fluorophenyl)thio)acetyl)-2,5-dimethylphenyl)-N-methylformimidamide; N'-(2,5-dimethyl-4-(2-((3-(trifluoromethyl)phenyl)thio)acetyl)phenyl)-N-ethyl-N-methylformimidamide; 2-(3-chlorophenoxy)-1-(2,5-dimethyl-4-((thiomorpholinomethylene)amino)phenyl)ethan-1-one; 1-(2,5-dimethyl-4-((thiomorpholinomethylene)amino)phenyl)-2-((3,4-dimethylphenyl)thio)ethan-1-one; N'-(4-(2-((3-chlorophenyl)thio)acetyl)-2,5-dimethylphenyl)-N-ethyl-N-methylformimidamide; N'-(2,5-dimethyl-4-(2-((4-(methylthio)phenyl)thio)acetyl)phenyl)-N-ethyl-N-methylformimidamide; N'-(2-chloro-4-(2-((3-chlorophenyl)thio)acetyl)-5-methylphenyl)-N-ethyl-N-methylformimidamide; N'-(2-chloro-5-methyl-4-(2-((3-(trifluoromethyl)phenyl)thio)acetyl)phenyl)-N-ethyl-N-methylformimidamide; N'-(2,5-dimethyl-4-(2-(3-((perfluoroethyl)thio)phenoxy)acetyl)phenyl)-N-ethyl-N-methylformimidamide; N'-(2,5-dimethyl-4-(2-(3-((trifluoromethyl)thio)phenoxy)acetyl)phenyl)-N-ethyl-N-methylformimidamide; N'-(4-(2-(3-(dimethylamino)phenoxy)acetyl)-2,5-dimethylphenyl)-N-ethyl-N-methylformimidamide; N'-(2,5-dimethyl-4-(2-methyl-2-(m-tolyloxy)propanoyl)phenyl)-N-ethyl-N-methylformimidamide; N'-(2,5-dimethyl-4-(2-(o-tolyloxy)acetyl)phenyl)-N-ethyl-N-methylformimidamide; N'-(2,5-dimethyl-4-(2-(3-(trifluoromethyl)phenoxy)acetyl)phenyl)-N-ethyl-N-methylformimidamide; N'-(4-(2-(3,4-dichlorophenoxy)acetyl)-2,5-dimethylphenyl)-N-ethyl-N-methylformimidamide; N'-(4-(2-(2,6-dimethylphenoxy)acetyl)-2,5-dimethylphenyl)-N-ethyl-N-methylformimidamide; N'-(4-(2-(2-(tert-butyl)phenoxy)acetyl)-2,5-dimethylphenyl)-N-ethyl-N-methylformimidamide; N'-(4-(2-(3,4-dimethylphenoxy)acetyl)-2,5-dimethylphenyl)-N-ethyl-N-methylformimidamide; N'-(2,5-dimethyl-4-(2-(m-tolyloxy)propanoyl)phenyl)-N-ethyl-N-methylformimidamide; N'-(2,5-dimethyl-4-(2-(3-((3,4,4-trifluorobut-3-en-1-yl)thio)phenoxy)acetyl)phenyl)-N-ethyl-N-methylformimidamide; N'-(2,5-dimethyl-4-(2-(4-((trifluoromethyl)thio)phenoxy)acetyl)phenyl)-N-ethyl-N-methylformimidamide; N'-(4-(2-(3-bromo-4-methylphenoxy)acetyl)-2,5-dimethylphenyl)-N-ethyl-N-methylformimidamide; N'-(4-(2-(2-bromo-4-methylphenoxy)acetyl)-2,5-dimethylphenyl)-N-ethyl-N-methylformimidamide; N'-(4-(2-((2,6-dimethylphenyl)thio)acetyl)-2,5-dimethylphenyl)-N-ethyl-N-methylformimidamide; N'-(2,5-dimethyl-4-(2-methyl-2-(m-tolylthio)propanoyl)phenyl)-N-ethyl-N-methylformimidamide; N'-(4-(N-(4-chlorophenyl)-N-methylglycyl)-2,5-dimethylphenyl)-N-ethyl-N-methylformimidamide; N'-(2,5-dimethyl-4-(N-methyl-N-phenylglycyl)phenyl)-N-ethyl-N-methylformimidamide; N'-(4-(2-(2,6-dichlorophenoxy)acetyl)-2,5-dimethylphenyl)-N-ethyl-N-methylformimidamide; N'-(4-(2-(2,6-dibromophenoxy)acetyl)-2,5-dimethylphenyl)-N-ethyl-N-methylformimidamide; N'-(4-(2-(2-bromo-6-methylphenoxy)acetyl)-2,5-dimethylphenyl)-N-ethyl-N-methylformimidamide; N'-(4-(2-(2-bromo-4,6-dimethylphenoxy)acetyl)-2,5-dimethylphenyl)-N-ethyl-N-methylformimidamide; N'-(4-(2-(2-bromo-5-methylphenoxy)acetyl)-2,5-dimethylphenyl)-N-ethyl-N-methylformimidamide; N'-(4-(2-(2-chloro-6-methylphenoxy)acetyl)-2,5-dimethylphenyl)-N-ethyl-N-methylformimidamide; N'-(2,5-dimethyl-4-(N-methyl-N-(p-tolyl)glycyl)phenyl)-N-ethyl-N-methylformimidamide; N'-(4-(2-(2-chloro-4-methylphenoxy)acetyl)-2,5-dimethylphenyl)-N-ethyl-N-methylformimidamide; N'-(4-(2-(2,4-dichlorophenoxy)acetyl)-2,5-dimethylphenyl)-N-ethyl-N-methylformimidamide; N'-(4-(2-(2,5-dimethylphenoxy)acetyl)-2,5-dimethylphenyl)-N-ethyl-N-methylformimidamide; N'-(4-(2-(5-chloro-2-methylphenoxy)acetyl)-2,5-dimethylphenyl)-N-ethyl-N-methylformimidamide; N'-(4-(2-(3,5-dichlorophenoxy)acetyl)-2,5-dimethylphenyl)-N-ethyl-N-methylformimidamide; N'-(4-(2-(4-chloro-3-(trifluoromethyl)phenoxy)acetyl)-2,5-dimethylphenyl)-N-ethyl-N-methylformimidamide; N'-(4-(2-(2,3-dimethylphenoxy)acetyl)-2,5-dimethylphenyl)-N-ethyl-N-methylformimidamide; N'-(4-(2-((2-chloro-6-methylphenyl)thio)acetyl)-2,5-dimethylphenyl)-N-ethyl-N-methylformimidamide; N'-(4-(2-((3,5-dichlorophenyl)thio)acetyl)-2,5-dimethylphenyl)-N-ethyl-N-methylformimidamide; N'-(4-(2-((2,4-difluorophenyl)thio)acetyl)-2,5-dimethylphenyl)-N-ethyl-N-methylformimidamide; N'-(4-(2-((2,6-difluorophenyl)thio)acetyl)-2,5-dimethylphenyl)-N-ethyl-N-methylformimidamide; N'-(4-(2-((2-bromophenyl)thio)acetyl)-2-chloro-5-methylphenyl)-N,N-dimethylformimidamide; N'-(2,5-dimethyl-4-(2-(3-(methylthio)phenoxy)acetyl)phenyl)-N,N-dimethylformimidamide; N'-(4-(2-((3-fluorophenyl)thio)acetyl)-2,5-dimethylphenyl)-N,N-dimethylformimidamide; N'-(4-(2-((2,6-dimethylphenyl)thio)acetyl)-2,5-dimethylphenyl)-N,N-dimethylformimidamide; N'-(4-(2-(2-chlorophenoxy)acetyl)-2,5-dimethylphenyl)-N-ethyl-N-methylformimidamide; N'-(4-(2-(2-chlorophenoxy)acetyl)-2,5-dimethylphenyl)-N,N-dimethylformimidamide; N-ethyl-N'-(4-(2-(2-methoxyphenoxy)acetyl)-2,5-dimethylphenyl)-N-methylformimidamide; N-ethyl-N'-(4-(2-(3-(ethylthio)phenoxy)acetyl)-2,5-dimethylphenyl)-N-methylformimidamide; N'-(2-bromo-4-(2-((3-fluorophenyl)thio)acetyl)-3,6-dimethylphenyl)-N-ethyl-N-methylformimidamide; N'-(2,5-dimethyl-4-(2-(3-(trifluoromethoxy)phenoxy)acetyl)phenyl)-N-ethyl-N-methylformimidamide; N'-(4-(2-(4H-1,2,4-triazol-4-yl)acetyl)-2,5-dimethylphenyl)-N-ethyl-N-methylformimidamide; N'-(2,5-dimethyl-4-(2-(3-(trifluoromethoxy)phenoxy)acetyl)phenyl)-N,N-dimethylformimidamide; N'-(4-(2-(benzo[d]thiazol-2-ylthio)acetyl)-2,5-dimethylphenyl)-N,N-dimethylformimidamide; N'-(4-(2-(4H-1,2,4-triazol-4-yl)acetyl)-2,5-dimethylphenyl)-N,N-dimethylformimidamide; N'-(2,5-dimethyl-4-(2-(4-(trifluoromethyl)phenoxy)acetyl)phenyl)-N,N-dimethylformimidamide; N'-(2-chloro-4-(2-(2,5-dimethylphenoxy)acetyl)-5-methylphenyl)-N-ethyl-N-methylformimidamide; N'-(4-(2-(2-bromo-4-methylphenoxy)acetyl)-2-chloro-5-methylphenyl)-N-ethyl-N-methylformimidamide; N'-(2-chloro-4-(2-(5-chloro-2-methylphenoxy)acetyl)-5-methylphenyl)-N-ethyl-N-methylformimidamide; N'-(4-(2-(2-bromo-4-methoxyphenoxy)acetyl)-2-chloro-5-methylphenyl)-N-ethyl-N-methylformimidamide; N-ethyl-N'-(4-(3-(4-fluorophenyl)propanoyl)-2,5-dimethylphenyl)-N-methylformimidamide; N'-(4-((2-chlorophenyl)glycyl)-2,5-dimethylphenyl)-N-ethyl-N-methylformimidamide; N-ethyl-N'-(2-fluoro-5-methyl-4-(3-(o-tolyl)propanoyl)phenyl)-N-methylformimidamide; N'-(4-((4-chlorophenyl)glycyl)-2,5-dimethylphenyl)-N-ethyl-N-methylformimidamide; N'-(5-chloro-4-(3-(2-fluorophenyl)propanoyl)-2-methylphenyl)-N-ethyl-N-methylformimidamide; N'-(4-(2-(1H-benzo[d]imidazol-1-yl)acetyl)-2,5-dimethylphenyl)-N-ethyl-N-methylformimidamide; N'-(2-chloro-4-(3-(3-fluorophenyl)propanoyl)-5-methylphenyl)-N-ethyl-N-methylformimidamide; N'-(4-(2-(1H-indol-1-yl)acetyl)-2,5-dimethylphenyl)-N-ethyl-N-methylformimidamide; N-ethyl-N'-(5-fluoro-4-(2-((2-fluorophenyl)thio)-2-methylphenyl)-N-methylformimidamide; N'-(4-(2-(1H-imidazo[4,5-b]pyridin-1-yl)acetyl)-2,5-dimethylphenyl)-N-ethyl-N-methylformimidamide; N-ethyl-N'-(5-fluoro-4-(2-(3-fluorophenoxy)acetyl)-2-methylphenyl)-N-methylformimidamide; N'-(2,5-dimethyl- 4-(2-(3-methyl-1H-pyrrol-1-yl)acetyl)phenyl)-N-ethyl-N-methylformimidamide; N-ethyl-N'-(5-fluoro-4-(2-((4-fluorophenyl)thio)acetyl)-2-methylphenyl)-N-methylformimidamide; N'-(4-(2-(2H-isoindol-2-yl)acetyl)-2,5-dimethylphenyl)-N-ethyl-N-methylformimidamide; N-ethyl-N'-(5-fluoro-4-(2-((2-fluoro-6-methylphenyl)thio)acetyl)-2-methylphenyl)-N-methylformimidamide; N'-(2,5-dimethyl-4-(2-(2-oxopyridin-1(2H)-yl)acetyl)phenyl)-N-ethyl-N-methylformimidamide; N-ethyl-N'-(5-fluoro-4-(N-(2-fluorophenyl)-N-methylglycyl)-2-methylphenyl)-N-methylformimidamide; N'-(4-(2-(1H-pyrazol-1-yl)acetyl)-2,5-dimethylphenyl)-N-ethyl-N-methylformimidamide; N-ethyl-N'-(5-fluoro-4-(N-(3-fluorophenyl)-N-methylglycyl)-2-methylphenyl)-N-methylformimidamide; N'-(2,5-dimethyl-4-(2-(4,5,6,7-tetrahydro-1H-indazol-1-yl)acetyl)phenyl)-N-ethyl-N-methylformimidamide; N-ethyl-N'-(5-fluoro-4-(N-(4-fluorophenyl)-N-methylglycyl)-2-methylphenyl)-N-methylformimidamide; N'-(2,5-dimethyl-4-(2-(4,5,6,7-tetrahydro-1H-indol-1-yl)acetyl)phenyl)-N-ethyl-N-methylformimidamide; N-ethyl-N'-(5-fluoro-4-(N-(2-fluoro-6-methylphenyl)-N-methylglycyl)-2-methylphenyl)-N-methylformimidamide; N'-(2,5-dimethyl-4-(2-(4,5,6,7-tetrahydro-2H-isoindol-2-yl)acetyl)phenyl)-N-ethyl-N-methylformimidamide; N-ethyl-N'-(2-fluoro-4-(N-(2-fluorophenyl)-N-methylglycyl)-5-methylphenyl)-N-methylform- imidamide; N'-(4-(2-(benzo[d]thiazol-3(2H)-yl)acetyl)-2,5-dimethylphenyl)-N-ethyl-N-methylformimidamide; N-ethyl-N'-(2-fluoro-4-(N-(3-fluorophenyl)-N-methylglycyl)-5-methylphenyl)-N-methylformimidamide; N-ethyl-N'-(4-(2-(3-fluorophenoxy)-1-(methylimino)ethyl)-2,5-dimethylphenyl)-N-methylformimidamide; N-ethyl-N'-(2-fluoro-4-(N-(4-fluorophenyl)-N-methylglycyl)-5-methylphenyl)-N-methylformimidamide; N-ethyl-N'-(4-(2-(4-methoxyphenoxy)-1-(methylimino)ethyl)-2,5-dimethylphenyl)-N-methylformimidamide; N-ethyl-N'-(2-fluoro-4-(N-(2-fluoro-6-methylphenyl)-N-methylglycyl)-5-methylphenyl)-N-methylformimidamide; N'-(4-(2-((3,4-dimethylphenyl)thio)-1-(methylimino)ethyl)-2,5-dimethylphenyl)-N-ethyl-N-methylformimidamide; N'-(5-chloro-4-(N-(2-fluorophenyl)-N-methylglycyl)-2-methylphenyl)-N-ethyl-N-methylformimidamide; N'-(2,5-dimethyl-4-(1-(methylimino)-2-(m-tolyloxy)ethyl)phenyl)-N-ethyl-N-methylformimidamide; N'-(5-chloro-4-(N-(3-fluorophenyl)-N-methylglycyl)-2-methylphenyl)-N-ethyl-N-methylformimidamide; N'-(4-(2-(3-chlorophenoxy)-1-(methylimino)ethyl)-2,5-dimethylphenyl)-N-ethyl-N-methylformimidamide; N'-(5-chloro-4-(N-(4-fluorophenyl)-N-methylglycyl)-2-methylphenyl)-N-ethyl-N-methylformimidamide; N'-(2,5-dimethyl-4-(1-(methylimino)-2-(4-(trifluoromethoxy)phenoxy)ethyl)phenyl)-N-ethyl-N-methylformimidamide; N'-(5-chloro-4-(N-(2-fluoro-6-methylphenyl)-N-methylglycyl)-2-methylphenyl)-N-ethyl-N-methylformimidamide; N'-(2,5-dimethyl-4-(1-(methylimino)-2-(p-tolyloxy)ethyl)phenyl)-N-ethyl-N-methylformimidamide; N'-(2-Fluoro-4-((2-fluorophenyl)glycyl)-5-methylphenyl)-N-ethyl-N-methylformimidamide; N'-(4-(2-(4-chlorophenoxy)-1-(methylimino)ethyl)-2,5-dimethylphenyl)-N-ethyl-N-methylformimidamide; N'-(2-Fluoro-4-((3-fluorophenyl)glycyl)-5-methylphenyl)-N-ethyl-N-methylformimidamide; N'-(2,5-dimethyl-4-(1-(methylimino)-2-(3-(methylthio)phenoxy)ethyl)phenyl)-N-ethyl-N-methylformimidamide; N'-(2-Fluoro-4-((4-fluorophenyl)glycyl)-5-methylphenyl)-N-ethyl-N-methylformimidamide; N'-(4-(2-((3-chloro-5-(trifluoromethyl)pyridin-2-yl)thio)-1-(methylimino)ethyl)-2,5-dimethylphenyl)-N-ethyl-N-methylformimidamide; N'-(2-Fluoro-4-((2-fluoro-6-methylphenyl)glycyl)-5-methylphenyl)-N-ethyl-N-methylformimidamide; N'-(2-chloro-5-methyl-4-(1-(methylimino)-2-phenoxyethyl)phenyl)-N-ethyl-N-methylformimidamide; N'-(2-chloro-4-((2-fluorophenyl)glycyl)-5-methylphenyl)-N-ethyl-N-methylformimidamide; N'-(2-chloro-4-(2-(3-chlorophenoxy)-1-(methylimino)ethyl)-5-methylphenyl)-N-ethyl-N-methylformimidamide; N'-(2-chloro-4-((3-fluorophenyl)glycyl)-5-methylphenyl)-N-ethyl-N-methylformimidamide; N'-(2-chloro-4-(2-(4-chlorophenoxy)-1-(methylimino)ethyl)-5-methylphenyl)-N-ethyl-N-methylformimidamide; N'-(2-chloro-4-((4-fluorophenyl)glycyl)-5-methylphenyl)-N-ethyl-N-methylformimidamide; N'-(4-(2-((4-bromophenyl)thio)-1-(methylimino)ethyl)-2,5-dimethylphenyl)-N-ethyl-N-methylformimidamide; N'-(2-chloro-4-((2-fluoro-6-methylphenyl)glycyl)-5-methylphenyl)-N-ethyl-N-methylformimidamide; N'-(4-(2-(3-bromophenoxy)-1-(methylimino)ethyl)-2-chloro-5-methylphenyl)-N-ethyl-N-methylformimidamide; N'-(2-chloro-4-(N-(2-fluorophenyl)-N-methylglycyl)-5-methylphenyl)-N-ethyl-N-methylformimidamide; N'-(2-chloro-4-(2-(3-fluorophenoxy)-1-(methylimino)ethyl)-5-methylphenyl)-N-ethyl-N-methylformimidamide; N'-(2-chloro-4-(N-(3-fluorophenyl)-N-methylglycyl)-5-methylphenyl)-N-ethyl-N-methylformimidamide; N'-(2-chloro-5-methyl-4-(1-(methylimino)-2-(p-tolyloxy)ethyl)phenyl)-N-ethyl-N-methylformimidamide; N'-(2-chloro-4-(N-(4-fluorophenyl)-N-methylglycyl)-5-methylphenyl)-N-ethyl-N-methylformimidamide; N'-(2-chloro-5-methyl-4-(1-(methylimino)-2-(m-tolyloxy)ethyl)phenyl)-N-ethyl-N-methylformimidamide; N'-(2-chloro-4-(N-(2-fluoro-6-methylphenyl)-N-methylglycyl)-5-methylphenyl)-N-ethyl-N-methylformimidamide; N-ethyl-N'-(4-(2-((3-methoxyphenyl)thio)-1-(methylimino)ethyl)-2,5-dimethylphenyl)-N-methylformimidamide; N-ethyl-N'-(4-(N-(2-fluorophenyl)-N-methylglycyl)-2,5-dimethylphenyl)-N-methylformimidamide; N-ethyl-N'-(4-(2-((4-fluorophenyl)thio)-1-(methylimino)ethyl)-2,5-dimethylphenyl)-N-methylformimidamide; N-ethyl-N'-(4-(N-(3-fluorophenyl)-N-methylglycyl)-2,5-dimethylphenyl)-N-methylformimidamide; N'-(4-(2-((4-chlorophenyl)thio)-1-(methylimino)ethyl)-2,5-dimethylphenyl)-N-ethyl-N-methylformimidamide; N-ethyl-N'-(4-(N-(4-fluorophenyl)-N-methylglycyl)-2,5-dimethylphenyl)-N-methylformimidamide; N'-(4-(2-((2-bromophenyl)thio)-1-(methylimino)ethyl)-2,5-dimethylphenyl)-N-ethyl-N-methylformimidamide; N-ethyl-N'-(4-(N-(2-fluoro-6-methylphenyl)-N-methylglycyl)-2,5-dimethylphenyl)-N-methylformimidamide; N'-(4-(2-(2-bromophenoxy)-1-(methylimino)ethyl)-2-chloro-5-methylphenyl)-N-ethyl-N-methylformimidamide; N-ethyl-N'-(4-(N-(5-fluoro-2-methylphenyl)-N-methylglycyl)-2,5-dimethylphenyl)-N-methylformimidamide; N-ethyl-N'-(4-(2-(2-fluorophenoxy)-1-(methylimino)ethyl)-2,5-dimethylphenyl)-N-methylformimidamide; N-ethyl-N'-(4-(N-(4-fluoro-2-methylphenyl)-N-methylglycyl)-2,5-dimethylphenyl)-N-methylformimidamide; N-ethyl-N'-(4-(2-(4-fluorophenoxy)-1-(methylimino)ethyl)-2,5-dimethylphenyl)-N-methylformimidamide; N-ethyl-N'-(4-(N-(3-fluoro-2-methylphenyl)-N-methylglycyl)-2,5-dimethylphenyl)-N-methylformimidamide; N'-(4-(2-(2-bromophenoxy)-1-(methylimino)ethyl)-2,5-dimethylphenyl)-N-ethyl-N-methylformimidamide; N'-(4-(N-(2-chloro-6-fluorophenyl)-N-methylglycyl)-2,5-dimethylphenyl)-N-ethyl-N-methylformimidamide; N'-(2-chloro-5-methyl-4-(1-(methylimino)-2-(m-tolylthio)ethyl)phenyl)-N-ethyl-N-methylformimidamide; N-ethyl-N'-(4-(N-(3-fluoro-4-methylphenyl)-N-methylglycyl)-2,5-dimethylphenyl)-N-methylformimidamide; N'-(4-(2-((3-bromophenyl)thio)-1-(methylimino)ethyl)-2-chloro-5-methylphenyl)-N-ethyl-N-methylformimidamide; N'-(4-(N-(4-chloro-3-fluorophenyl)-N-methylglycyl)-2,5-dimethylphenyl)-N- ethyl-N-methylformimidamide; N'-(2-chloro-4-((Z)-2-((3-fluorophenyl)thio)-1-(methylimino)ethyl)-5-methylphenyl)-N-ethyl-N-methylformimidamide; N'-(4-(N-(2-chloro-5-fluorophenyl)-N-methylglycyl)-2,5-dimethylphenyl)-N-ethyl-N-methylformimidamide; N'-(2-chloro-4-((Z)-2-((4-chlorophenyl)thio)-1-(methylimino)ethyl)-5-methylphenyl)-N-ethyl-N-methylformimidamide; N'-(4-(N-(2-chloro-4-fluorophenyl)-N-methylglycyl)-2,5-dimethylphenyl)-N-ethyl-N-methylformimidamide; N'-(4-((Z)-2-((2-bromophenyl)thio)-1-(methylimino)ethyl)-2-chloro-5-methylphenyl)-N-ethyl-N-methylformimidamide; N'-(4-(N-(2-chloro-3-fluorophenyl)-N-methylglycyl)-2,5-dimethylphenyl)-N-ethyl-N-methylformimidamide; N'-(2,5-dimethyl-4-(1-(m-tolyloxy)cyclopropane-1-carbonyl)phenyl)-N-ethyl-N-methylformimidamide; N'-(4-(N-(4-bromo-3-fluorophenyl)-N-methylglycyl)-2,5-dimethylphenyl)-N-ethyl-N-methylformimidamide; N'-(2,5-dimethyl-4-(1-(o-tolyloxy)cyclopropane-1-carbonyl)phenyl)-N-ethyl-N-methylformimidamide; N'-(4-(N-(4-bromo-2-methylphenyl)-N-methylglycyl)-2,5-dimethylphenyl)-N-ethyl-N-methylformimidamide; N'-(4-(2-cyano-2-((2,6-dimethylphenyl)thio)acetyl)-2,5-dimethylphenyl)-N-ethyl-N-methylformimidamide; N'-(4-(N-(4-bromo-2-fluorophenyl)-N-methylglycyl)-2,5-dimethylphenyl)-N-ethyl-N-methylformimidamide; N'-(4-(2-cyano-2-(m-tolylthio)propanoyl)-2,5-dimethylphenyl)-N-ethyl-N-methylformimidamide; N'-(4-(N-(2,4-difluorophenyl)-N-methylglycyl)-2,5-dimethylphenyl)-N-ethyl-N-methylformimidamide; N'-(4-(2-((4-chlorophenyl)(methyl)amino)-2-cyanoacetyl)-2,5-dimethylphenyl)-N-ethyl-N-methylformimidamide; N'-(4-(N-(2,6-difluorophenyl)-N-methylglycyl)-2,5-dimethylphenyl)-N-ethyl-N-methylformimidamide; N'-(4-(2-cyano-2-(methyl(phenyl)amino)acetyl)-2,5-dimethylphenyl)-N-ethyl-N-methylformimidamide; N'-(4-(N-(3,4-difluorophenyl)-N-methylglycyl)-2,5-dimethylphenyl)-N-ethyl-N-methylformimidamide; N'-(4-(2-cyano-2-(2,6-dichlorophenoxy)acetyl)-2,5-dimethylphenyl)-N-ethyl-N-methylformimidamide; N'-(4-(N-(3,5-difluorophenyl)-N-methylglycyl)-2,5-dimethylphenyl)-N-ethyl-N-methylformimidamide; N'-(4-(2-cyano-2-(2,6-dibromophenoxy)acetyl)-2,5-dimethylphenyl)-N-ethyl-N-methylformimidamide; N'-(4-(N-(3,5-dimethoxyphenyl)-N-methylglycyl)-2,5-dimethylphenyl)-N-ethyl-N-methylformimidamide; N'-(4-(2-(2-bromo-6-methylphenoxy)-2-cyanoacetyl)-2,5-dimethylphenyl)-N-ethyl-N-methylformimidamide; N'-(4-(N-(3-chloro-5-methoxyphenyl)-N-methylglycyl)-2,5-dimethylphenyl)-N-ethyl-N-methylformimidamide; N'-(4-(2-(dimethylamino)-2-(p-tolyloxy)acetyl)-2,5-dimethylphenyl)-N-ethyl-N-methylformimidamide; N'-(4-(N-(5-chloro-2-methoxyphenyl)-N-methylglycyl)-2,5-dimethylphenyl)-N-ethyl-N-methylformimidamide; N'-(4-(2-(dimethylamino)-2-(m-tolyloxy)acetyl)-2,5-dimethylphenyl)-N-ethyl-N-methylformimidamide; N'-(4-(N-(3-chloro-2-methoxyphenyl)-N-methylglycyl)-2,5-dimethylphenyl)-N-ethyl-N-methylformimidamide; N'-(4-(2-(dimethylamino)-2-phenoxyacetyl)-2,5-dimethylphenyl)-N-ethyl-N-methylformimidamide; N'-(4-(N-(3-chloro-4-methoxyphenyl)-N-methylglycyl)-2,5-dimethylphenyl)-N-ethyl-N-methylformimidamide; N'-(2,5-dimethyl-4-(2-methyl-2-(phenylamino)propanoyl)phenyl)-N-ethyl-N-methylformimidamide; N'-(4-(N-(3-chlorophenyl)-N-methylglycyl)-2,5-dimethylphenyl)-N-ethyl-N-methylformimidamide; N'-(2,5-dimethyl-4-(1-(methyl(phenyl)amino)cyclopropane-1-carbonyl)phenyl)-N-ethyl-N-methylformimidamide; N'-(4-(N-(2-chlorophenyl)-N-methylglycyl)-2,5-dimethylphenyl)-N-ethyl-N-methylformimidamide; N'-(2,5-dimethyl-4-(1-phenoxycyclopropane-1-carbonyl)phenyl)-N-ethyl-N-methylformimidamide; N'-(4-(N-(4-chlorophenyl)-N-methylglycyl)-2,5-dimethylphenyl)-N-ethyl-N-methylformimidamide; N'-(2,5-dimethyl-4-(2-methyl-2-phenoxypropanoyl)phenyl)-N-ethyl-N-methylformimidamide; N-ethyl-N'-(4-((3-fluorophenyl)glycyl)-2,5-dimethylphenyl)-N-methylformimidamide; N'-(4-(2,2-difluoro-2-phenoxyacetyl)-2,5-dimethylphenyl)-N-ethyl-N-methylformimidamide; N-ethyl-N'-(4-((2-fluorophenyl)glycyl)-2,5-dimethylphenyl)-N-methylformimidamide; N'-(4-(2-(4-chlorophenoxy)-2,2-difluoroacetyl)-2,5-dimethylphenyl)-N-ethyl-N-methylformimidamide; N-ethyl-N'-(4-((4-fluorophenyl)glycyl)-2,5-dimethylphenyl)-N-methylformimidamide; N-ethyl-N'-(4-(2-fluoro-2-phenoxyacetyl)-2,5-dimethylphenyl)-N-methylformimidamide; N-ethyl-N'-(4-((2-fluoro-6-methylphenyl)glycyl)-2,5-dimethylphenyl)-N-methylformimidamide; N'-(4-(2,2-difluoro-2-(phenylthio)acetyl)-2,5-dimethylphenyl)-N-ethyl-N-methylformimidamide; N-ethyl-N'-(4-((4-fluoro-2-methylphenyl)glycyl)-2,5-dimethylphenyl)-N-methylformimidamide; N'-(4-(1,1-difluoro-3-phenoxyprop-1-en-2-yl)-2,5-dimethylphenyl)-N-ethyl-N-methylformimidamide; N-ethyl-N'-(4-((3-fluoro-2-methylphenyl)glycyl)-2,5-dimethylphenyl)-N-methylformimidamide; N'-(4-(1,1-difluoro-3-(phenylthio)prop-1-en-2-yl)-2,5-dimethylphenyl)-N-ethyl-N-methylformimidamide; N-ethyl-N'-(4-((3-fluoro-4-methylphenyl)glycyl)-2,5-dimethylphenyl)-N-methylformimidamide; N-ethyl-N'-(4-(2-(2-fluorophenoxy)ethanethioyl)-2,5-dimethylphenyl)-N-methylformimidamide; N-ethyl-N'-(4-((5-fluoro-2-methylphenyl)glycyl)-2,5-dimethylphenyl)-N-methylformimidamide; N'-(2,5-dimethyl-4-(2-(o-tolyloxy)ethanethioyl)phenyl)-N-ethyl-N-methylformimidamide; N'-(4-((2-chloro-6-fluorophenyl)glycyl)-2,5-dimethylphenyl)-N-ethyl-N-methylformimidamide; N'-(4-(2-(2-bromophenoxy)ethanethioyl)-2,5-dimethylphenyl)-N-ethyl-N-methylformimidamide; N'-(4-((2-chloro-5-fluorophenyl)glycyl)-2,5-dimethylphenyl)-N-ethyl-N-methylformimidamide; N'-(4-(2-((4-bromo-2-methylphenyl)amino)ethanethioyl)-2,5-dimethylphenyl)-N-ethyl-N-methylformimidamide; N'-(4-((2-chloro-4-fluorophenyl)glycyl)-2,5-dimethylphenyl)-N-ethyl-N-methylformimidamide; N'-(4-(2-((4-bromo-2-fluorophenyl)amino)ethanethioyl)-2,5-dimethylphenyl)-N-ethyl-N-methylformimidamide; N'-(4-((2-chloro-3-fluorophenyl)glycyl)-2,5-dimethylphenyl)-N-ethyl-N-methylformimidamide; N'-(4-(2-((2,4-difluorophenyl)amino)ethanethioyl)-2,5-dimethylphenyl)-N-ethyl-N-methylformimidamide; N'-(4-((4-chloro-3-fluorophenyl)glycyl)-2,5-dimethylphenyl)-N-ethyl-N-methylformimidamide; N'-(4-(2-((2,6-difluorophenyl)amino)ethanethioyl)-2,5-dimethylphenyl)-N-ethyl-N-methylformimidamide; N'-(4-((4-bromo-3-fluorophenyl)glycyl)-2,5-dimethylphenyl)-N-ethyl-N-methylformimidamide; N'-(4-(2-((3,4-difluorophenyl)amino)ethanethioyl)-2,5-dimethylphenyl)-N-ethyl-N-methylformimidamide; N'-(4-((4-bromo-2-methylphenyl)glycyl)-2,5-dimethylphenyl)-N-ethyl-N-methylformimidamide; N'-(2-(2-((3-chlorophenyl)thio)acetyl)-4-methylpyrimidin-5-yl)-N-ethyl-N-methylformimidamide; N'-(4-((4-bromo-2-fluorophenyl)glycyl)-2,5-dimethylphenyl)-N-ethyl-N-methylformimidamide; N-ethyl-N'-(2-(2-(3-fluorophenoxy)acetyl)-4-methylpyrimidin-5-yl)-N-methylformimidamide; N'-(4-((2,4-difluorophenyl)glycyl)-2,5-dimethylphenyl)-N-ethyl-N-methylformimidamide; N-ethyl-N'-(2-(2-((4-fluorophenyl)thio)acetyl)-4-methylpyrimidin-5-yl)-N-methylformimidamide; N'-(4-((2,6-difluorophenyl)glycyl)-2,5-dimethylphenyl)-N-ethyl-N-methylformimidamide; N'-(5- chloro-6-(2-((3-chlorophenyl)thio)acetyl)-2-methylpyridin-3-yl)-N-ethyl-N-methylformimidamide; N'-(4-((3,4-difluorophenyl)glycyl)-2,5-dimethylphenyl)-N-ethyl-N-methylformimidamide; N'-(5-chloro-2-methyl-6-(2-(3-(methylthio)phenoxy)acetyl)pyridin-3-yl)-N-ethyl-N-methylformimidamide; N'-(4-((3,5-difluorophenyl)glycyl)-2,5-dimethylphenyl)-N-ethyl-N-methylformimidamide; N'-(5-chloro-2-methyl-6-(2-(4-(trifluoromethoxy)phenoxy)acetyl)pyridin-3-yl)-N-ethyl-N-methylformimidamide; N'-(4-((3,5-dimethoxyphenyl)glycyl)-2,5-dimethylphenyl)-N-ethyl-N-methylformimidamide; N'-(5-chloro-6-(2-((4-fluorophenyl)thio)acetyl)-2-methylpyridin-3-yl)-N-ethyl-N-methylformimidamide; N'-(4-((3-chloro-5-methoxyphenyl)glycyl)-2,5-dimethylphenyl)-N-ethyl-N-methylformimidamide; N'-(5-chloro-2-methyl-6-(2-(phenylthio)acetyl)pyridin-3-yl)-N-ethyl-N-methylformimidamide; N'-(4-((5-chloro-2-methoxyphenyl)glycyl)-2,5-dimethylphenyl)-N-ethyl-N-methylformimidamide; N'-(2,5-dimethyl-6-(2-(phenylthio)acetyl)pyridin-3-yl)-N-ethyl-N-methylformimidamide; N'-(4-((3-chloro-2-methoxyphenyl)glycyl)-2,5-dimethylphenyl)-N-ethyl-N-methylformimidamide; 1-(5-chloro-2-methyl-4-((1-methylpyrrolidin-2-ylidene)amino)phenyl)-2-(3-chlorophenoxy)ethan-1-one; N'-(4-((3-chloro-4-methoxyphenyl)glycyl)-2,5-dimethylphenyl)-N-ethyl-N-methylformimidamide; 1-(5-chloro-2-methyl-4-((1-methylpyrrolidin-2-ylidene)amino)phenyl)-2-(4-chlorophenoxy)ethan-1-one; N'-(4-((3-chlorophenyl)glycyl)-2,5-dimethylphenyl)-N-ethyl-N-methylformimidamide; 1-(5-chloro-2-methyl-4-((1-methylpyrrolidin-2-ylidene)amino)phenyl)-2-(3-fluorophenoxy)ethan-1-one; 1-(5-chloro-2-methyl-4-((1-methylpyrrolidin-2-ylidene)amino)phenyl)-2-((4-chlorophenyl)thio)ethan-1-one; N'-(2,5-dimethyl-4-(2-(piperidin-1-yl)acetyl)phenyl)-N-ethyl-N-methylformimidamide; 2-((4-bromophenyl)thio)-1-(2,5-dimethyl-4-((1-methylpyrrolidin-2-ylidene)amino)phenyl)ethan-1-one; N-ethyl-N'-(4-(2-(isoindolin-2-yl)acetyl)-2,5-dimethylphenyl)-N-methylformimidamide; 1-(5-chloro-2-methyl-4-((1-methylpyrrolidin-2-ylidene)amino)phenyl)-2-((3-fluorophenyl)thio)ethan-1-one; N'-(2,5-dimethyl-4-(2-(1-oxoisoindolin-2-yl)acetyl)phenyl)-N-ethyl-N-methylformimidamide; N'-(2,5-dimethyl-4-(3-methyl-1-(methyl(phenyl)amino)but-2-en-2-yl)phenyl)-N-ethyl-N-methylformimidamide; N'-(4-(3-((2,6-difluorophenyl)thio)-1,1-difluoroprop-1-en-2-yl)-2,5-dimethylphenyl)-N-ethyl-N-methylformimidamide; N'-(4-(3-((2,6-difluorophenyl)(methyl)amino)prop-1-en-2-yl)-2,5-dimethylphenyl)-N-ethyl-N-methylformimidamide and N'-(4-(3-((2-bromophenyl)thio)-1,1-difluoroprop-1-en-2-yl)-2-chloro-5-methylphenyl)-N, N-dimethylformimidamide.

5. A composition for controlling or preventing phytopathogenic microorganisms comprising a compound of formula (I) according to claim 1 one or more inert carriers.

6. The composition according to claim 5, wherein said composition may additionally comprises one or more active compatible compounds selected from fungicides, insecticides, nematicides, acaricides, biopesticides, herbicides, plant growth regulators, antibiotics, fertilizers and/or mixtures thereof.

7. The composition according to claim 5, wherein the concentration of compounds of formula (I) ranges from 1 to 90% by weight with respect to the total weight of the composition.

8. A method for controlling phytopathogenic fungi, bacteria, insects, nematodes, and/or mites, the method comprising: applying the compound of claim 1 to agricultural and/or horticultural crops.

9. The method of claim 8 for controlling or preventing against phytopathogenic fungi.

10. The method of claim 8, for controlling rust diseases.

11. The method of claim 10, wherein said rust diseases are *Hemileia vastatrix* (Coffee rust), *Uromyces appendiculatus/fabae/phaseoli* (rust of beans) *Puccinia* spp. (rusts) on various plants, selected from *P. triticina* (brown or leaf rust), *P. striiformis* (stripe or yellow rust), *Puccinia melanocephala* (sugarcane rust), *P. hordei* (dwarf rust), *P. graminis* (stem or black rust) or *P. recondita* (brown or leaf rust), on cereals, selected from wheat, barley or rye and *Phakopsora* spp. on various plants.

12. The method of claim 8, for controlling or preventing against *Phakopsora pachyrhizi* or *Phakopsora meibomiae*.

13. The method of claim 12, wherein said agricultural crops are selected from the group consisting of cereals, corn, rice, soybean and other leguminous plants, fruits and fruit trees, nuts and nut trees, citrus and citrus trees, horticultural plants, cucurbitaceae, oleaginous plants, tobacco, coffee, tea, cacao, sugar beet, sugar cane, cotton, potato, tomato, onions, peppers and other vegetables, and ornamentals.

14. A method of controlling or preventing infestation of useful plants by phytopathogenic microorganisms in agricultural crops and or horticultural crops wherein the compounds of formula (I) according to claim 1 is applied to the plants, to parts thereof or the locus thereof.

15. A method of controlling or preventing infestation of useful plants by phytopathogenic microorganisms in agricultural crops and or horticultural crops wherein the compounds of formula (I) according to claim 1 is applied to the seeds of plants.

16. A method of controlling or preventing phytopathogenic microorganisms in agricultural crops and or horticultural crops using the compounds of formula (I) according to claim 1 or composition thereof which consists in applying effective dosages of compounds or compositions in amounts ranging from 1 g to 5 kg per hectare of agricultural or horticultural crops.

17. The composition according to claim 5, wherein the concentration of compounds of formula (I) ranges from 5 to 50% by weight with respect to the total weight of the composition.

* * * * *